United States Patent
Jeong et al.

(10) Patent No.: US 10,381,596 B2
(45) Date of Patent: Aug. 13, 2019

(54) ORGANIC LIGHT-EMITTING DISPLAY APPARATUS WITH AN ENCAPSULATION UNIT

(71) Applicant: Samsung Display Co., Ltd., Yongin-si, Gyeonggi-do (KR)

(72) Inventors: Eunjae Jeong, Yongin-si (KR); Youngkook Kim, Yongin-si (KR); Yohan Kim, Yongin-si (KR); Esu Kim, Yongin-si (KR); Jongwoo Kim, Yongin-si (KR); Jangyeol Baek, Yongin-si (KR); Wonmin Yun, Yongin-si (KR); Sanghyun Han, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 15/973,289

(22) Filed: May 7, 2018

(65) Prior Publication Data
US 2019/0051860 A1 Feb. 14, 2019

(30) Foreign Application Priority Data
Aug. 9, 2017 (KR) .................. 10-2017-0101347

(51) Int. Cl.
*H01L 51/52* (2006.01)
*C07D 221/14* (2006.01)
(Continued)

(52) U.S. Cl.
CPC ........ *H01L 51/5253* (2013.01); *C07D 221/14* (2013.01); *C07D 401/10* (2013.01);
(Continued)

(58) Field of Classification Search
CPC ............. H01L 51/0071; H01L 51/0072; H01L 51/0073; H01L 51/5237; H01L 51/5253
See application file for complete search history.

(56) References Cited

U.S. PATENT DOCUMENTS

| 5,093,691 | A | 3/1992 | Utsugi et al. |
| 9,368,731 | B2 * | 6/2016 | Saito .................. H01L 51/0072 |
| 9,461,272 | B2 | 10/2016 | Yang |

FOREIGN PATENT DOCUMENTS

| JP | 3082284 B2 | 8/2000 |
| JP | 2009-197171 A | 9/2009 |

(Continued)

OTHER PUBLICATIONS

Extended European Search Report dated Dec. 11, 2018, for corresponding European Patent Application No. 18187869.5, 9 pages.

*Primary Examiner* — Quoc D Hoang
(74) *Attorney, Agent, or Firm* — Lewis Roca Rothgerber Christie LLP

(57) ABSTRACT

An organic light-emitting display apparatus includes a substrate, an organic light-emitting device disposed above the substrate, and an encapsulation unit disposed above the organic light-emitting device and sealing the organic light-emitting device, wherein the encapsulation unit includes a compound represented by Formula 1.

$$[R_1\text{-}(L_1)_{a1}]_{b1}\text{-}(Ar_1)_{c1}\text{-}[(L_2)_{a2}\text{-}R_2]_{b2}. \quad \text{Formula 1}$$

20 Claims, 2 Drawing Sheets

(51) Int. Cl.
*C07D 401/10* (2006.01)
*H01L 27/32* (2006.01)
*H01L 51/00* (2006.01)

(52) U.S. Cl.
CPC ........ *H01L 27/322* (2013.01); *H01L 27/3244* (2013.01); *H01L 51/0067* (2013.01); *H01L 51/0072* (2013.01); *H01L 51/5237* (2013.01)

(56) References Cited

FOREIGN PATENT DOCUMENTS

| | | |
|---|---|---|
| KR | 10-2016-0081105 A | 7/2016 |
| WO | WO 2015093093 A1 | 6/2015 |
| WO | WO 2015098549 A1 | 7/2015 |

\* cited by examiner

ORGANIC LIGHT-EMITTING DISPLAY APPARATUS WITH AN ENCAPSULATION UNIT

CROSS-REFERENCE TO RELATED APPLICATION

This application claims priority to and the benefit of Korean Patent Application No. 10-2017-0101347, filed on Aug. 9, 2017, in the Korean Intellectual Property Office, the disclosure of which is incorporated herein in its entirety by reference.

BACKGROUND

1. Field

One or more embodiments relate to an organic light-emitting display apparatus.

2. Description of the Related Art

An organic light-emitting display apparatus is a self-emission device and includes an organic light-emitting device, which includes a hole injection electrode, an electron injection electrode, and an organic emission layer between the hole injection electrode and the electron injection. Holes provided from the hole injection electrode and electrons provided from the electron injection electrode recombine in the organic emission layer to produce excitons. These excitons transit from an excited state to a ground state, thereby generating light.

Because the organic light-emitting display apparatus, which is a self-emission device, does not require a separate light source, the organic light-emitting display apparatus may be driven at a low voltage and configured to be lightweight and thin. Also, because of excellent characteristics in terms of a viewing angle, contrast, response time, and/or the like, the applications of the organic light-emitting display apparatus have expended from personal portable devices (such as MP3 players or mobile phones) to televisions.

However, if ultraviolet rays or the like are introduced from the outside into the organic light-emitting display apparatus, or if ultraviolet rays are introduced in the process of manufacturing the organic light-emitting display apparatus and penetrate into the organic light-emitting display apparatus, an emission layer, an insulating film, and/or the like including an organic material may be particularly seriously damaged.

SUMMARY

Aspects of the present disclosure are directed toward an organic light-emitting display apparatus capable of reducing an amount of ultraviolet rays transmitting through the organic light-emitting display apparatus.

Additional aspects will be set forth in part in the description which follows and, in part, will be apparent from the description, or may be learned by practice of the presented embodiments.

According to an embodiment of the present disclosure, an organic light-emitting display apparatus includes:
a substrate;
an organic light-emitting device on the substrate; and
an encapsulation unit on the organic light-emitting device and configured to seal the organic light-emitting device,
wherein the encapsulation unit includes a first compound represented by Formula 1:

$$[R_1\text{-}(L_1)_{a1}]_{b1}\text{-}(Ar_1)_{c1}\text{-}[(L_2)_{a2}\text{-}R_2]_{b2}$$ Formula 1

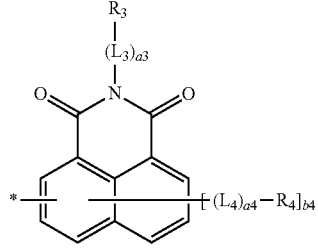

Formula 2-1

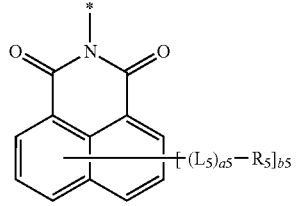

Formula 2-2

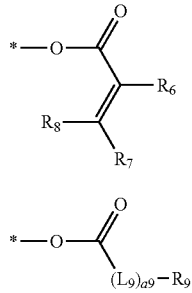

Formula 2-3

Formula 2-4

In Formulae 1 and 2-1 to 2-4,

An may be a $C_5$-$C_{60}$ carbocyclic group or a $C_2$-$C_{30}$ heterocyclic group, c1 may be 0 or 1, $L_1$ to $L_5$ and $L_9$ may each independently be selected from *—N($R_{11}$)—*', *—B($R_{11}$)—*', *—P($R_{11}$)—*', *—Si($R_{11}$)($R_{12}$)—*', *—S—*', *—Se—*', *—O—*', *—C(=O)—*', *—S(=O)—*', *—S(=O)$_2$—*', *—C($R_{11}$)=*', *—C(=S)—*', a substituted or unsubstituted $C_1$-$C_{60}$ alkylene group, a substituted or unsubstituted $C_2$-$C_{60}$ alkenylene group, a substituted or unsubstituted $C_2$-$C_{60}$ alkynylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a5 and a9 may each independently be an integer from 0 to 10, $R_1$ may be a group represented by Formula 2-1 or a group represented by Formula 2-2, $R_2$ to $R_5$ may each independently be selected from a group represented by Formula 2-3, a group represented by Formula 2-4, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, $-N(Q_1)(Q_2)$, $-B(Q_1)(Q_2)$, $-C(=O)(Q_1)$, $-S(=O)_2(Q_1)$, and $-P(=O)(Q_1)(Q_2)$, $R_6$ to $R_9$, $R_{11}$, and $R_{12}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_4)(Q_5)(Q_6)$, $-N(Q_4)(Q_5)$, $-B(Q_4)(Q_5)$, $-C(=O)(Q_4)$, $-S(=O)_2(Q_4)$, and $-P(=O)(Q_4)(Q_5)$, b1 may be an integer from 1 to 10, wherein, when b1 is two or more, two or more *-$(L_1)_{a1}$-$R_1$(s) may be identical to or different from each other, b2 may be an integer from 1 to 10, wherein, when b2 is two or more, two or more *-$(L_2)_{a2}$-$R_2$(s) may be identical to or different from each other, b4 may be an integer from 0 to 5, wherein, when b4 is two or more, two or more *-$(L_4)_{a4}$-$R_4$(s) may be identical to or different from each other, b5 may be an integer from 0 to 6, wherein, when b5 is two or more, two or more *-$(L_5)_{a5}$-$R_5$(s) may be identical to or different from each other, at least one substituent of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cycloalkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cycloalkoxy group;

a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cycloalkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{11})(Q_{12})(Q_{13})$, $-N(Q_{11})(Q_{12})$, $-B(Q_{11})(Q_{12})$, $-C(=O)(Q_{11})$, $-S(=O)_2(Q_{11})$, and $-P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{21})(Q_{22})(Q_{23})$, $-N(Q_{21})(Q_{22})$, $-B(Q_{21})(Q_{22})$, $-C(=O)(Q_{21})$, $-S(=O)_2(Q_{21})$, and $-P(=O)(Q_{21})(Q_{22})$; and $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, and $-P(=O)(Q_{31})(Q_{32})$, $Q_1$ to $Q_6$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group, and

* and *' each indicate a binding site to a neighboring atom.

According to another embodiment, an organic light-emitting display apparatus includes:

a substrate;

an organic emission unit on the substrate and including a plurality of organic light-emitting devices; and an encapsulation unit on the organic emission unit and sealing the organic emission unit, wherein the encapsulation unit includes a first compound represented by Formula 1.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
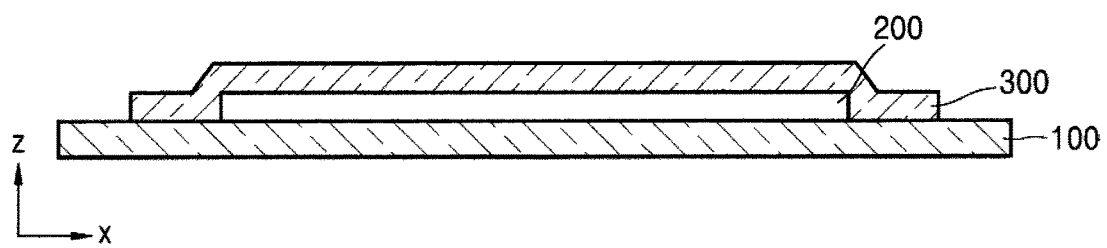
FIG. 1 is a schematic cross-sectional view of an organic light-emitting display apparatus according to an embodiment.

The present disclosure will now be described more fully with reference to exemplary embodiments. The disclosure may, however, be embodied in many different forms and should not be construed as being limited to the embodiments set forth herein; rather, these embodiments are provided so that this disclosure will be thorough and complete, and will fully convey the concept of the disclosure to those skilled in the art. Enhancements and features of the present invention and how to achieve them will become apparent by reference to the embodiment that will be described later in more detail, together with the accompanying drawings. This invention may, however, be embodied in many different forms and should not be limited to the exemplary embodiments.

Hereinafter, embodiments are described in more detail by referring to the accompanying drawings. In the drawings, like reference numerals denote like elements, and a redundant explanation thereof will not be provided herein.

It will be understood that when a layer, film, region, or plate is referred to as being "formed on" another layer, film, region, or plate, it can be directly or indirectly formed on the other layer, film, region, or plate. That is, for example, intervening layers, films, regions, or plates may be present. In addition, sizes of components in the drawings may be exaggerated for convenience of explanation. In other words, because sizes and thicknesses of components in the drawings are arbitrarily illustrated for convenience of explanation, the following embodiments of the present disclosure are not limited thereto.

Hereinafter, the terms "first, second, etc.," are used only for the purpose of distinguishing one element from another.

In the following Examples, the x-axis and the z-axis are not limited to two axes on the rectangular coordinate system, and may be interpreted in a broader sense. For example, the x-axis and the z-axis may cross each other at right angles, but they may also refer to different directions that the axes do not cross each other at right angles.

FIG. 1 is a schematic cross-sectional view of an organic light-emitting display apparatus according to an embodiment.

In FIG. 1, an organic light-emitting display apparatus according to an embodiment includes a substrate 100, an organic light-emitting device 200, and an encapsulation unit 300.

The substrate 100 may be any one of various suitable substrates that are utilized in an organic light-emitting display apparatus in the related art, and may be an inorganic substrate or an organic substrate, each having high mechanical strength, thermal stability, transparency, surface smoothness, ease of handling, and/or water repellency.

For example, the substrate may be an inorganic substrate made of a transparent glass material including $SiO_2$ as a main component, but embodiments of the present disclosure are not limited thereto.

In one or more embodiment, the substrate may be an organic substrate having an insulating property. An organic material having the insulating property may be selected from, for example, polyethersulphone (PES), polyacrylate (PAR), polyetherimide (PEI), polyethyelenen napthalate (PEN), polyethyleneterephthalate (PET), polyphenylene sulfide (PPS), polyallylate, polyimide, polycarbonate (PC), cellulose triacetate (TAC), and cellulose acetate propionate (CAP), but embodiments of the present disclosure are not limited thereto.

The organic light-emitting device 200 is disposed on the substrate 100. The organic light-emitting device 200 may include a first electrode, an intermediate layer including an emission layer, and a second electrode.

The first electrode may be formed by, for example, depositing or sputtering a material for forming the first electrode on the substrate. When the first electrode is an anode, the material for forming the first electrode may be selected from materials with a high work function to facilitate hole injection.

The first electrode may be a reflective electrode, a semi-transmissive electrode, or a transmissive electrode. When the first electrode is a transmissive electrode, a material for forming the first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode is a semi-transmissive electrode or a reflective electrode, a material for forming the first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode may have a single-layered structure, or a multi-layered structure including two or more layers. For example, the first electrode may have a three-layered structure of ITO/Ag/ITO, but the structure of the first electrode is not limited thereto.

On the first electrode, an interlayer including an emission layer may be disposed.

The interlayer may further include a hole transport region between the first electrode and the emission layer, and an electron transport region between the emission layer and the second electrode.

On the interlayer, the second electrode may be disposed. The second electrode may be a cathode that is an electron injection electrode, and in this regard, a metal for forming the second electrode may be a material having a low work function, such as a metal, an alloy, an electrically conductive compound, or a mixture thereof.

The second electrode may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode may be a transmissive electrode, a semi-transmissive electrode, or a reflective electrode.

The first electrode may have a single-layered structure, or a multi-layered structure including two or more layers.

On the organic light-emitting device 200, the encapsulation unit 300 may be disposed.

The encapsulation unit 300 may include a first compound represented by Formula 1 below:

$$[R_1\text{-}(L_1)_{a1}]_{b1}\text{-}(Ar_1)_{c1}\text{-}[(L_2)_{a2}\text{-}R_2]_{b2} \qquad \text{Formula 1}$$

In Formula 1, $Ar_1$ may be a $C_5$-$C_{60}$ carbocyclic group or a $C_2$-$C_{30}$ heterocyclic group.

For example, $Ar_1$ may be selected from a benzene group, a naphthalene group, an anthracene group, a phenanthrene group, a pyrene group, a chrysene group, a triphenylene group, an indene group, a fluorene group, a benzofluorene group, a spiro-bifluorene group, a carbazole group, a dibenzofuran group, a dibenzothiophene group, a pyridine group, a pyrazine group, a pyrimidine group, a pyridazine group, a pyrrole group, an imidazole group, a quinoline group, an isoquinoline group, a quinoxaline group, a quinazoline group, a triazine group, an indeno pyrazine group, an indeno pyridine group, a phenanthroline group, and a phenanthridine group.

In one embodiment, An may be selected from a benzene group, a naphthalene group, an anthracene group, a fluorene group, a spiro-bifluorene group, a carbazole group, a dibenzofuran group, a dibenzothiophene group, a pyridine group, a pyrazine group, a pyrimidine group, a pyridazine group, and a triazine group.

In one or more embodiments, $Ar_1$ may be selected from a benzene group, a naphthalene group, an anthracene group, a dibenzofuran group, a dibenzothiophene group, a pyridine group, and a triazine group, but embodiments of the present disclosure are not limited thereto.

In Formula 1, c1 may be 0 or 1. c1 indicates the number of $Ar_1$, and when c1 is 0, *—$Ar_1$—*' is a single bond.

In Formula 1, $R_1$ may be a group represented by Formula 2-1 or a group represented by Formula 2-2:

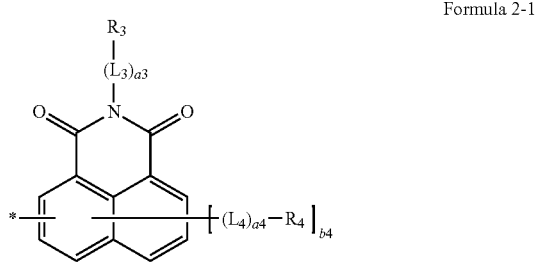

Formula 2-1

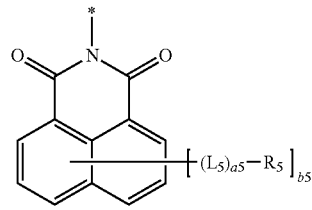

Formula 2-2

In Formulae 2-1 and 2-2, $L_3$ to $L_5$, a3 to a5, $R_3$ to $R_5$, b4, and b5 are the same as described above, and * indicates a binding site to a neighboring atom.

In Formulae 1, 2-1, and 2-2, $R_2$ to $R_5$ may each independently be selected from: a group represented by Formula 2-3, a group represented by Formula 2-4, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$:

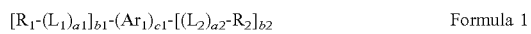

Formula 2-3

Formula 2-4

$Q_1$ to $Q_3$, $L_9$, a9, and $R_6$ to $R_9$ are the same as described above, and * indicates a binding site to a neighboring atom.

In Formulae 1, 2-1, 2-2, and 2-4, $L_1$ to $L_5$ and $L_9$ may each independently be selected from *—$N(R_{11})$—*', *—B $(R_{11})$—*', *—$P(R_{11})$—*', *—$Si(R_{11})(R_{12})$—*', *—S—*', *—Se—*', *—O—*', *—$C(=O)$—*', *—$S(=O)$—*', *—$S(=O)_2$—*', *—$C(R_{11})$—*', *—$C(=S)$—*', a substituted or unsubstituted $C_1$-$C_{60}$ alkylene group, a substituted or unsubstituted $C_2$-$C_{60}$ alkenylene group, a substituted or unsubstituted $C_2$-$C_{60}$ alkynylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, $L_1$ to $L_5$ and $L_9$ may each independently be selected from:

*—S—*', *—O—*', *—C(=O)—*', *—S(=O)—*', *—S(=O)$_2$—*', a $C_1$-$C_{20}$ alkylene group, a $C_2$-$C_{20}$ alkenylene group, a $C_2$-$C_{20}$ alkynylene group, a phenylene group, a pentalenylene group, an indenylene group, a naphthylene group, an azulenylene group, an indacenylene group, an acenaphthylene group, a fluorenylene group, a spiro-bifluorenylene group, a spiro-benzofluorene-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a carbazolylene group, a benzocarbazolylene group, a dibenzocarbazolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azaspiro-bifluorenylene group, an azacarbazolylene group, an azadibenzofuranylene group, an azadibenzothiophenylene group, and an azadibenzosilolylene group; and a $C_1$-$C_{20}$ alkylene group, a $C_2$-$C_{20}$ alkenylene group, a $C_2$-$C_{20}$ alkynylene group, a phenylene group, a pentalenylene group, an indenylene group, a naphthylene group, an azulenylene group, an indacenylene group, an acenaphthylene group, a fluorenylene group, a spiro-bifluorenylene group, a spiro-benzofluorene-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a carbazolylene group, a benzocarbazolylene group, a dibenzocarbazolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azaspiro-bifluorenylene group, an azacarbazolylene group, an azadibenzofuranylene group, an azadibenzothiophenylene group, and an azadibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{20}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, and —Si($Q_{31}$)($Q_{32}$)($Q_{33}$), $Q_{31}$ to $Q_{33}$ may each independently be selected from:

a $C_1$-$C_{10}$ alkyl group, a $C_1$-$C_{10}$ alkoxy group, a $C_3$-$C_{10}$ cycloalkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a $C_1$-$C_{10}$ alkyl group, a $C_1$-$C_{10}$ alkoxy group, a $C_3$-$C_{10}$ cycloalkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, a $C_3$-$C_{10}$ cycloalkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, and

* and *' each indicate a binding site to a neighboring atom.

In one embodiment, $L_1$ to $L_5$ and $L_9$ may each independently be selected from *—S—*', *—O—*', *—C(=O)—*', *—S(=O)—*', *—S(=O)$_2$—*', *—[C($Z_1$)($Z_2$)]$_{n1}$—*', and groups represented by Formulae 3-1 to 3-75, but embodiments of the present disclosure are not limited thereto:

Formula 3-1

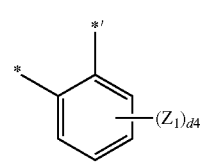

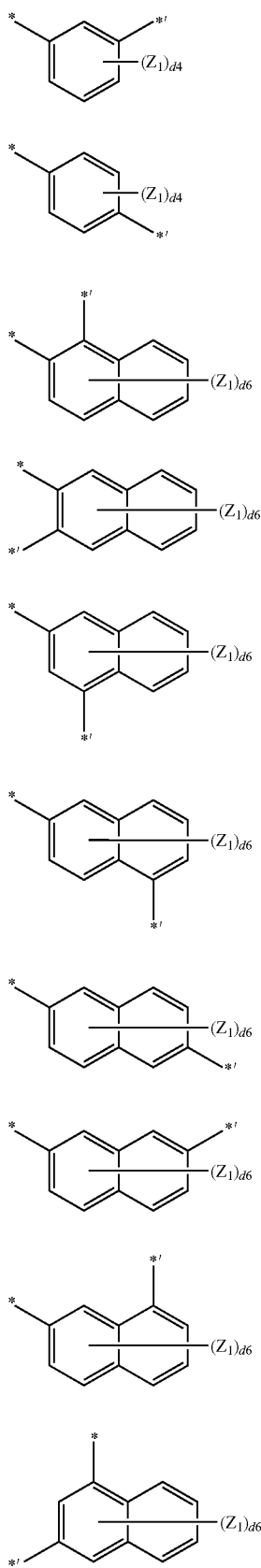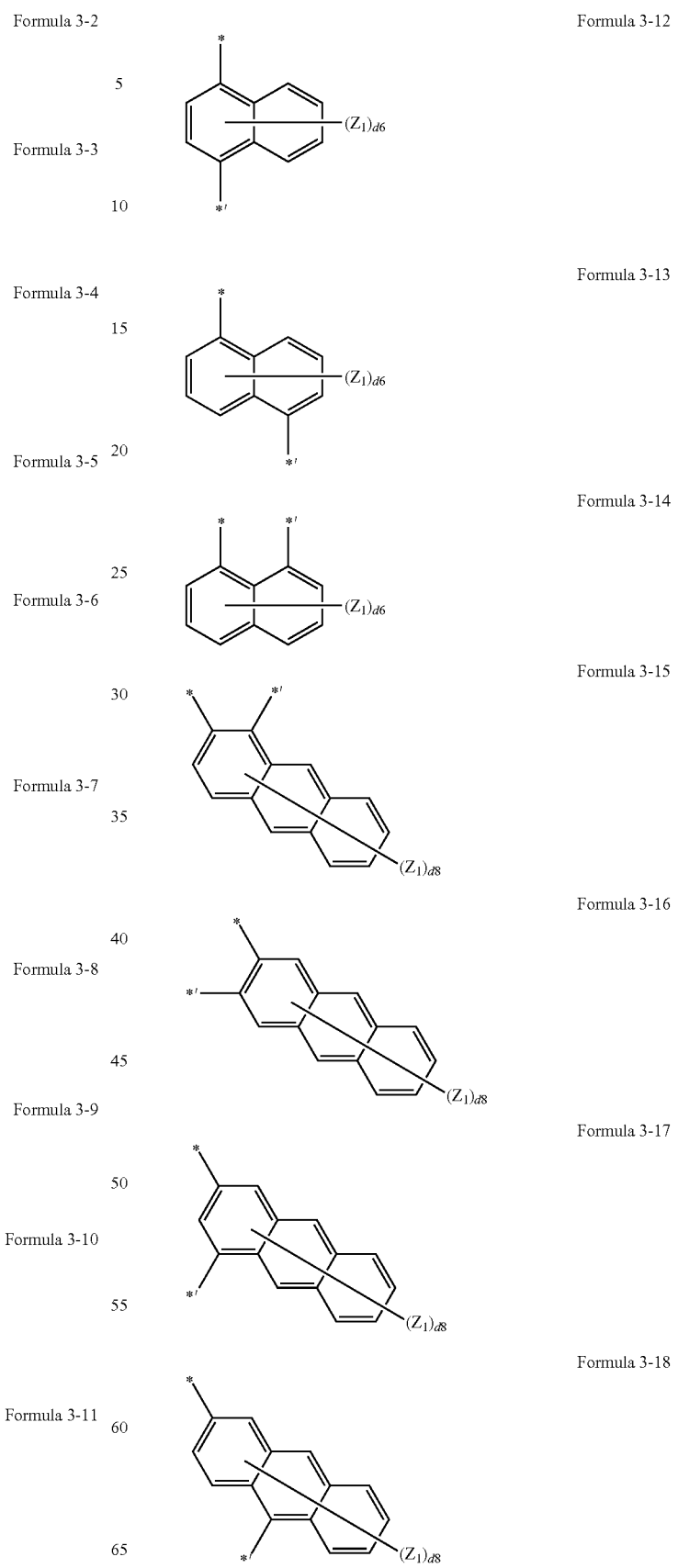

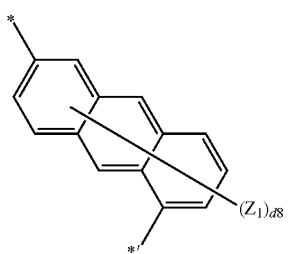
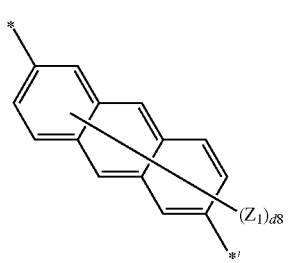
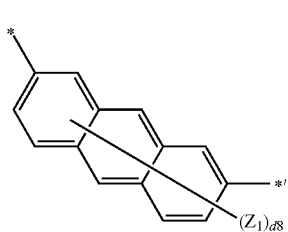
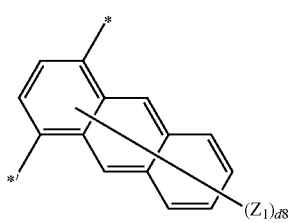
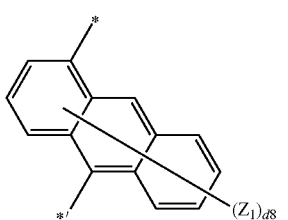
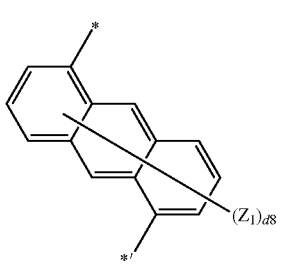
Formula 3-19
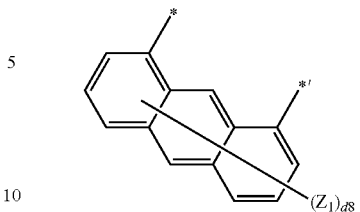
Formula 3-20
Formula 3-21
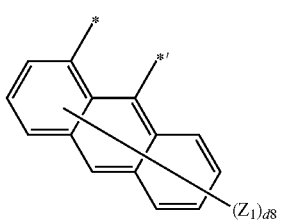
Formula 3-22
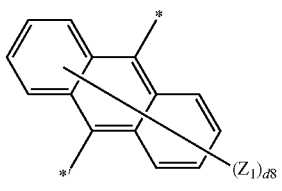
Formula 3-23
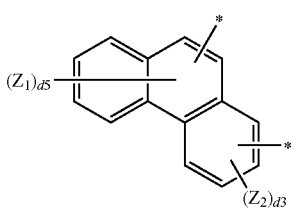
Formula 3-24
Formula 3-25
Formula 3-26
Formula 3-27
Formula 3-28
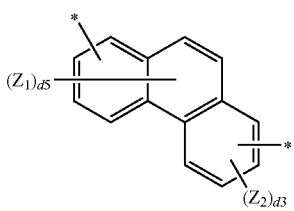
Formula 3-29
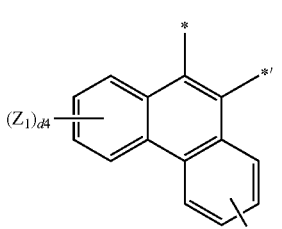
Formula 3-30
Formula 3-31
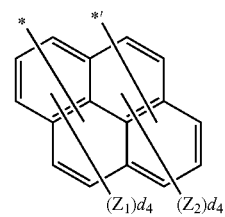

-continued
Formula 3-32
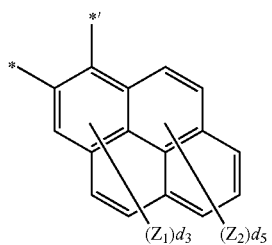
Formula 3-33
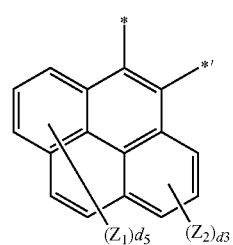
Formula 3-34
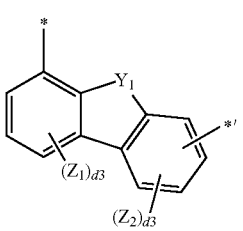
Formula 3-35
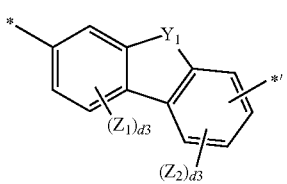
Formula 3-36
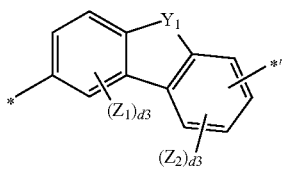
Formula 3-37
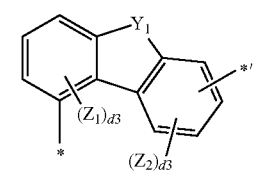
Formula 3-38
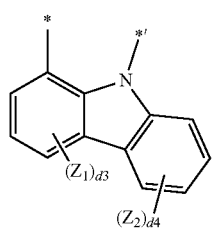
Formula 3-39
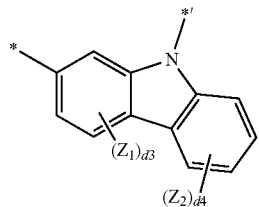
Formula 3-40
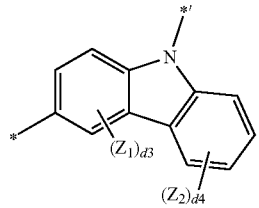
Formula 3-41
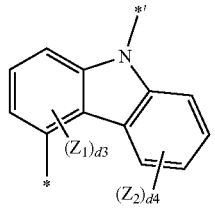
Formula 3-42
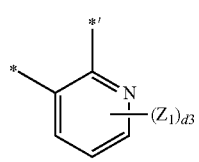
Formula 3-43
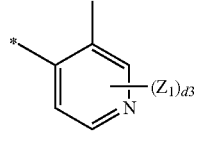
Formula 3-44
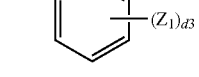
Formula 3-45
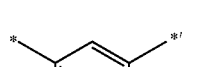
Formula 3-46
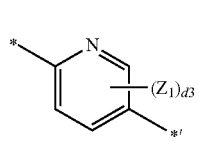
Formula 3-47

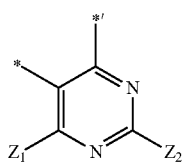 Formula 3-48
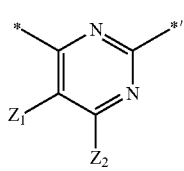 Formula 3-49
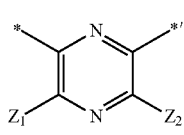 Formula 3-50
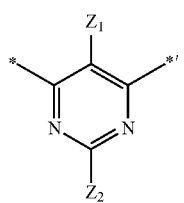 Formula 3-51
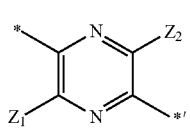 Formula-52
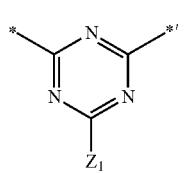 Formula 3-53
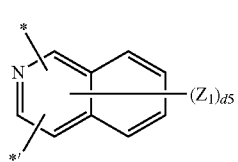 Formula 3-54
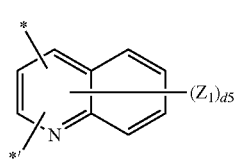 Formula 3-55
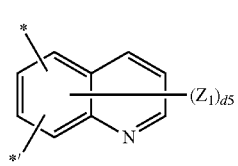 Formula 3-56
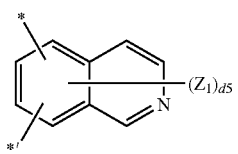 Formula 3-57
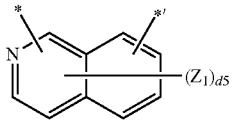 Formula 3-58
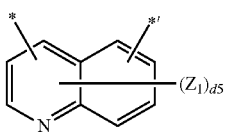 Formula 3-59
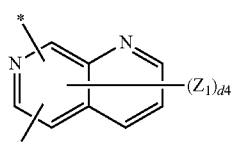 Formula 3-60
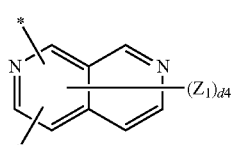 Formula 3-61
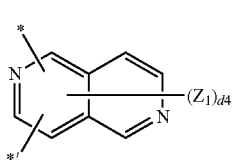 Formula 3-62
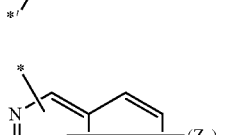 Formula 3-63
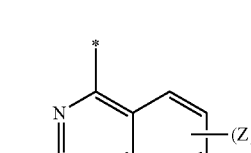 Formula 3-64
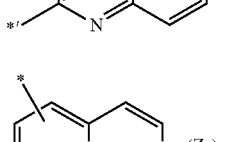 Formula 3-65
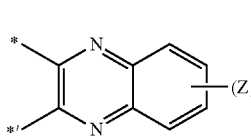 Formula 3-66

-continued

Formula 3-67
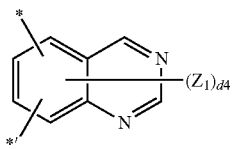

Formula 3-68
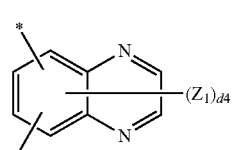

Formula 3-69
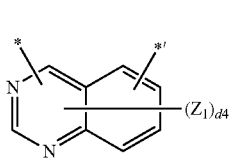

Formula 3-70
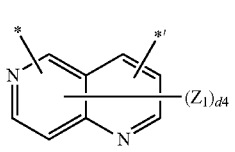

Formula 3-71
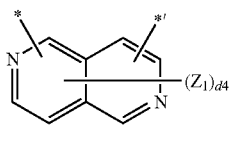

Formula 3-72
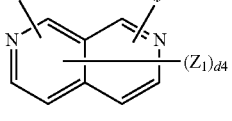

Formula 3-73
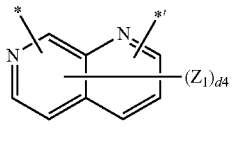

Formula 3-74
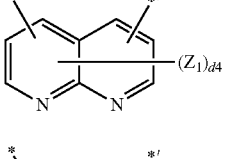

Formula 3-75
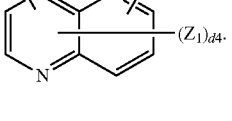

In Formulae 3-1 to 3-75, $Y_1$ may be O, S, $C(Z_3)(Z_4)$, $N(Z_3)$, or $Si(Z_3)(Z_4)$, $Z_1$ to $Z_4$ may each independently be selected from hydrogen, deuterium, —F, —CF$_3$, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a triazinyl group, and —Si(Q$_{31}$)(Q$_{32}$)(Q$_{33}$), $Q_{31}$ to $Q_{33}$ may each independently be selected from a $C_1$-$C_{10}$ alkyl group, a $C_1$-$C_{10}$ alkoxy group, a $C_3$-$C_{20}$ cycloalkoxy group, a phenyl group, a biphenyl group, a terphenyl group, and a naphthyl group, d3 may be an integer from 1 to 3,
d4 may be an integer from 1 to 4,
d5 may be an integer from 1 to 5,
d6 may be an integer from 1 to 6,
d8 may be an integer from 1 to 8,
n1 may be an integer from 1 to 20, and
* and *' each indicate a binding site to a neighboring atom.

a1 to a5 and a9 in Formulae 1, 2-1, 2-2, and 2-4 may each independently be an integer from 0 to 10. a1 indicates the number of $L_1$(s), wherein, when a1 is zero, *-$L_1$-*' may be a single bond, and when a1 is two or more, two or more $L_1$(s) may be identical to or different from each other.

For example, a1 to a5 and a9 may each independently be an integer from 0 to 6.

In one embodiment, a1 to a5 and a9 may each independently be an integer from 0 to 3.

In one or more embodiments, a1 to a5 and a9 may each independently be 0, 1, or 2, but embodiments of the present disclosure are not limited thereto.

In one embodiment, Ar$_1$ in Formula 1 may be selected from groups represented by Formulae 4-1 to 4-59, and $L_1$ to $L_5$ and $L_9$ in Formulae 1, 2-1, 2-2, and 2-4 may each independently be selected from *—O—*', *—C(=O)—*', *—CH$_2$—*', *—(CH$_2$)$_2$—*', *—(CH$_2$)$_3$—*', *—(CH$_2$)$_4$—*', *—(CH$_2$)$_5$—*', and groups represented by Formulae 4-1 to 4-58 and 4-60, but embodiments of the present disclosure are not limited thereto:

Formula 4-1
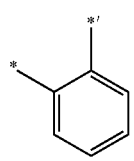

Formula 4-2
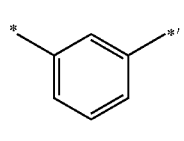

Formula 4-3
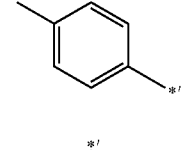

Formula 4-4
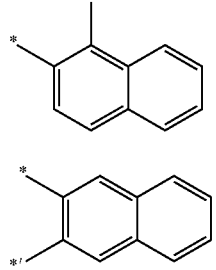

Formula 4-5
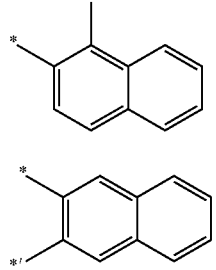

-continued
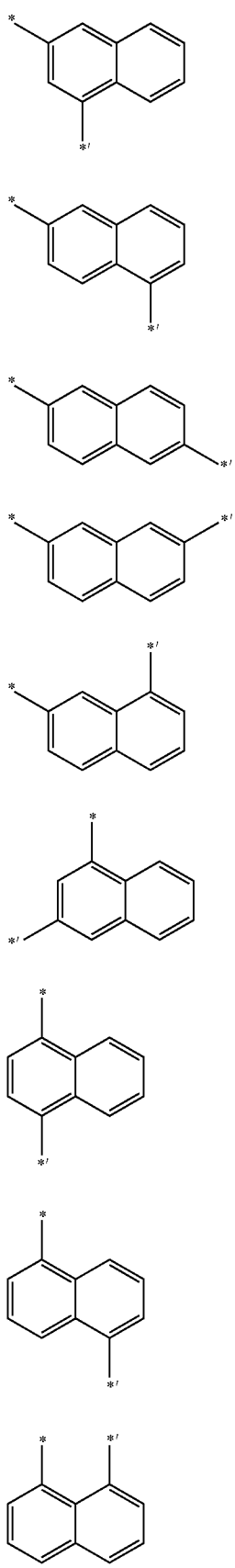
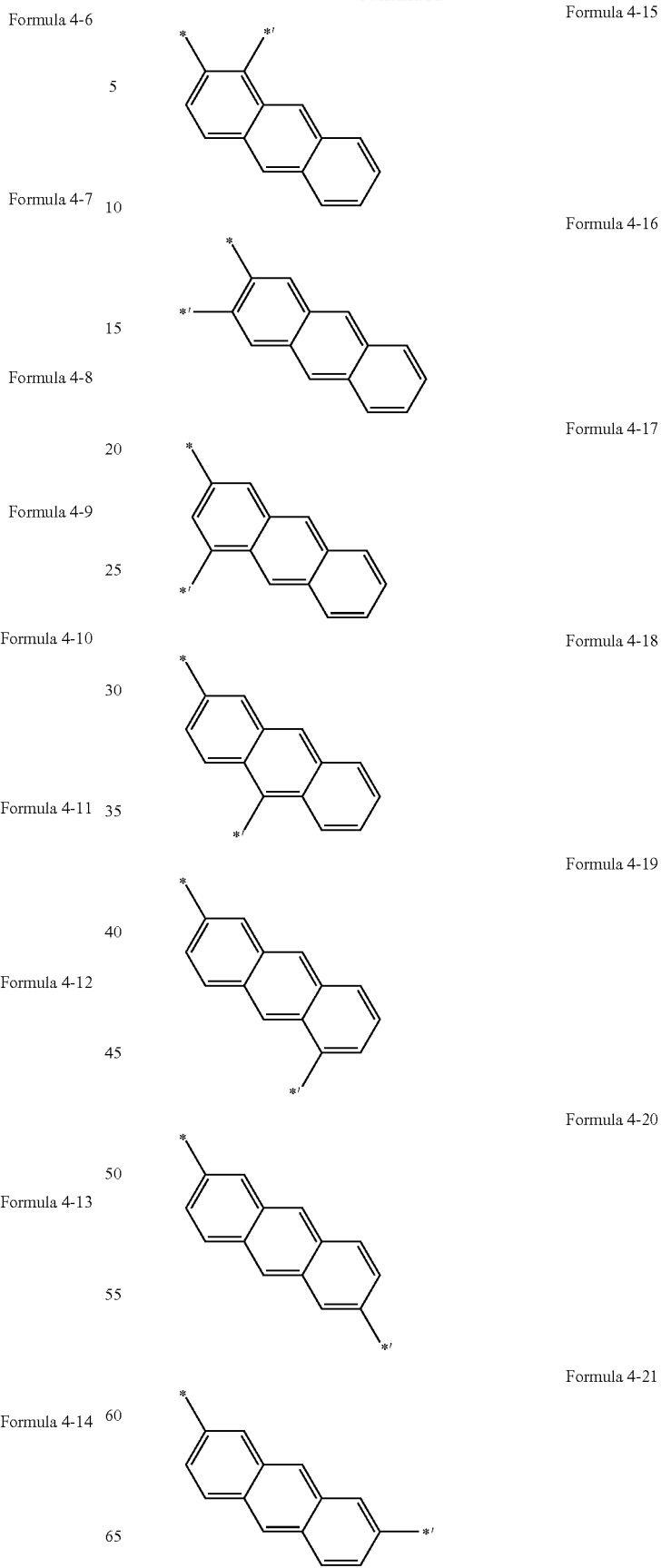
Formula 4-6
Formula 4-7
Formula 4-8
Formula 4-9
Formula 4-10
Formula 4-11
Formula 4-12
Formula 4-13
Formula 4-14
Formula 4-15
Formula 4-16
Formula 4-17
Formula 4-18
Formula 4-19
Formula 4-20
Formula 4-21

Formula 4-22
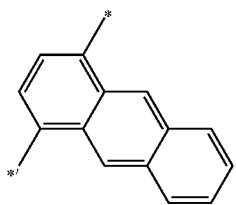
Formula 4-23
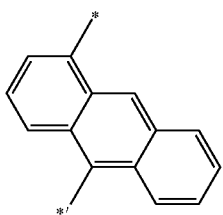
Formula 4-24
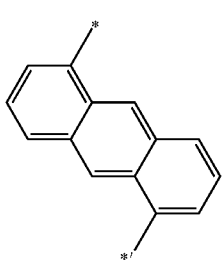
Formula 4-25
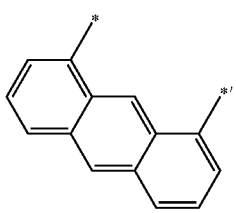
Formula 4-26
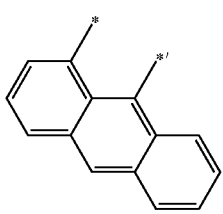
Formula 4-27
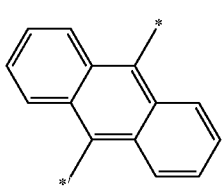
Formula 4-28
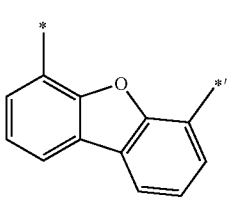
Formula 4-29
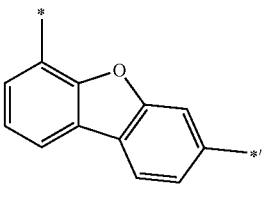
Formula 4-30
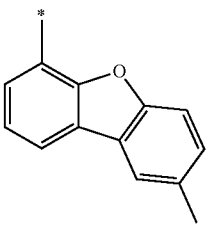
Formula 4-31
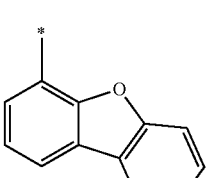
Formula 4-32
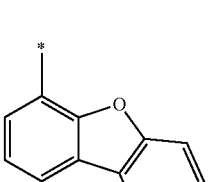
Formula 4-33
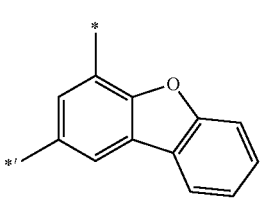
Formula 4-34
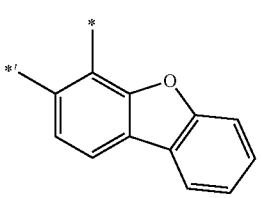
Formula 4-35
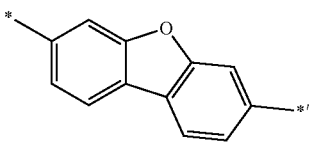

Formula 4-36
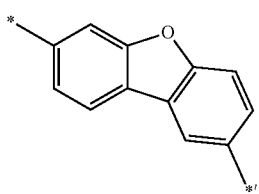
Formula 4-37
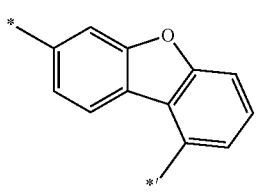
Formula 4-38
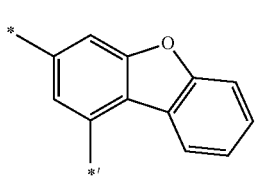
Formula 4-39
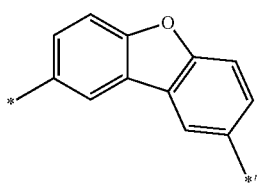
Formula 4-40
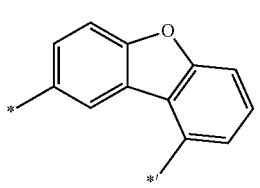
Formula 4-41
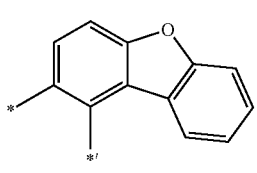
Formula 4-42
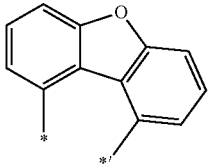
Formula 4-43
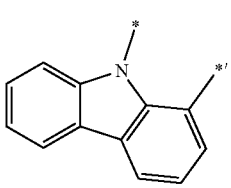
Formula 4-44
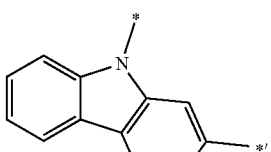
Formula 4-45
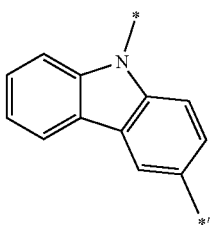
Formula 4-46
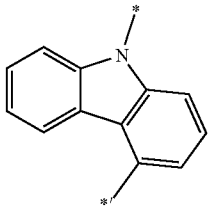
Formula 4-47
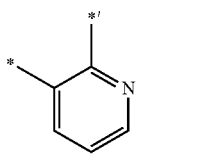
Formula 4-48
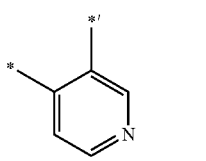
Formula 4-49
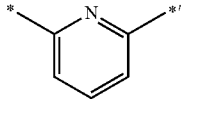
Formula 4-50
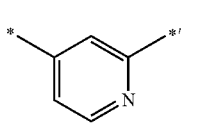
Formula 4-51
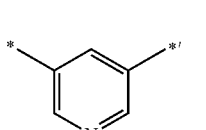
Formula 4-52
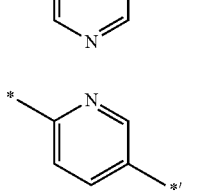

-continued

Formula 4-53
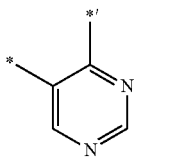

Formula 4-54
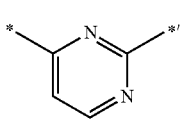

Formula 4-55
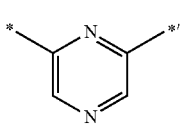

Formula 4-56
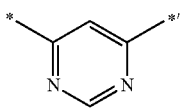

Formula 4-57
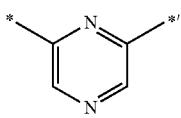

Formula 4-58
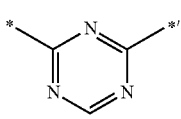

Formula 4-59
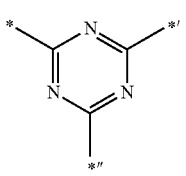

Formula 4-60
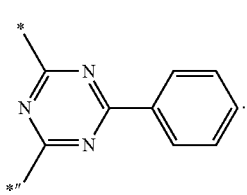

*, *', and *'' in Formulae 4-1 to 4-60 each indicate a binding site to a neighboring atom.

$R_1$ in Formula 1 may be a group represented by Formula 2-1 or a group represented by Formula 2-2.

For example, the group represented by Formula 2-1 may be a group represented by Formula 2-1A, but embodiments of the present disclosure are not limited thereto:

Formula 2-1A

In Formula 2-1A, $L_3$, $L_4$, a3, a4, $R_3$, $R_4$, and b4 are the same as described above, and * indicates a binding site to a neighboring atom.

In one embodiment, in Formulae 1, 2-1, and 2-2, $R_2$ to $R_5$ may each independently be selected from:

a group represented by Formula 2-3, a group represented by Formula 2-4, hydrogen, deuterium, —F, —Cl, —Br, —I, a hydroxyl group, a cyano group, a nitro group, an amidino group, a hydrazino group, a hydrazono group, $Si(Q_1)(Q_2)(Q_3)$, a $C_1$-$C_{20}$ alkyl group, a $C_3$-$C_{10}$ cycloalkyl group, a $C_1$-$C_{10}$ heterocycloalkyl group, a $C_1$-$C_{20}$ alkoxy group, and a $C_3$-$C_{20}$ cycloalkoxy group;

a $C_1$-$C_{20}$ alkyl group, a $C_3$-$C_{10}$ cycloalkyl group, a $C_1$-$C_{10}$ heterocycloalkyl group, a $C_1$-$C_{20}$ alkoxy group, and a $C_3$-$C_{20}$ cycloalkoxy group, each substituted with at least one selected from deuterium, —F, —Cl, —Br, —I, a hydroxyl group, a cyano group, a nitro group, an amidino group, a hydrazino group, and a hydrazono group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{20}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group and —Si($Q_{31}$)($Q_{32}$)($Q_{33}$), and $Q_1$ to $Q_3$ and $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

In one embodiment, $R_2$ to $R_5$ may each independently be selected from:

a group represented by Formula 2-3, a group represented by Formula 2-4, hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, a triazinyl group, and —Si($Q_1$)($Q_2$)($Q_3$); and a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, a triazinyl group, and —Si($Q_{31}$)($Q_{32}$)($Q_{33}$), and $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, $R_2$ to $R_5$ may each independently be selected from a group represented by Formula 2-3, a group represented by Formula 2-4, hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, an anthracenyl group, a carbazolyl group, a dibenzofuranyl group, a dibenzothiophenyl group, a pyridinyl group, a pyrazinyl group, a pyrimidinyl group, a pyridazinyl group, a triazinyl group, and —Si($Q_1$)($Q_2$)($Q_3$); and a $C_1$-$C_{20}$ alkyl group, a $C_3$-$C_{10}$ cycloalkyl group, a $C_1$-$C_{20}$ alkoxy group, a phenyl group, a biphenyl group, a terphenyl group, a naphthyl group, an anthracenyl group, a carbazolyl group, a dibenzofuranyl group, a dibenzothiophenyl group, a pyridinyl group, a pyrazinyl group, a pyrimidinyl group, a pyridazinyl group, and a triazinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, an anthracenyl group, a carbazolyl group, a dibenzofuranyl group, a dibenzothiophenyl group, a pyridinyl group, a pyrazinyl group, a pyrimidinyl group, a pyridazinyl group, a triazinyl group, and —Si($Q_{31}$)($Q_{32}$)($Q_{33}$), and $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In Formulae 1, 2-3, and 2-4, $R_6$ to $R_9$, $R_{11}$, and $R_{12}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, Si($Q_4$)($Q_5$)($Q_6$), —N($Q_4$)($Q_5$), —B($Q_4$)($Q_5$), —C(=O)($Q_4$), —S(=O)$_2$($Q_4$), and —P(=O)($Q_4$)($Q_5$), and $Q_4$ to $Q_6$ are the same as described above.

For example, $R_6$ to $R_9$, $R_{11}$, and $R_{12}$ may each independently be selected from:

hydrogen, deuterium, —F, —Cl, —Br, —I, a hydroxyl group, a cyano group, a nitro group, an amidino group, a hydrazino group, a hydrazono group, Si($Q_4$)($Q_5$)($Q_6$), a $C_1$-$C_{20}$ alkyl group, a $C_3$-$C_{10}$ cycloalkyl group, a $C_1$-$C_{10}$ heterocycloalkyl group, a $C_1$-$C_{20}$ alkoxy group, and a $C_3$-$C_{20}$ cycloalkoxy group;

a $C_1$-$C_{20}$ alkyl group, a $C_3$-$C_{10}$ cycloalkyl group, a $C_1$-$C_{10}$ heterocycloalkyl group, a $C_1$-$C_{20}$ alkoxy group, and a $C_3$-$C_{20}$ cycloalkoxy group, each substituted with at least one selected from deuterium, —F, —Cl, —Br, —I, a hydroxyl group, a cyano group, a nitro group, an amidino group, a hydrazino group, and a hydrazono group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{20}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, and —Si($Q_{31}$)($Q_{32}$)($Q_{33}$), and $Q_4$ to $Q_6$ and $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

In one embodiment, $R_6$ to $R_9$, $R_{11}$, and $R_{12}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, a triazinyl group, and —Si($Q_4$)($Q_5$)($Q_6$); and a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, a triazinyl group and —Si($Q_{31}$)($Q_{32}$)($Q_{33}$), and $Q_4$ to $Q_6$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, $R_6$ to $R_9$, $R_{11}$, and $R_{12}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, an anthracenyl group, a carbazolyl group, a dibenzofuranyl group, a dibenzothiophenyl group, a pyridinyl group, a pyrazinyl group, a pyrimidinyl group, a pyridazinyl group, a triazinyl group and —Si($Q_4$)($Q_5$)($Q_6$); and a $C_1$-$C_{20}$ alkyl group, a $C_3$-$C_{10}$ cycloalkyl group, a $C_1$-$C_{20}$ alkoxy group, a phenyl group, a biphenyl group, a terphenyl group, a naphthyl group, an anthracenyl group, a carbazolyl group, a dibenzofuranyl group, a dibenzothiophenyl group, a pyridinyl group, a pyrazinyl group, a pyrimidinyl group, a pyridazinyl group, and a triazinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, an anthracenyl group, a carbazolyl group, a dibenzofuranyl group, a dibenzothiophenyl group, a pyridinyl group, a pyrazinyl group, a pyrimidinyl group, a pyridazinyl group, a triazinyl group and —Si($Q_{31}$)($Q_{32}$)($Q_{33}$), and $Q_4$ to $Q_6$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

b1 in Formula 1 may be an integer from 1 to 10. b1 indicates the number of *-($L_1$)$_{a1}$-$R_1$(s), wherein, when b1 is two or more, two or more *-($L_1$)$_{a1}$-$R_1$(s) may be identical to or different from each other.

In one embodiment, b1 may be an integer from 1 to 5.

In one or more embodiments, b1 may be 1, 2, or 3.

In one or more embodiments, b1 may be 1 or 2, but embodiments of the present disclosure are not limited thereto.

b2 in Formula 1 may be an integer from 1 to 10. b2 indicates the number of *-($L_2$)$_{a2}$-$R_2$(s), wherein, when b2 is two or more, two or more *-($L_2$)$_{a2}$-$R_2$(s) may be identical to or different from each other.

In one embodiment, b2 may be an integer from 1 to 5.

In one or more embodiments, b2 may be 1, 2, or 3.

In one or more embodiments, b2 may be 1 or 2, but embodiments of the present disclosure are not limited thereto.

b4 in Formula 2-1 may be an integer from 0 to 5. b4 indicates the number of *-($L_4$)$_{a4}$-$R_4$(s), wherein, when b4 is two or more, two or more *-($L_4$)$_{a4}$-$R_4$(s) may be identical to different from each other.

In one embodiment, b4 may be 0, 1, or 2.

In one or more embodiments, b4 may be 0 or 1, but embodiments of the present disclosure are not limited thereto.

b5 in Formula 2-2 may be an integer from 0 to 6. b5 indicates the number of *-($L_5$)$_{a5}$-$R_5$(s), wherein, when b5 is two or more, two or more *-($L_5$)$_{a5}$-$R_5$(s) may be identical to or different from each other.

In one embodiment, b5 may be 0, 1, 2, or 3.

In one or more embodiments, b5 may be 0, 1, or 2, but embodiments of the present disclosure are not limited thereto.

In one embodiment, the first compound may be represented by one of Formulae 1A to 1P:

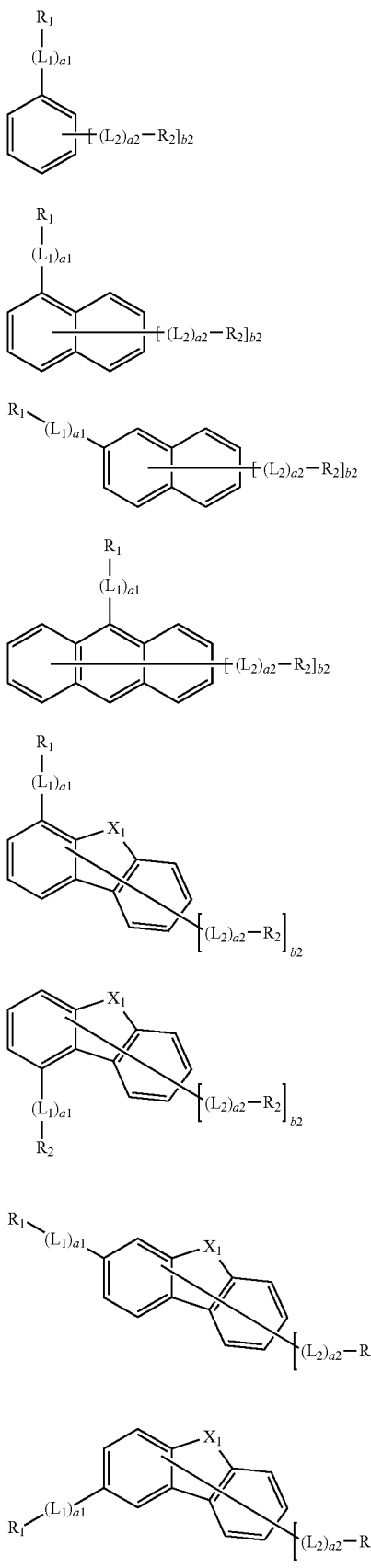
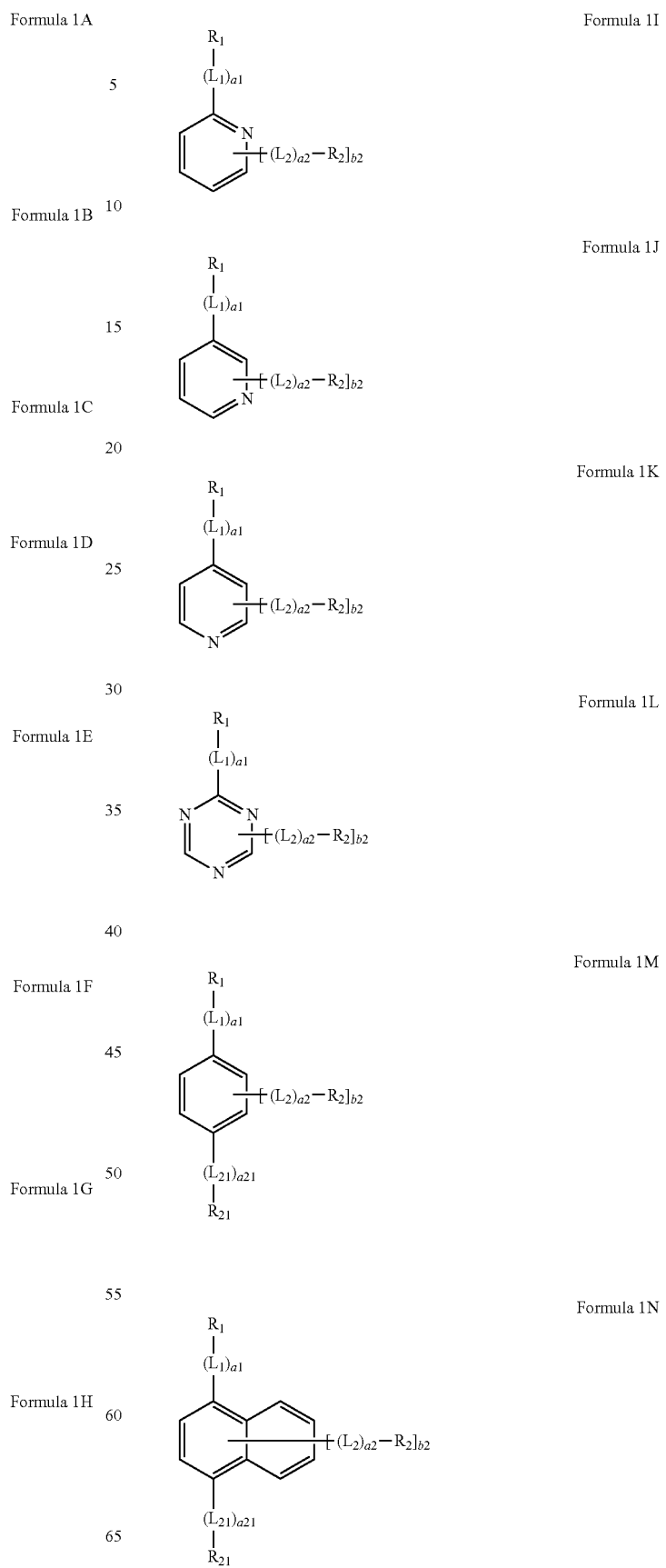

Formula 1O

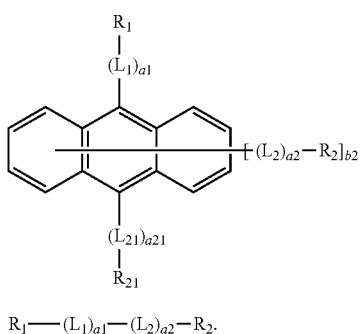

Formula 1P

R₁—(L₁)ₐ₁—(L₂)ₐ₂—R₂.

In Formulae 1A to 1P, $L_1$, $L_2$, a1, a2, $R_1$, $R_2$, and b2 are the same as described herein in connection with Formula 1, and $L_{21}$, a21, and $R_{21}$ are the same as described in connection with $L_1$, a1, and $R_1$, respectively.

For example, $L_1$, $L_2$, and $L_{21}$ in Formula 1A to 1P may each independently be selected from *—S—*', *—O—*', *—C(=O)—*', *—S(=O)—', *—S(=O)₂-', *—[C(Z₁)(Z₂)]ₙ₁—*', and groups represented by Formulae 3-1 to 3-75.

In one or more embodiments, $L_1$, $L_2$, and $L_{21}$ in Formulae 1A to 1P may each independently be selected from *—O—*', *—C(=O)—', *—CH₂—*', *—(CH₂)₂—*', *—(CH₂)₃—*', *—(CH₂)₄—*', *—(CH₂)₅—*', and groups represented by Formulae 4-1 to 4-58 and 4-60.

In one or more embodiments, $R_1$ and $R_{21}$ in Formulae 1A to 1P may each independently be a group represented by Formula 2-1A or a group represented by Formula 2-2.

In one or more embodiments, $R_1$ and $R_{21}$ in Formulae 1M to 1O may each be a group represented by Formula 2-1. For example, $R_1$ and $R_{21}$ in Formulae 1M to 1O may each be a group represented by Formula 2-1A.

In one or more embodiments, $R_1$ and $R_{21}$ in Formulae 1M to 1O may each be a group represented by Formula 2-2.

The first compound may be one of Compounds 1 to 205, but embodiments of the present disclosure are not limited thereto:

1

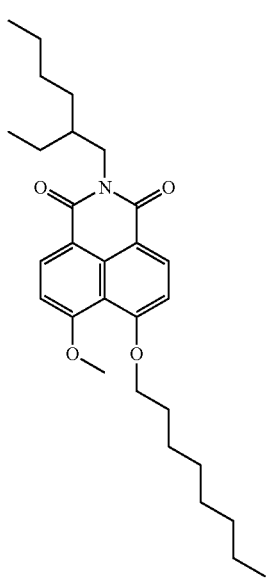

2

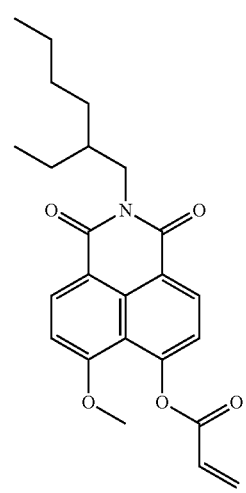

3

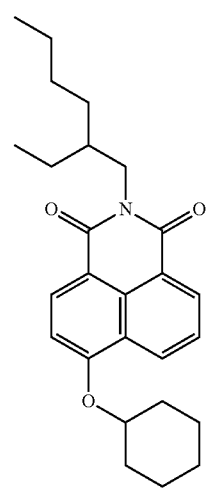

4

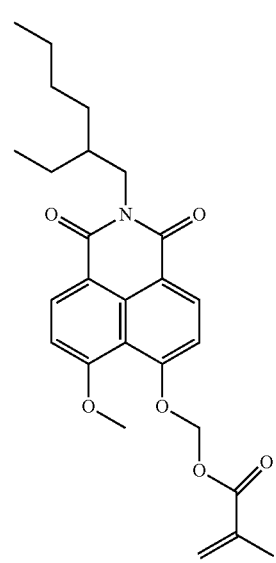

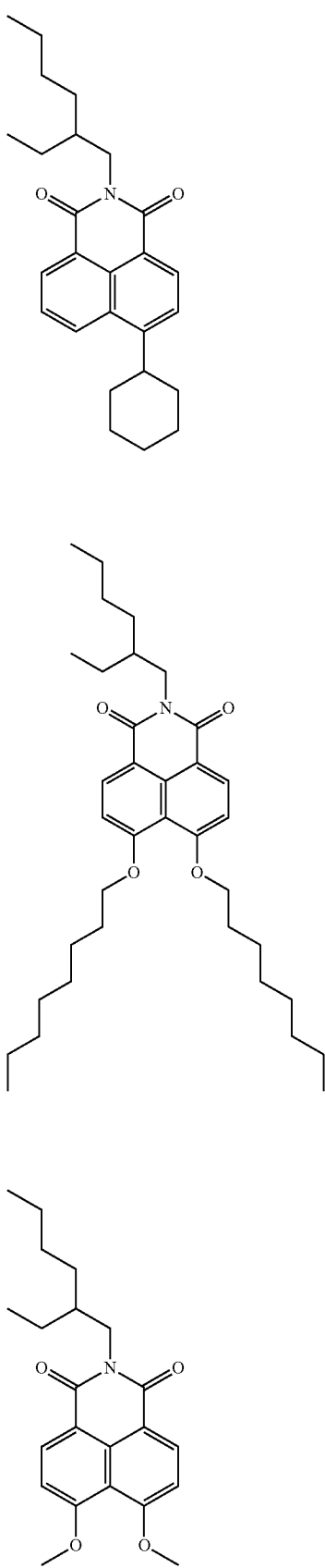
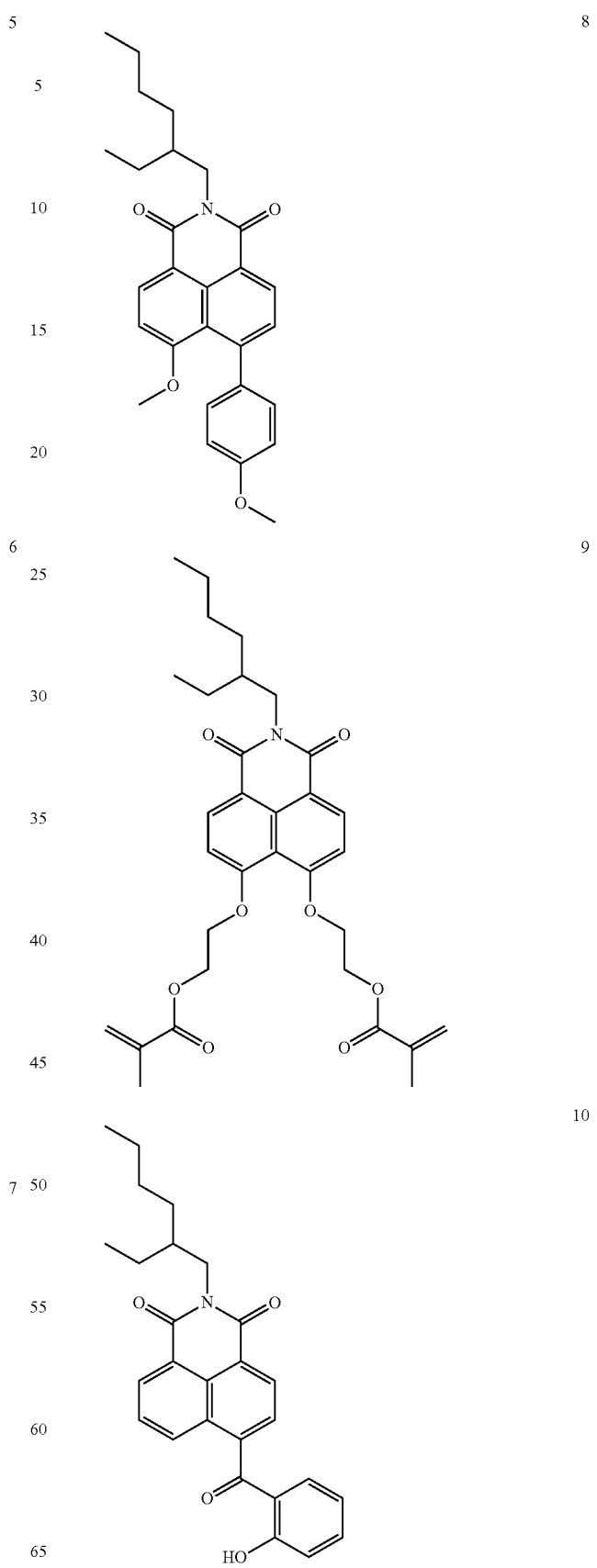

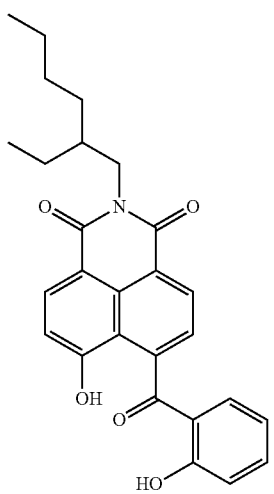
11
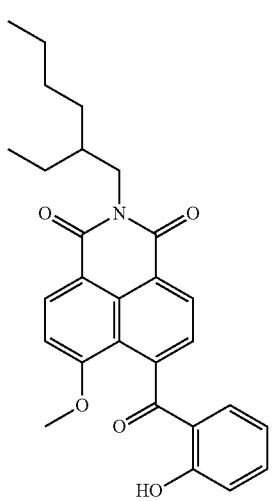
12
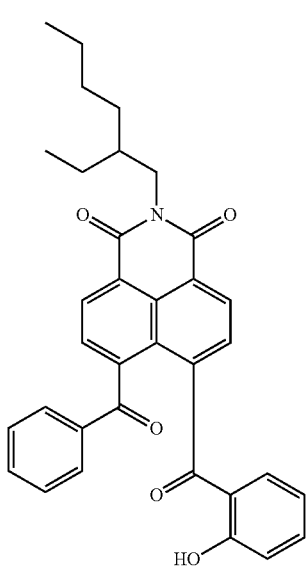
13
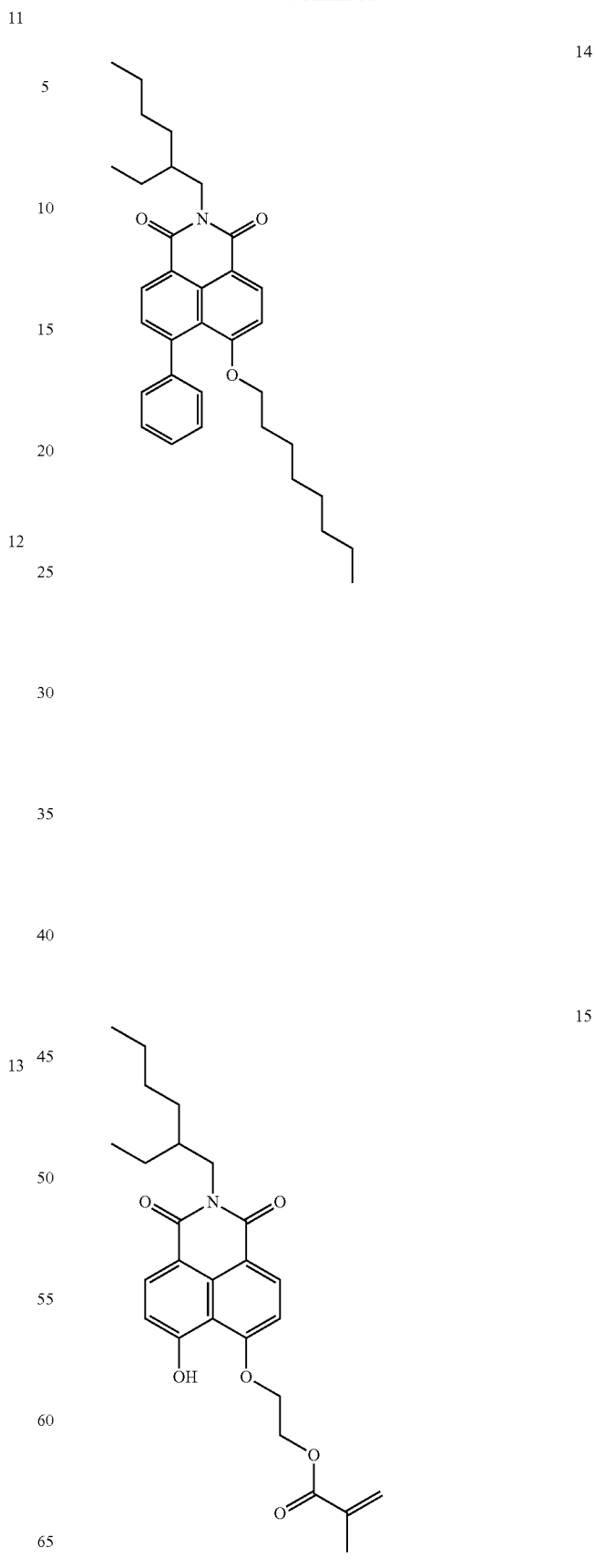

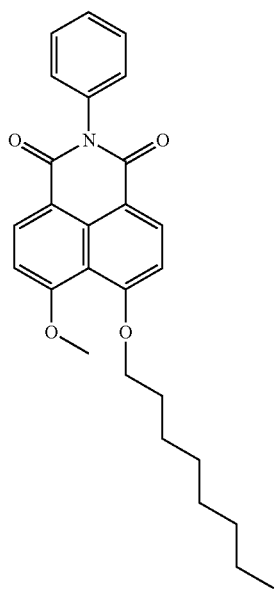
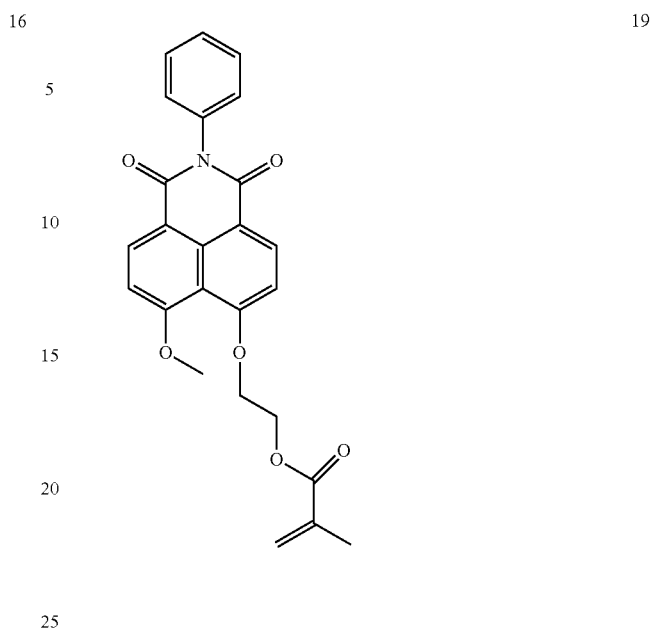
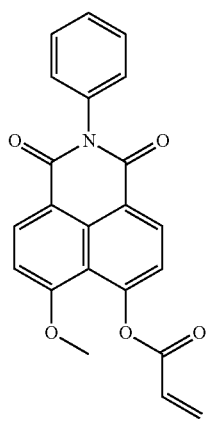
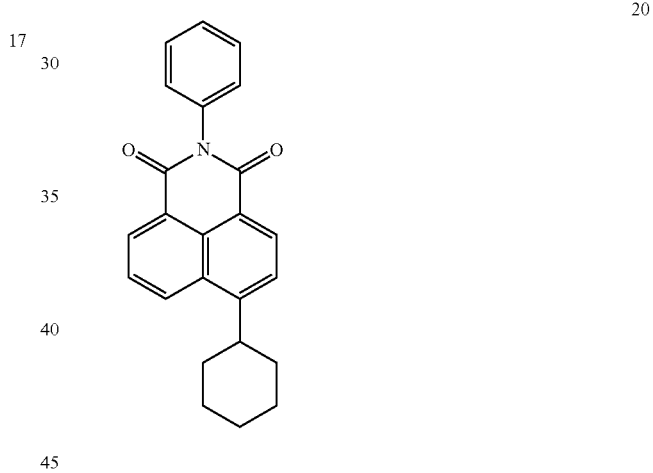
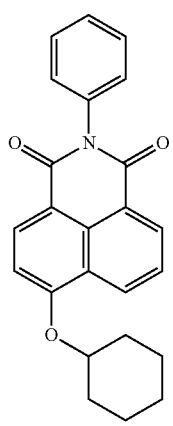
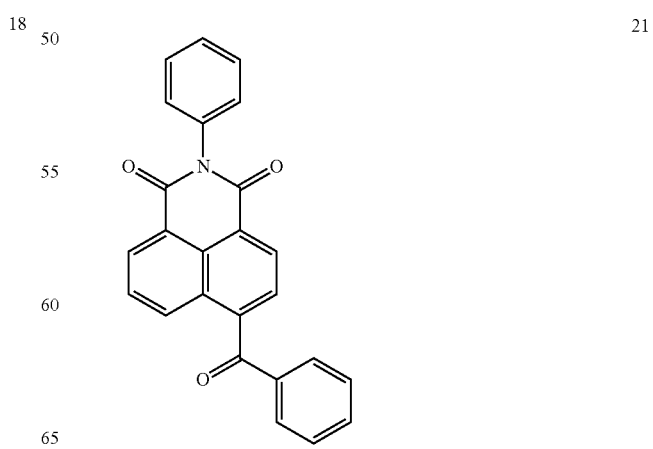

22
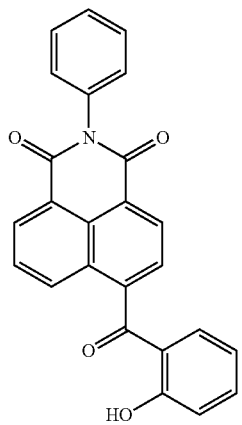
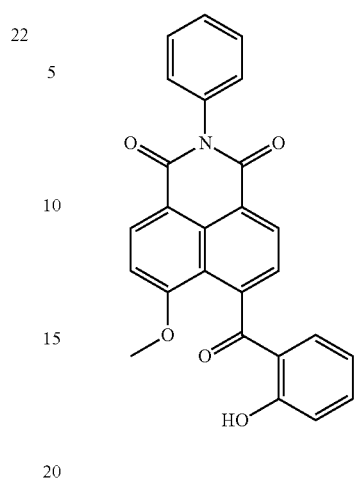
23
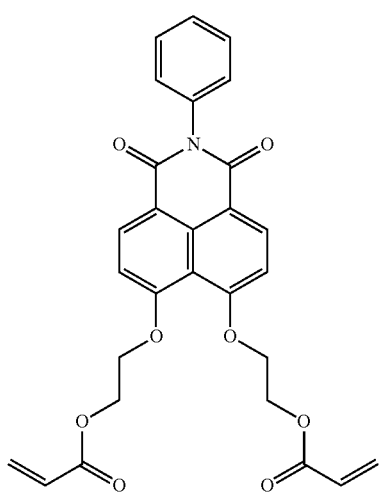
25
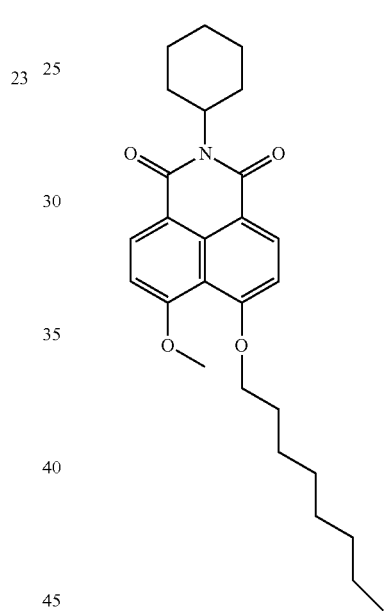
24
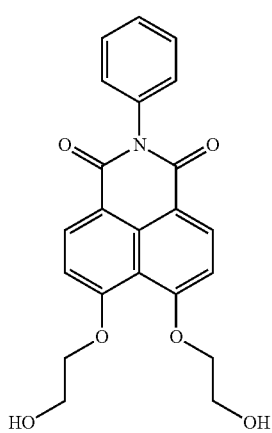
26
27
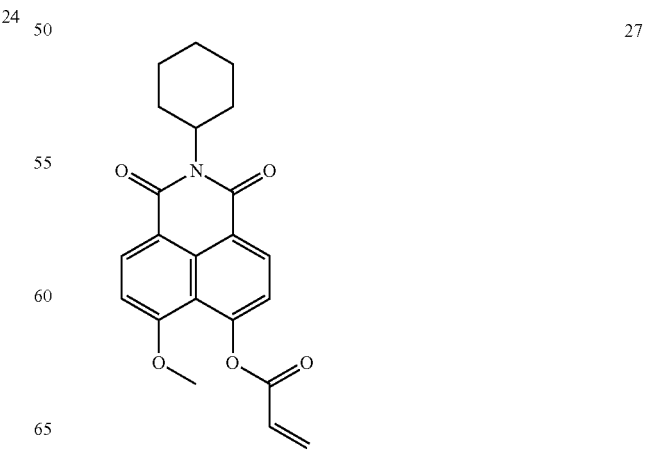

28
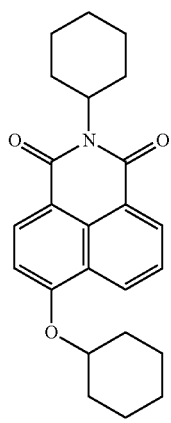
29
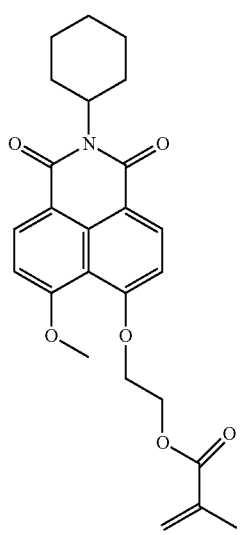
30
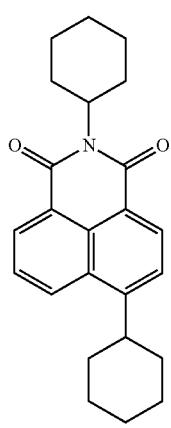
31
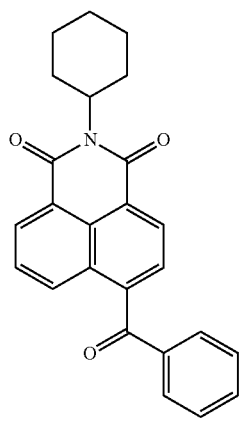
32
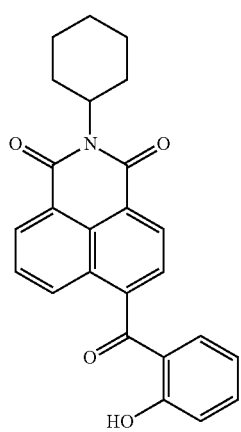
33
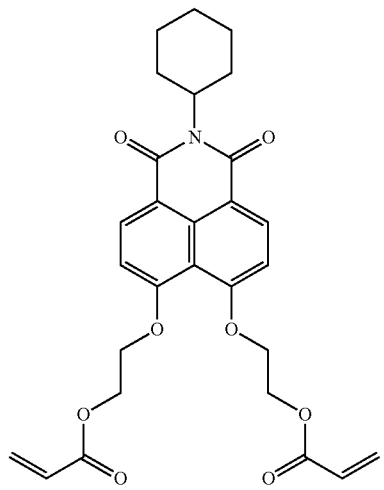

34
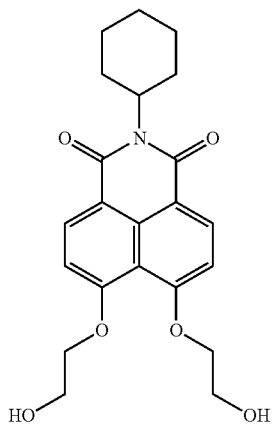
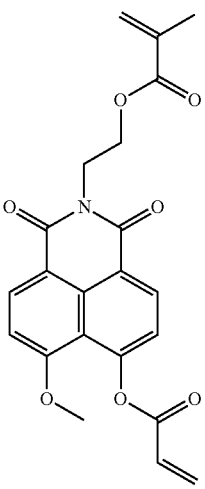
35
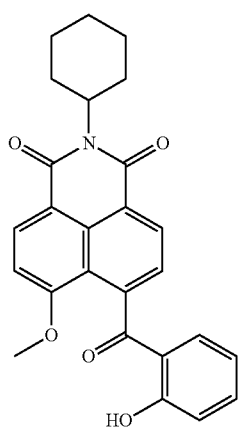
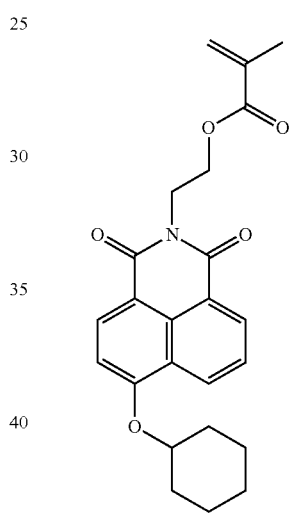
36
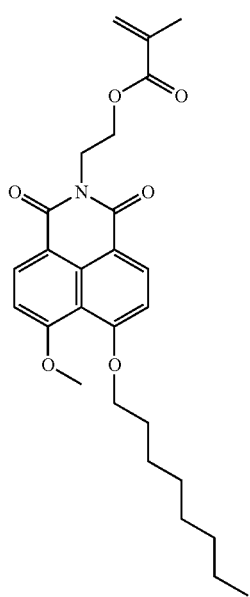
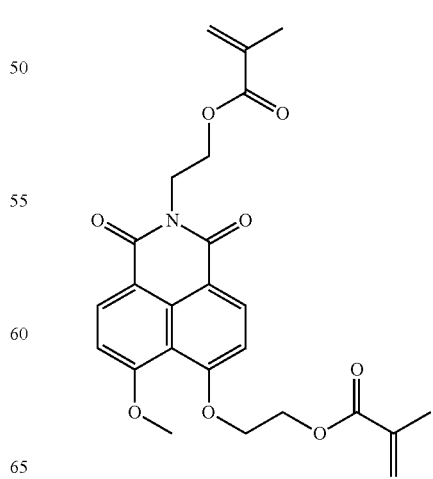

40
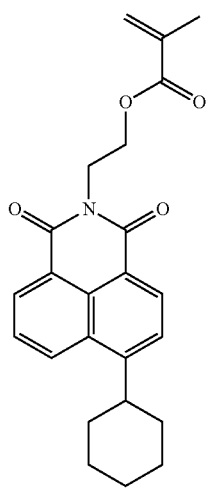
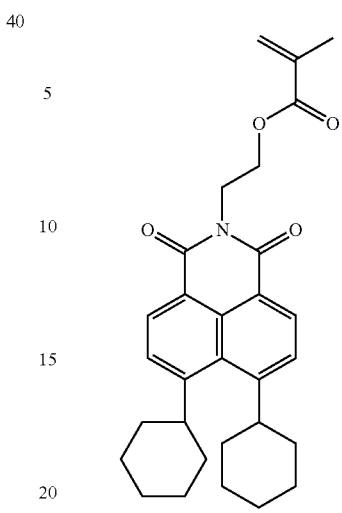
41
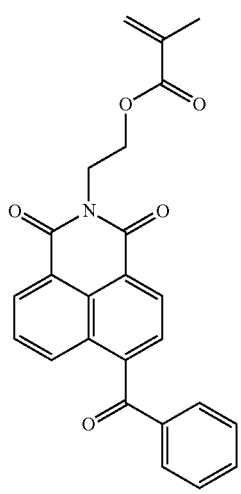
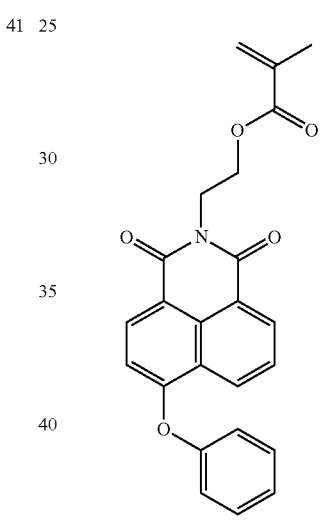
42
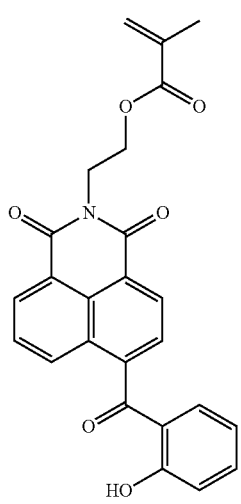
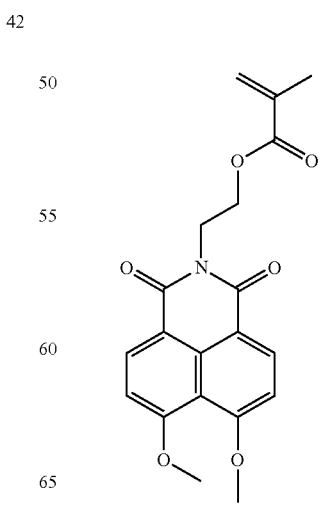

46
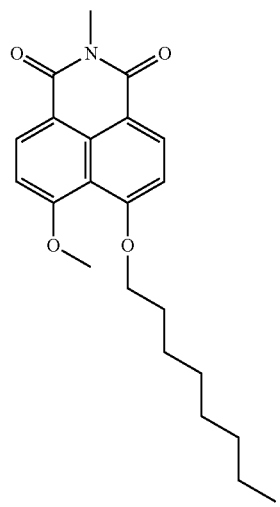
47
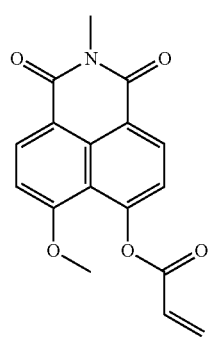
48
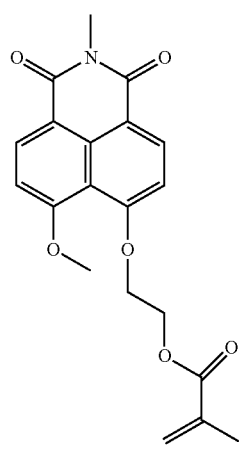
49
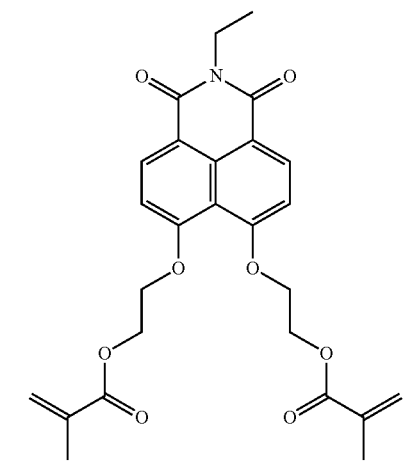
50
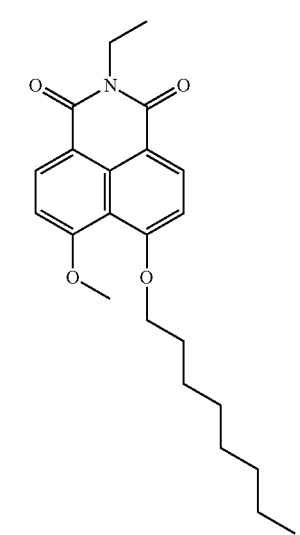
51

52
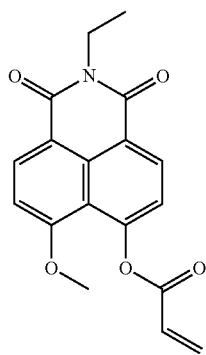
53
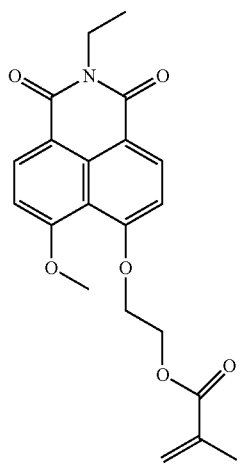
54
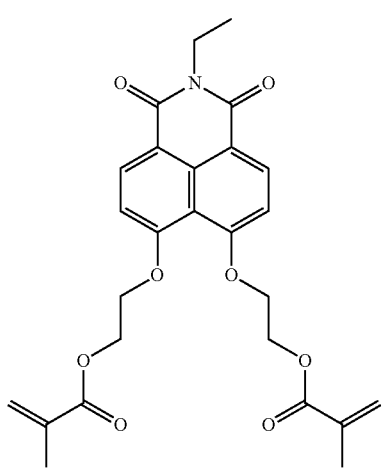
55
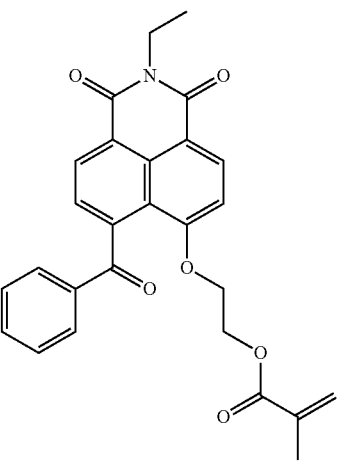
56
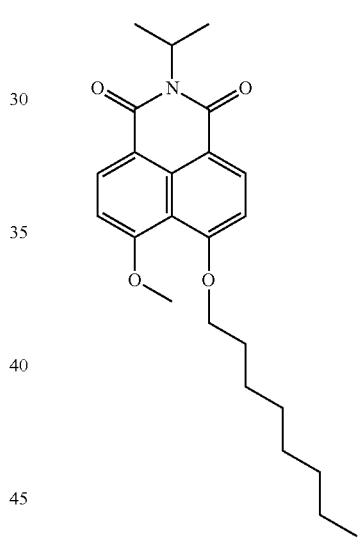
57
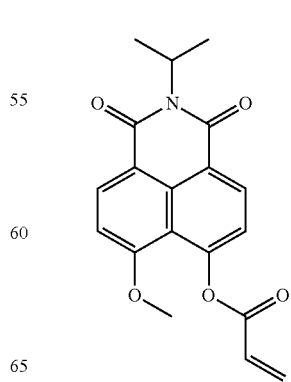

57
-continued
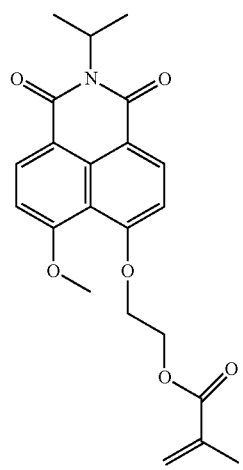
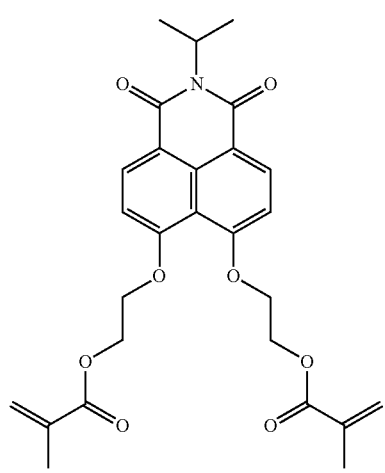
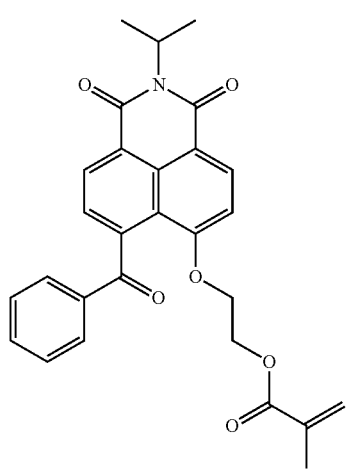
58
-continued
58
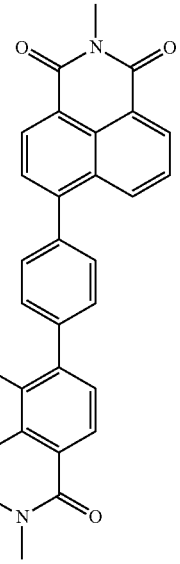
59
60
61
62
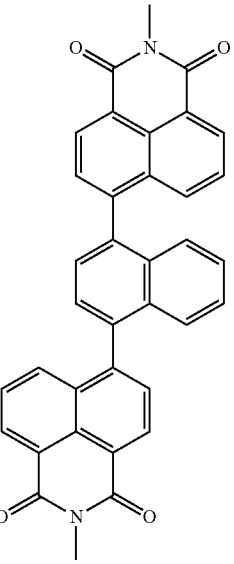

63
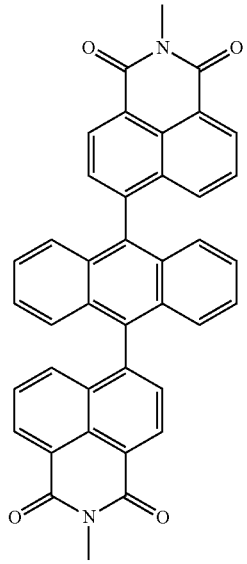
65
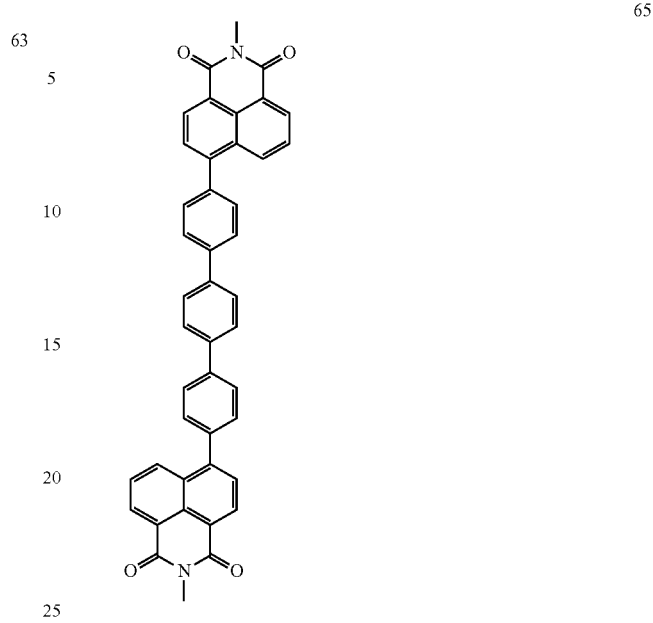
64
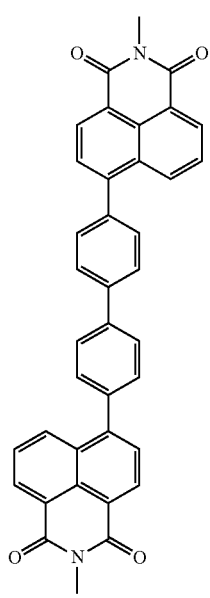
66
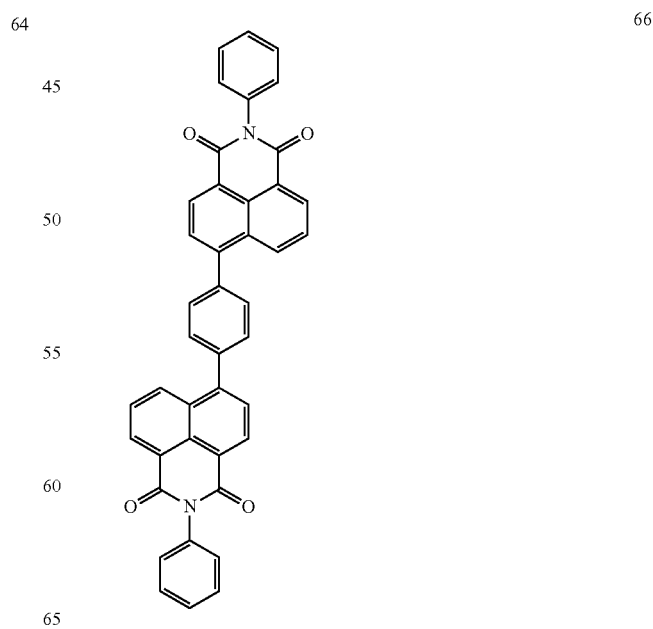

67
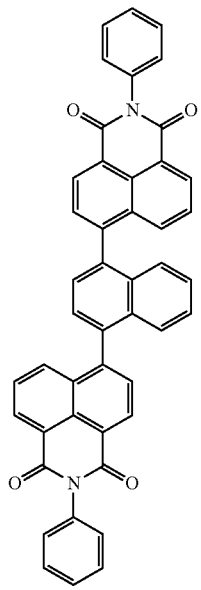
68
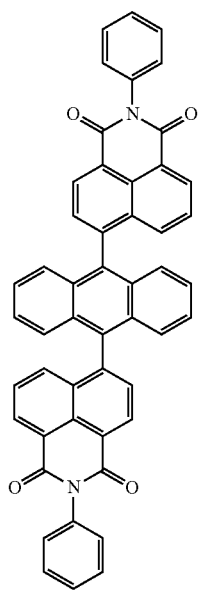
69
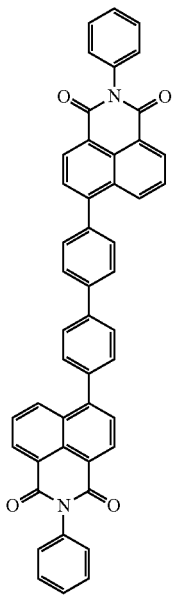
70
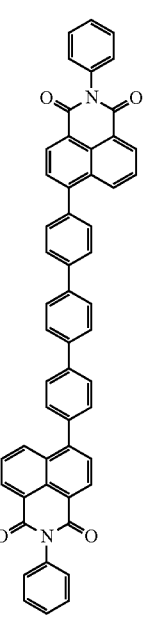

71
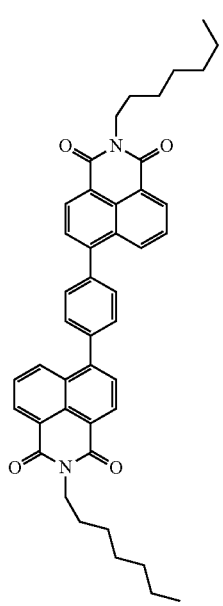
72
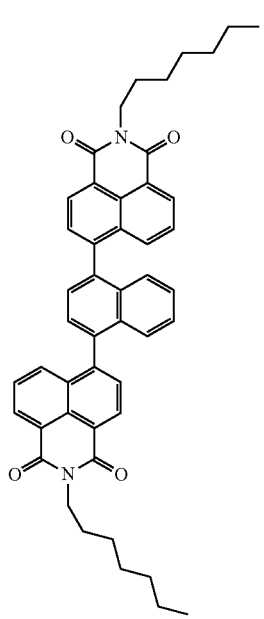
73
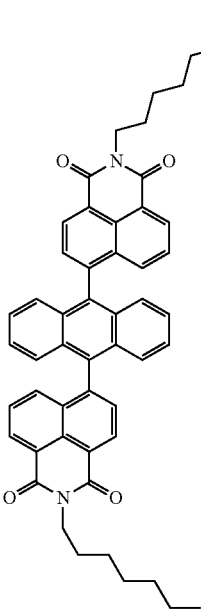
74
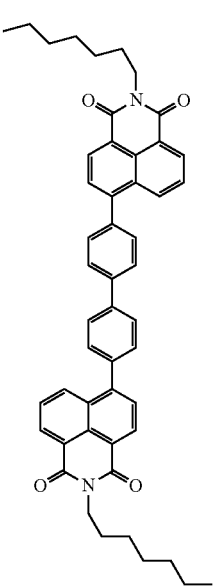

65
-continued
66
-continued
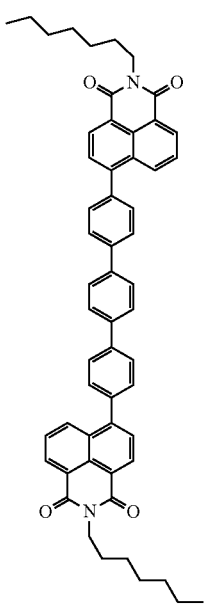
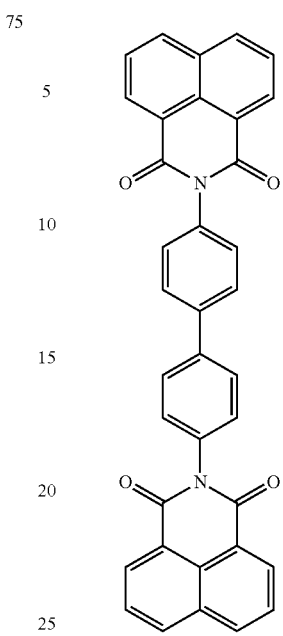
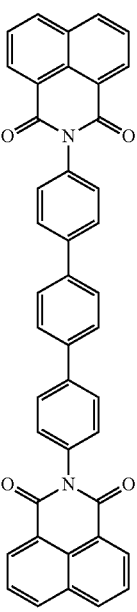

67
-continued
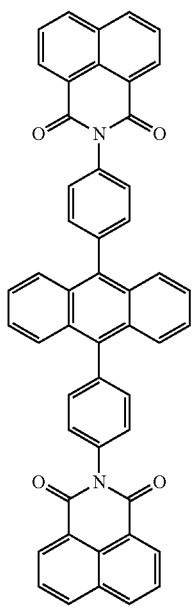
80
68
-continued
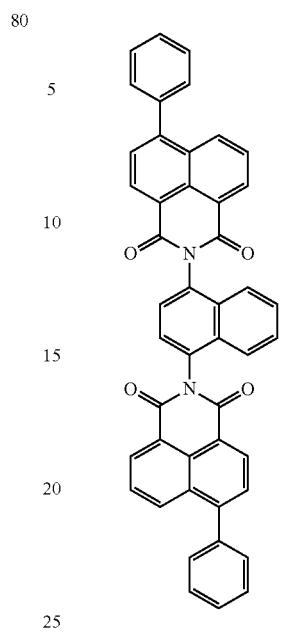
82
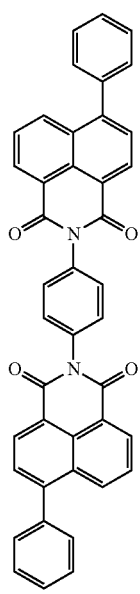
81
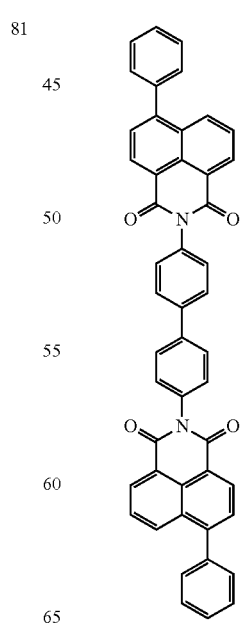
83

84
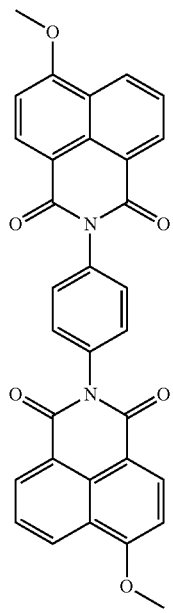
85
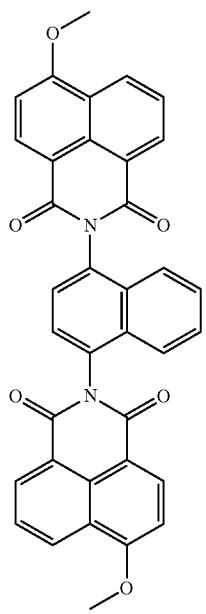
86
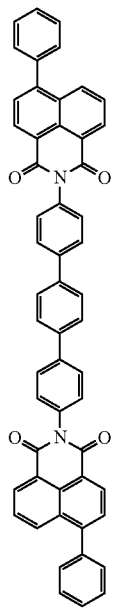
87
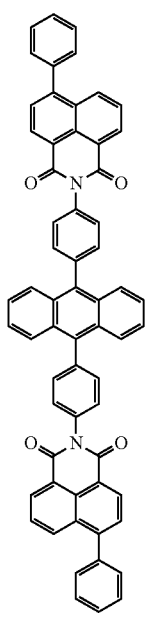

88
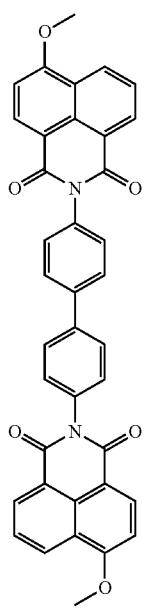
89
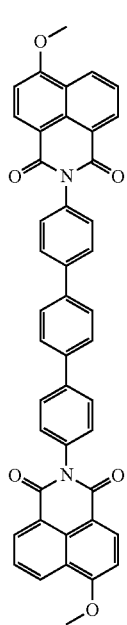
90
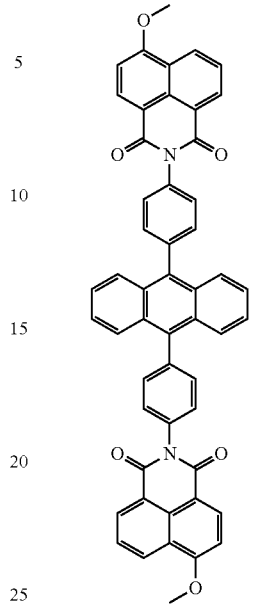
91
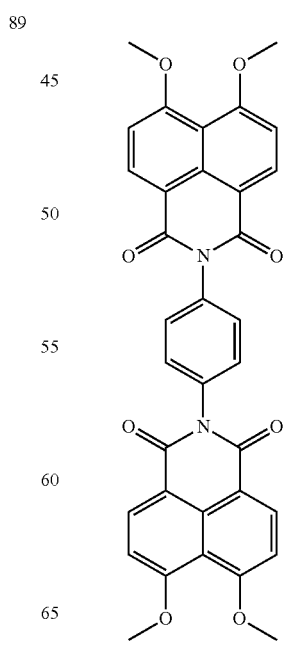

73
-continued
92
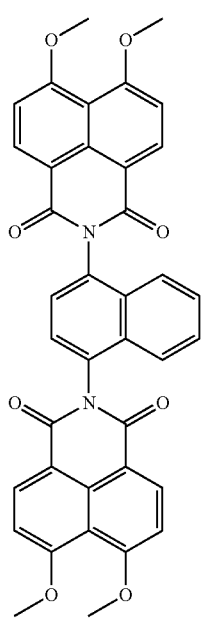
93
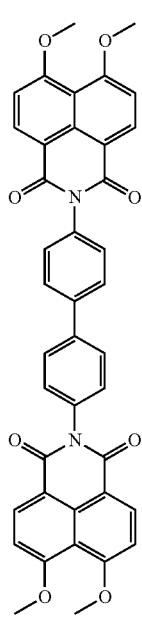
74
-continued
94
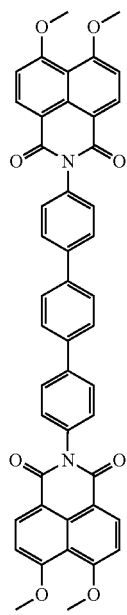
95
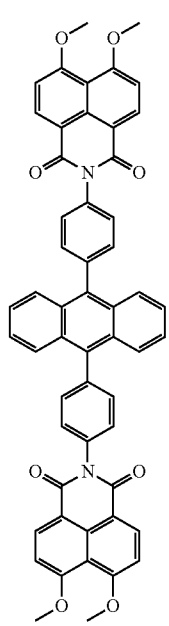

96
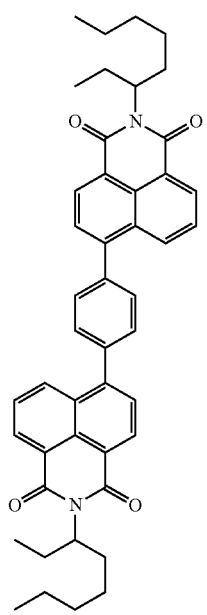
97
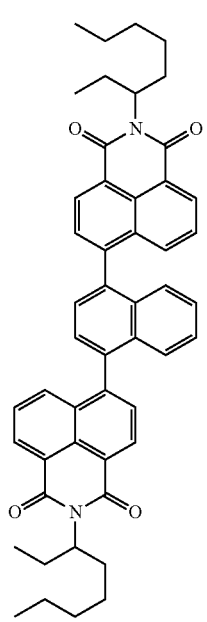
98
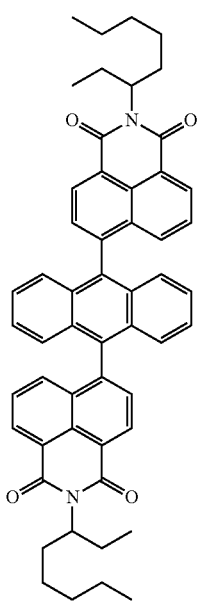
99
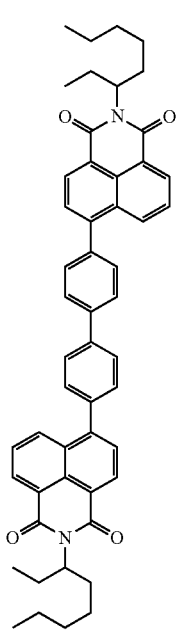

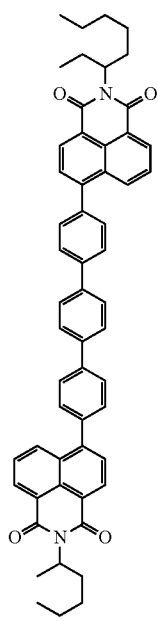
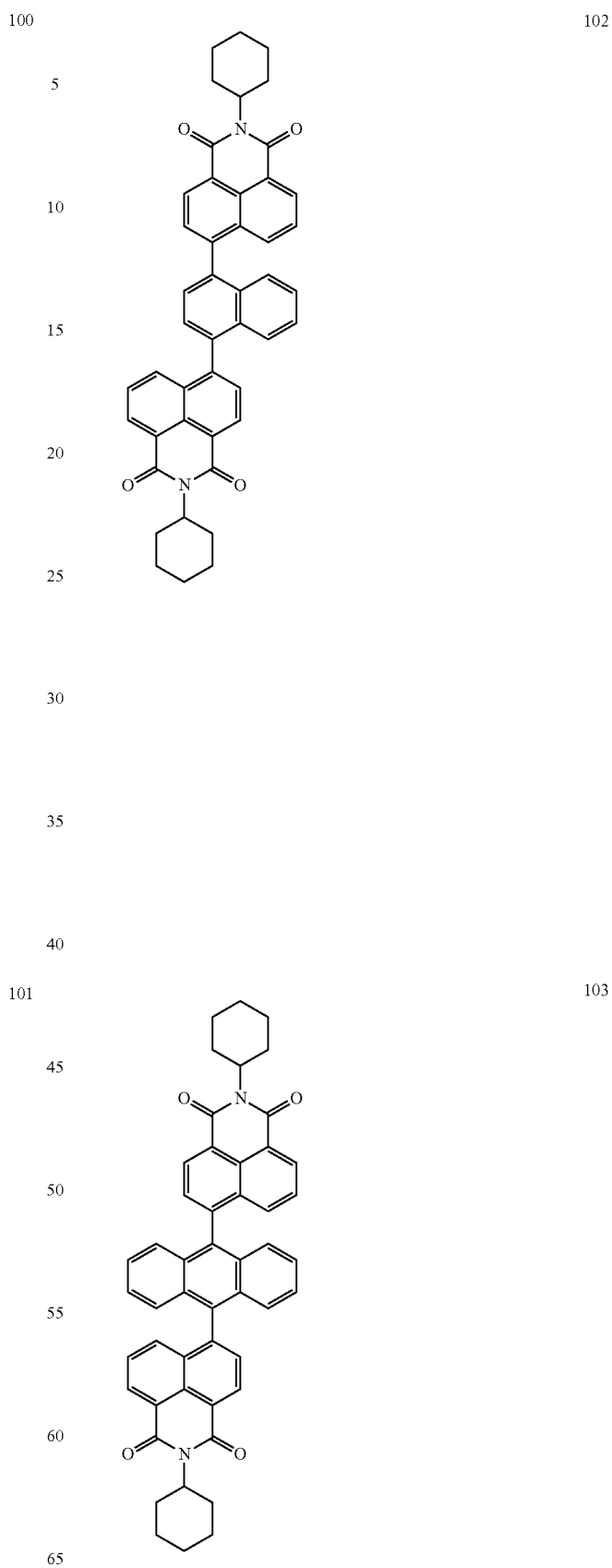

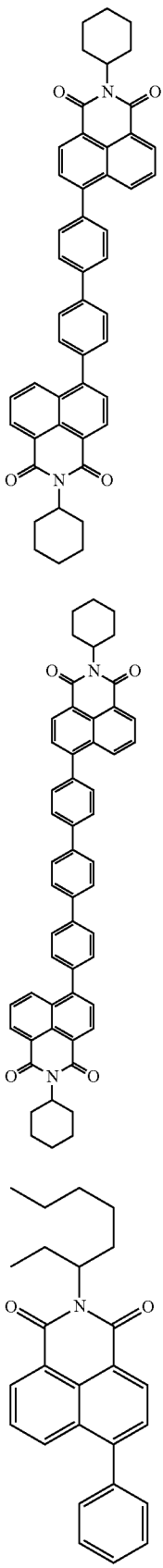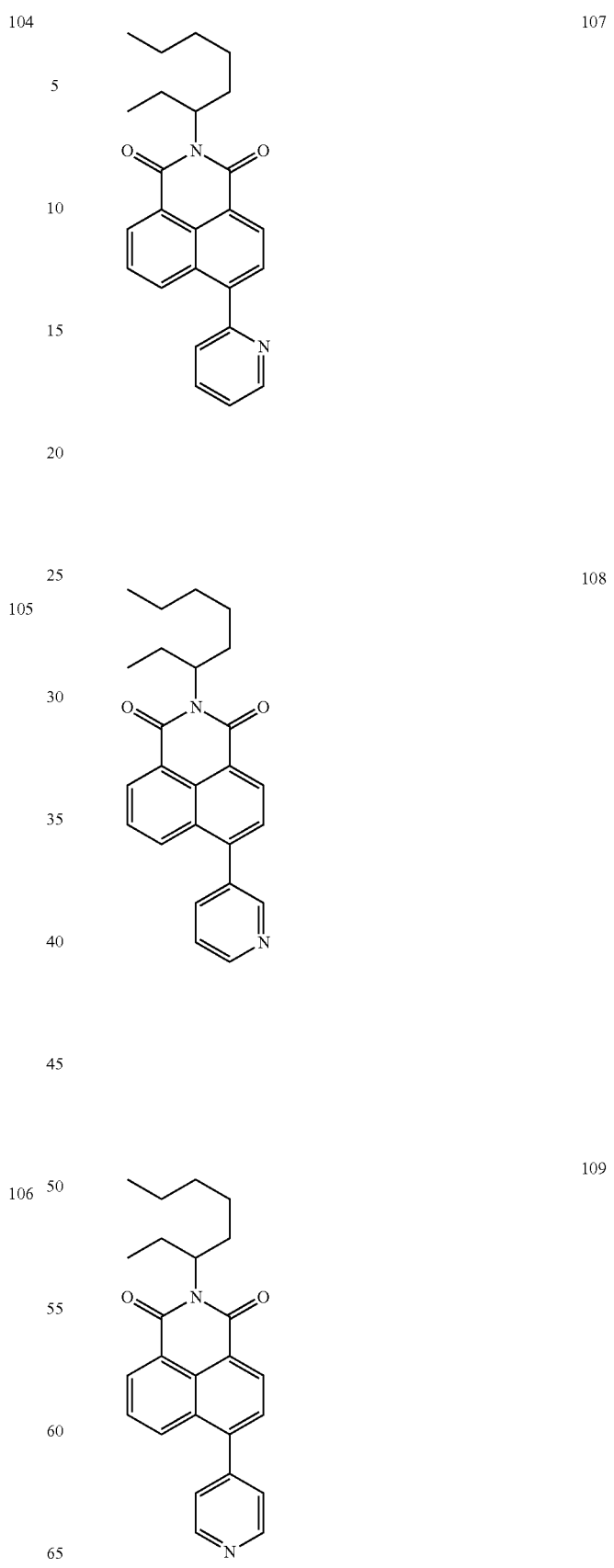

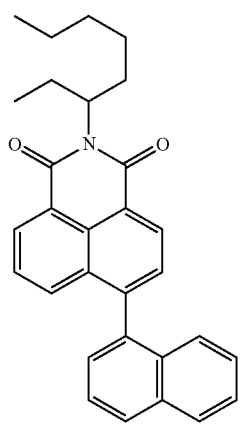
110
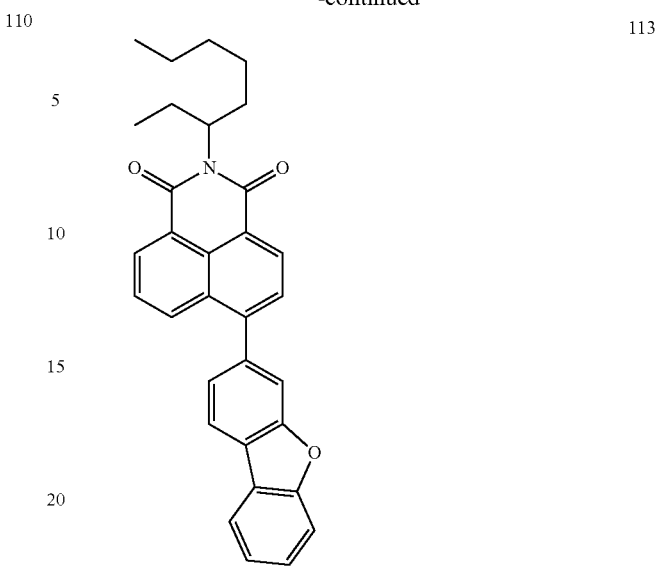
113
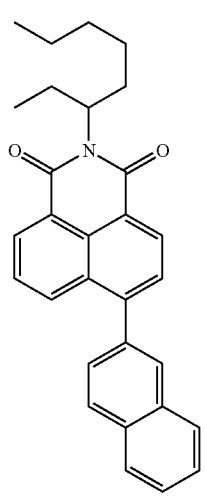
111
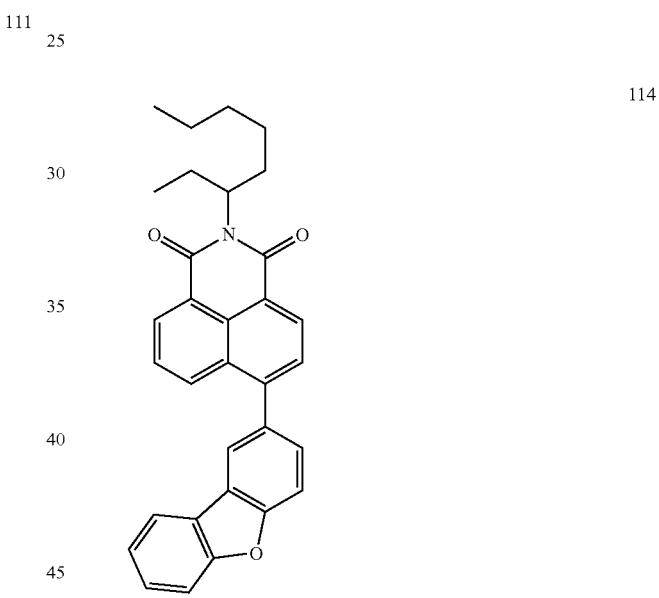
114
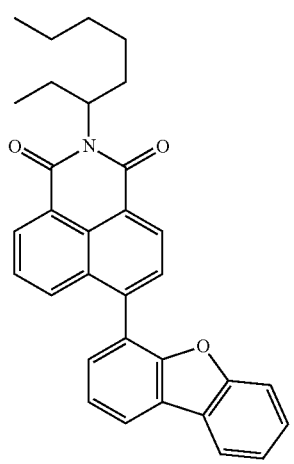
112
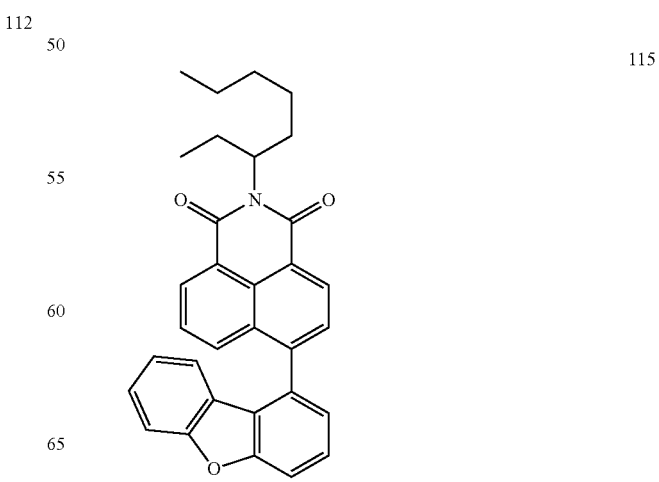
115

83
-continued
116
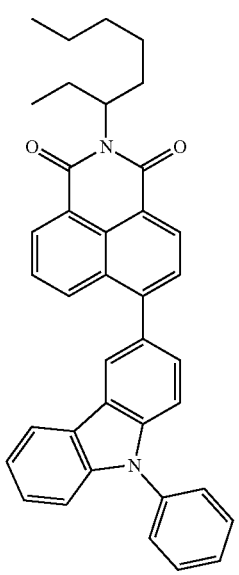
117
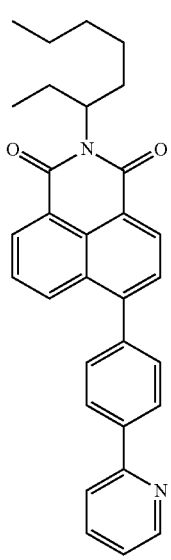
118
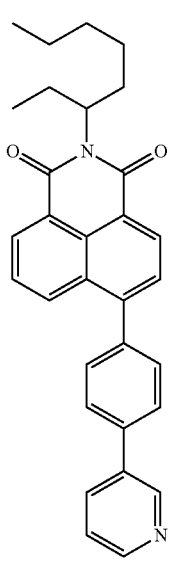
84
-continued
119
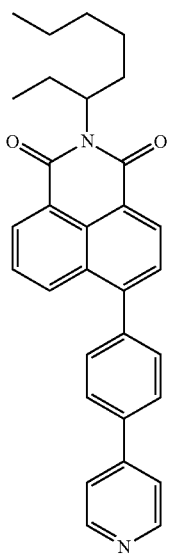
120
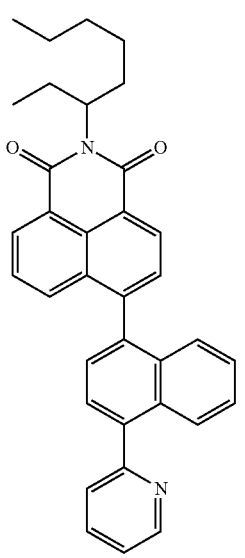
121
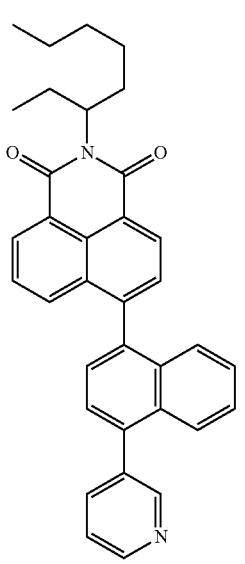

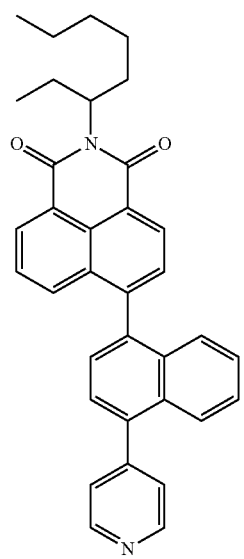
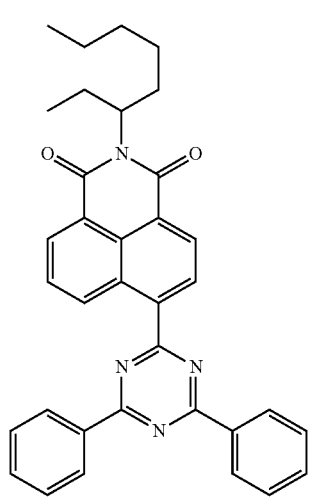
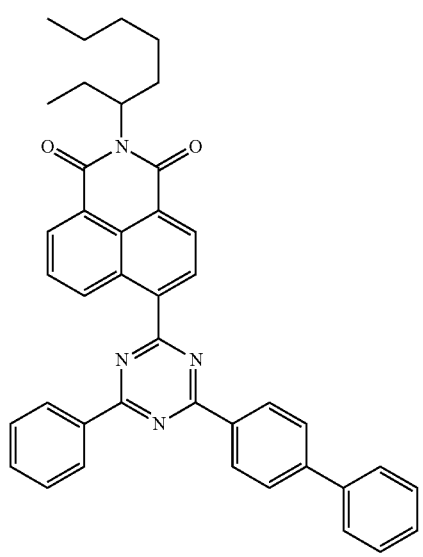
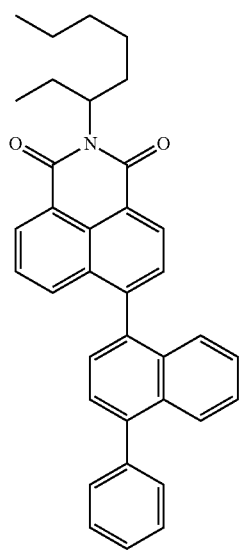
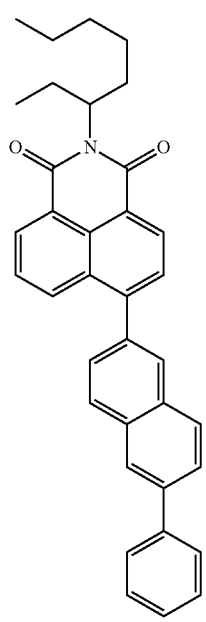

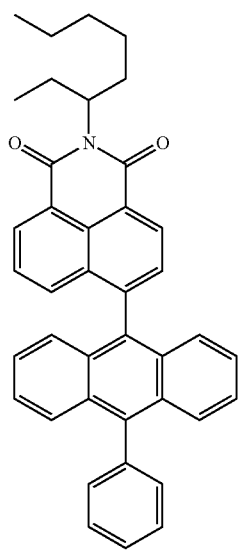
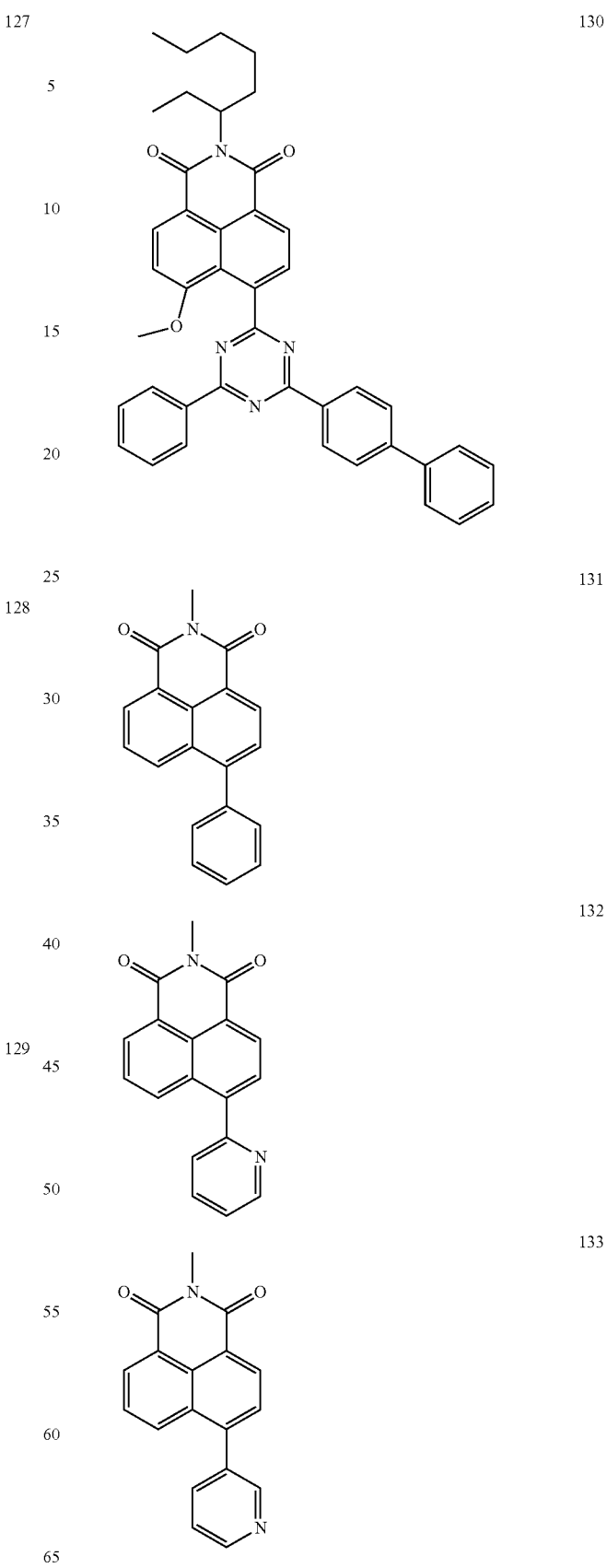

134 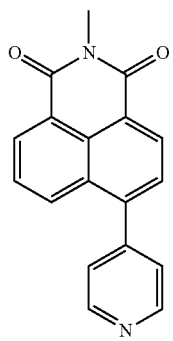
135 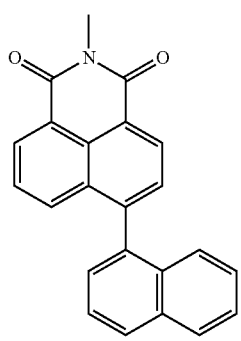
136 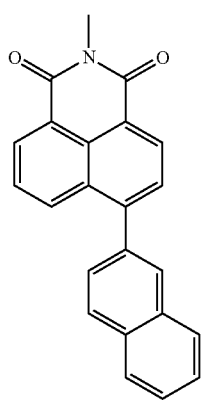
137 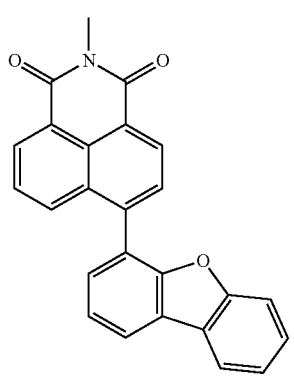
138 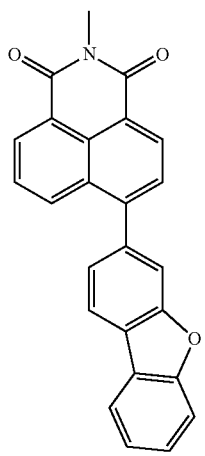
139 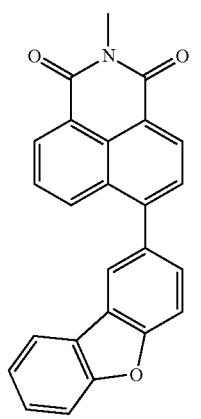
140 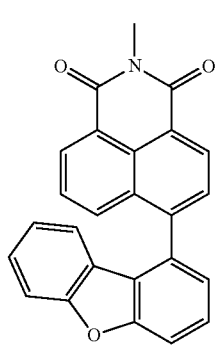

91
-continued
92
-continued
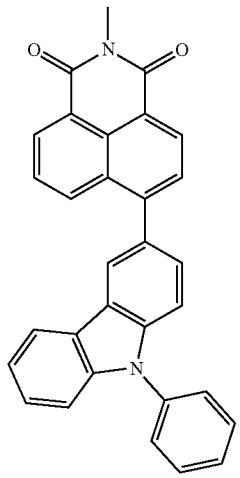
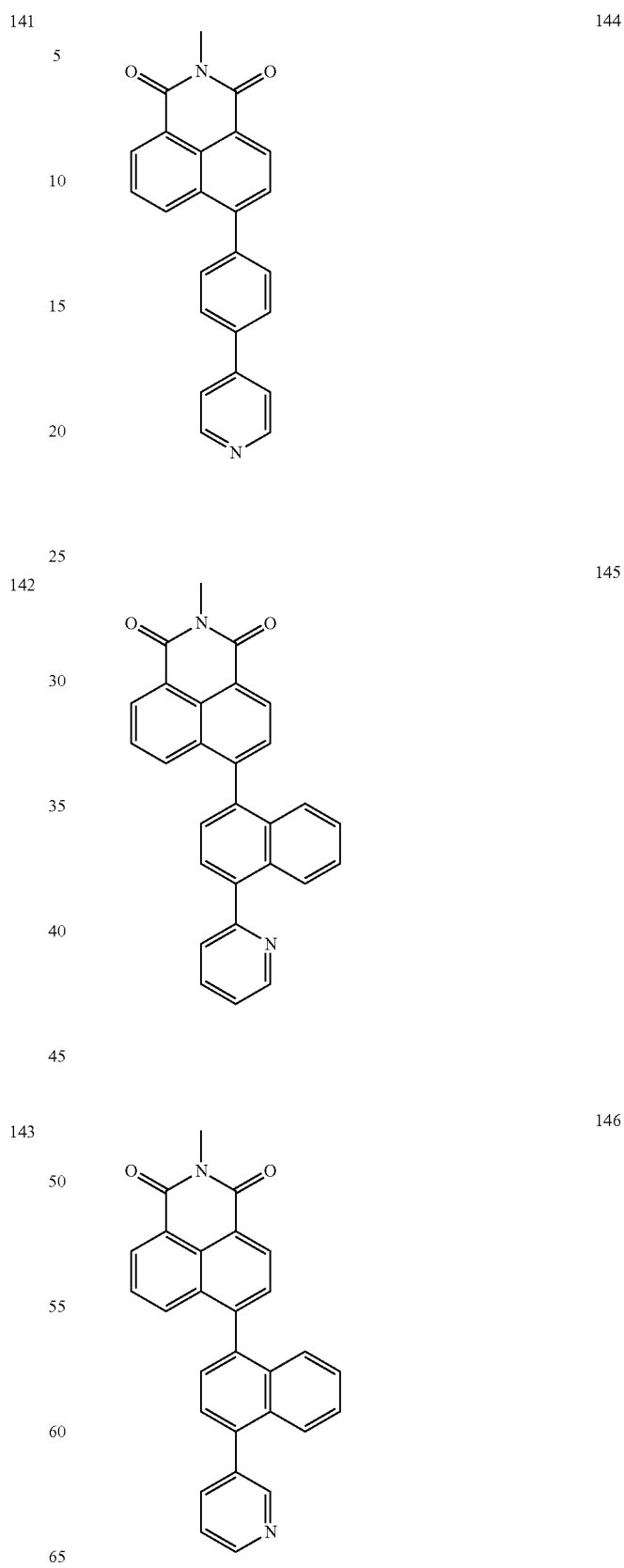

93
-continued
147
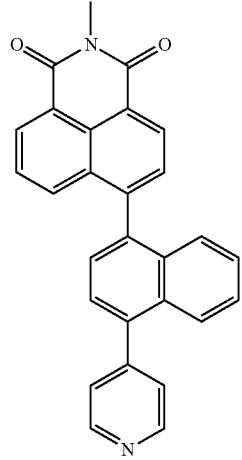
148
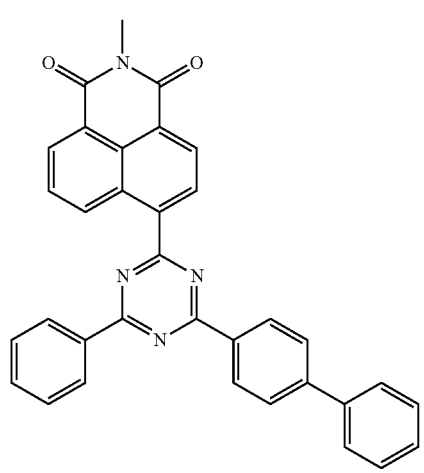
149
94
-continued
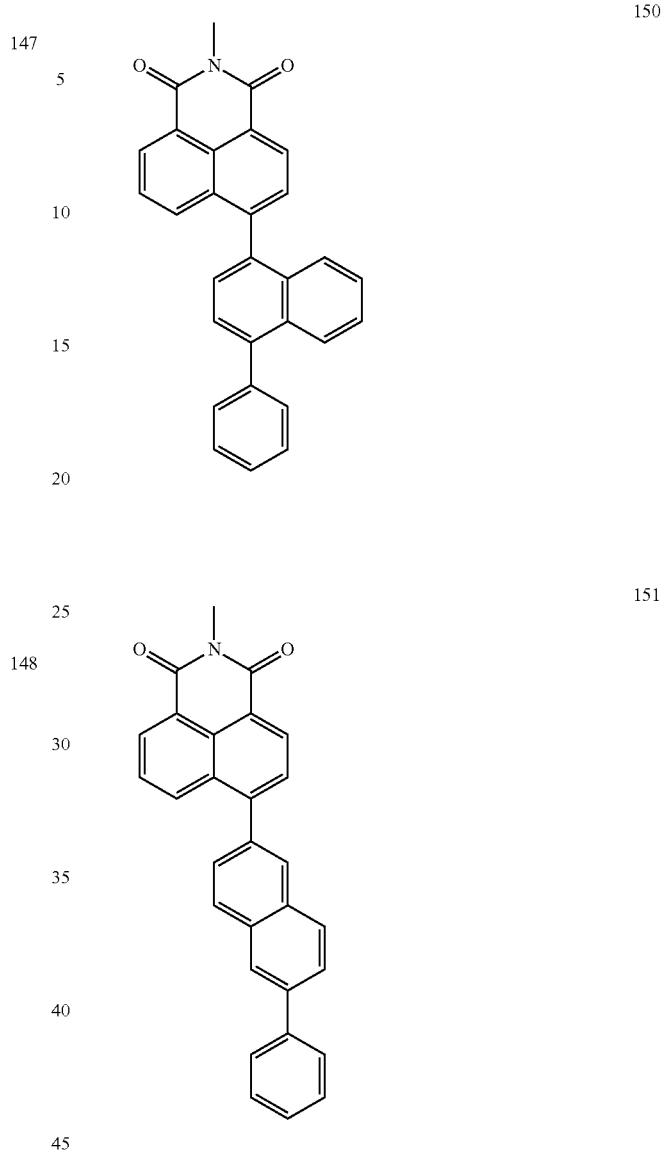
150
151
152
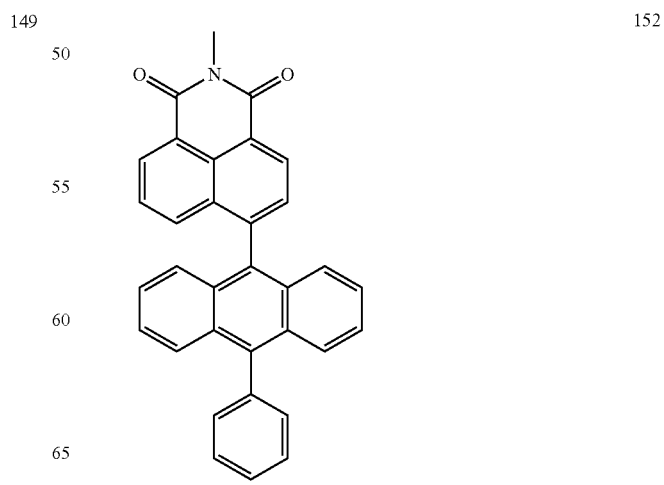

95
-continued
153
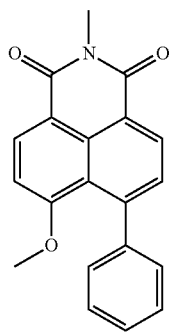
154
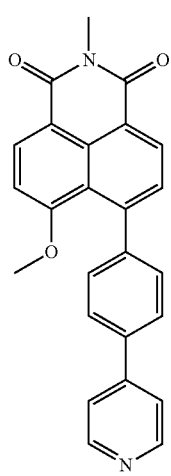
155
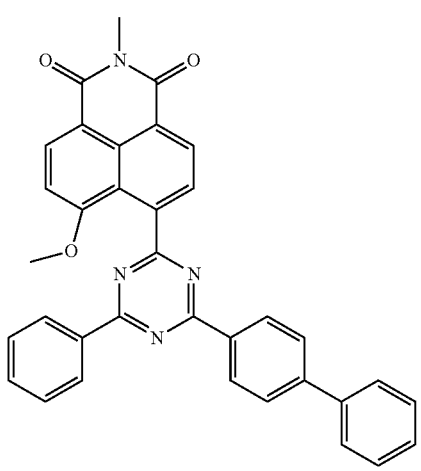
96
-continued
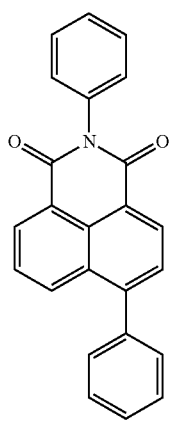
156
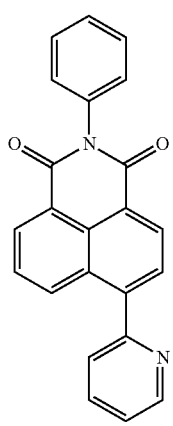
157
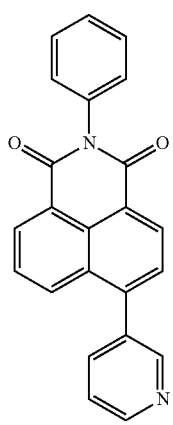
158

159
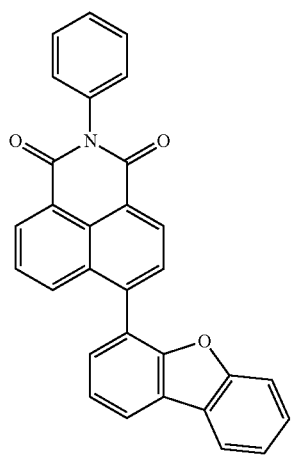
162
160
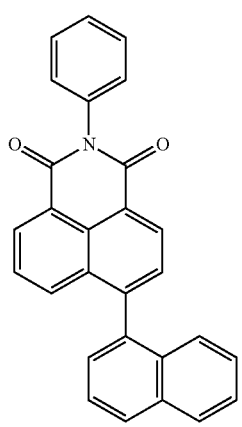
163
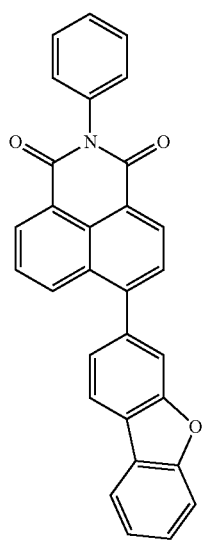
161
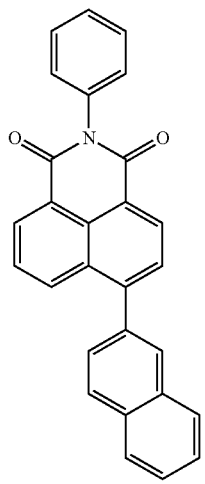
164
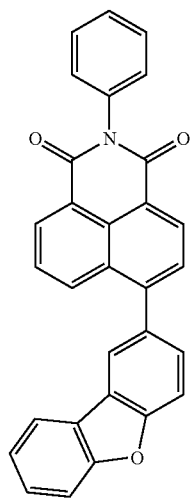

165
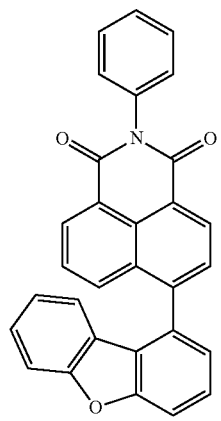
166
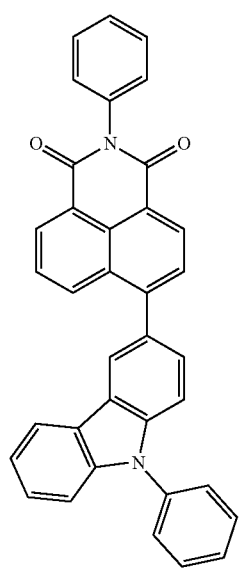
167
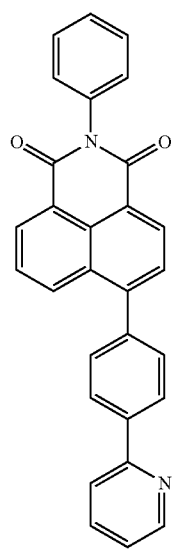
168
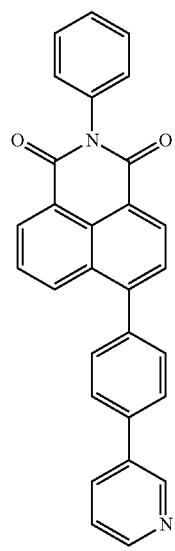
169
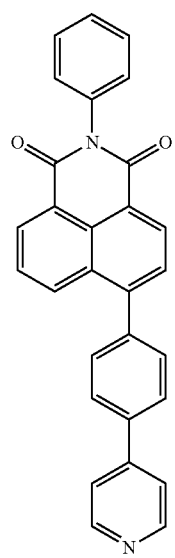
170
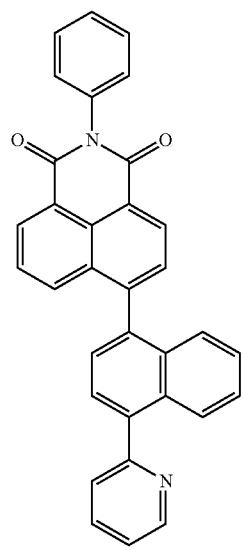

101
-continued
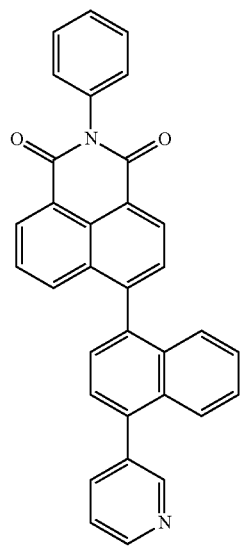
171
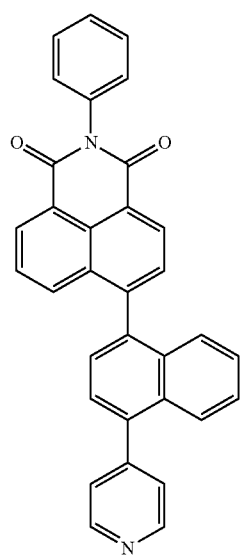
172
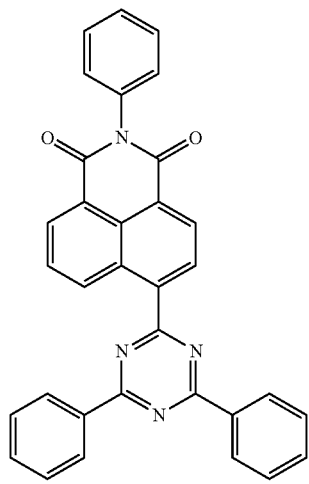
173
102
-continued
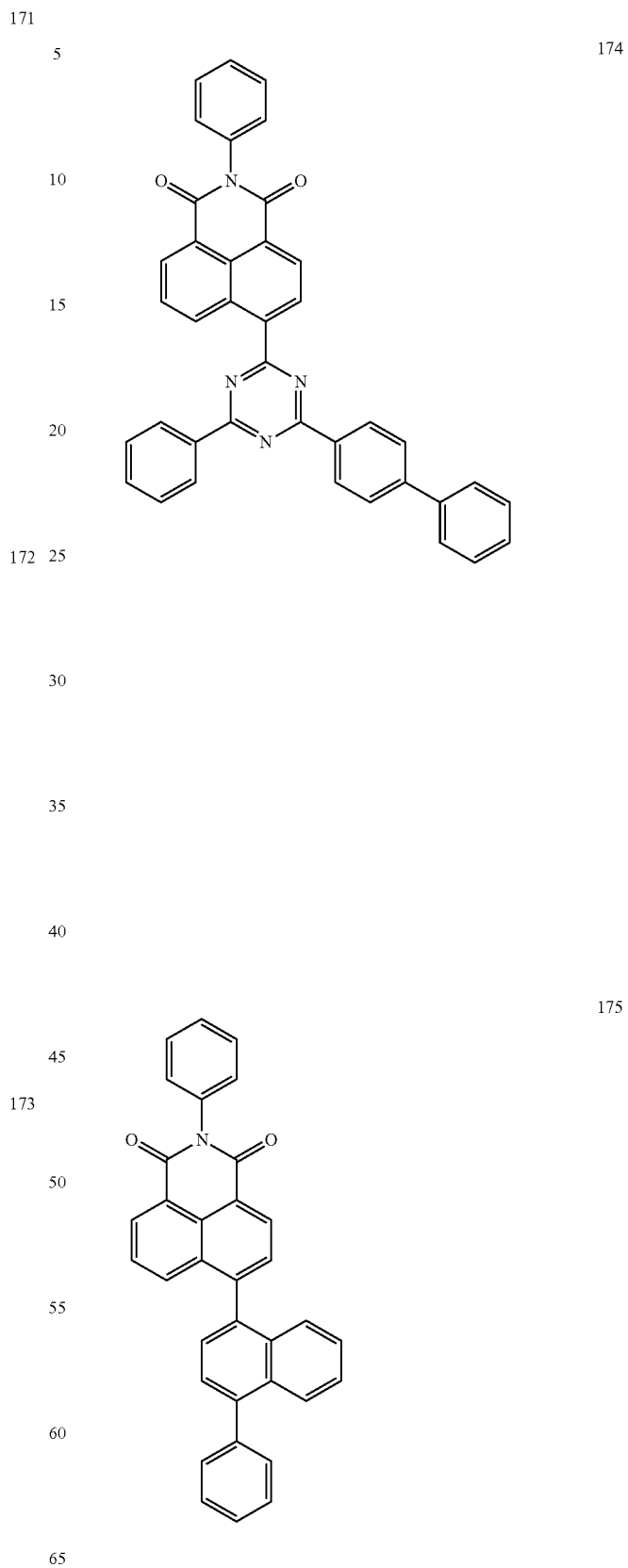

103
176 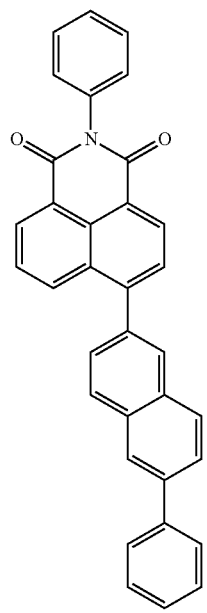
177 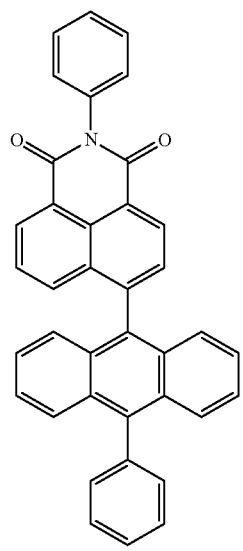
178 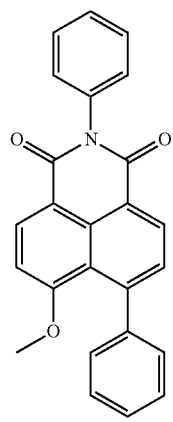
104
179 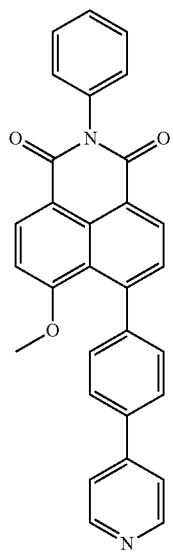
180 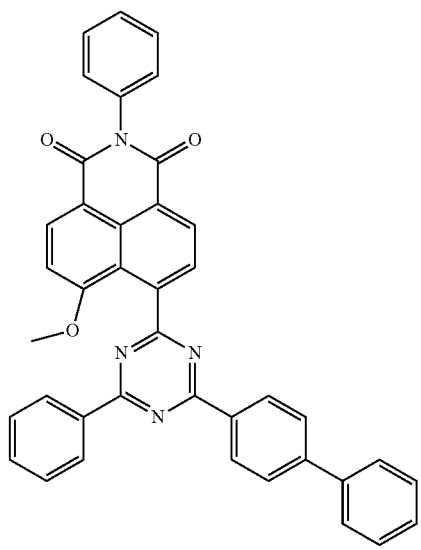
181 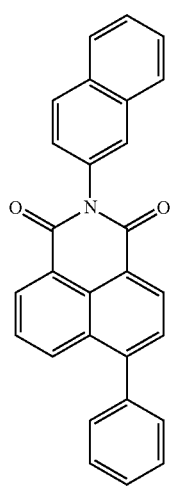

105
-continued
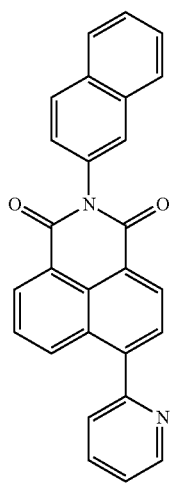
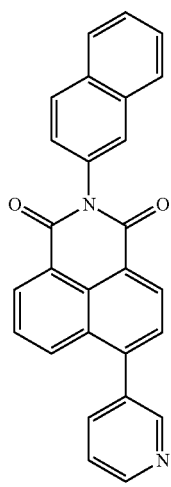
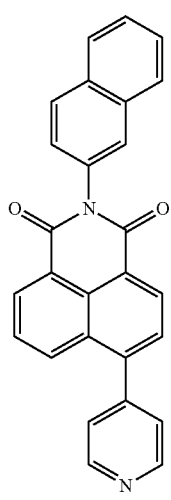
106
-continued
182
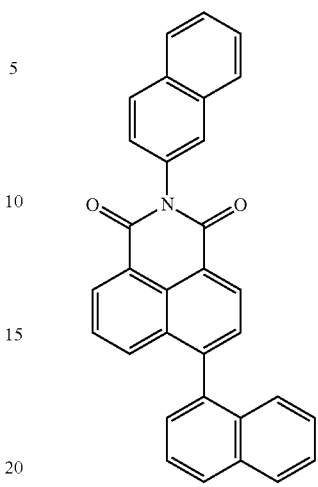
183
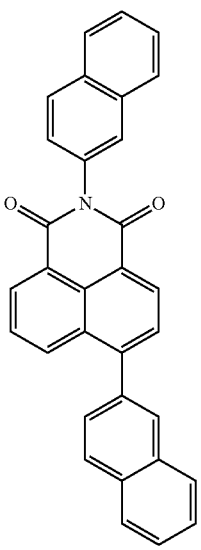
184
185
186
187
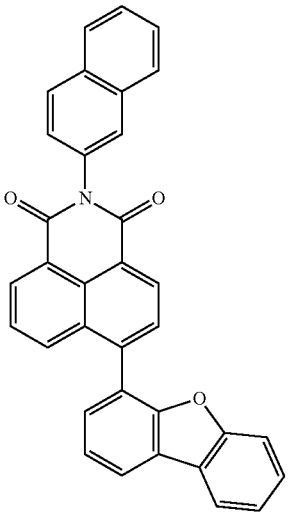

188
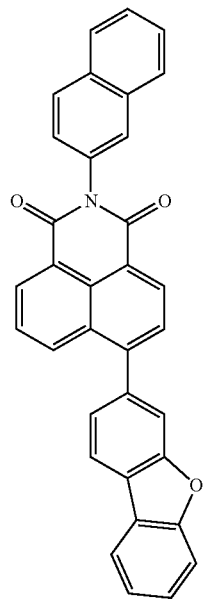
189
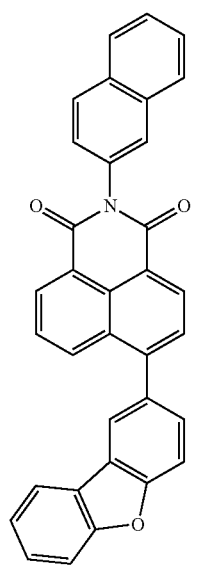
190
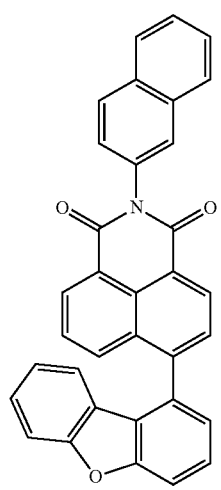
191
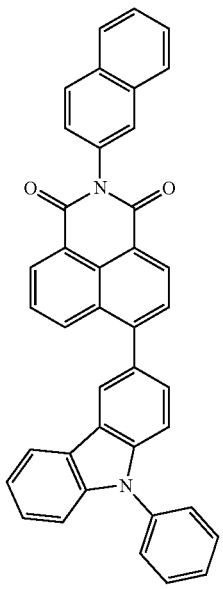
192
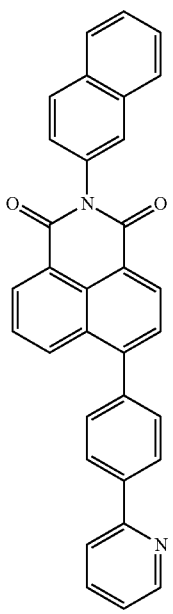

193
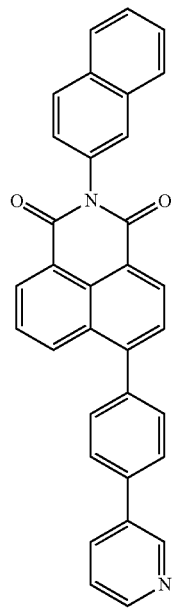
195
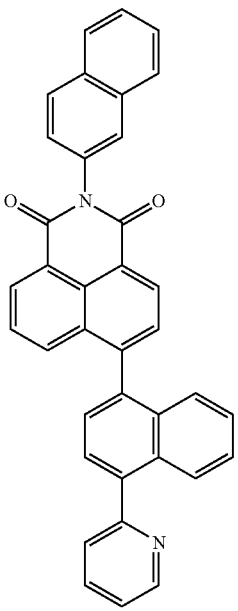
194
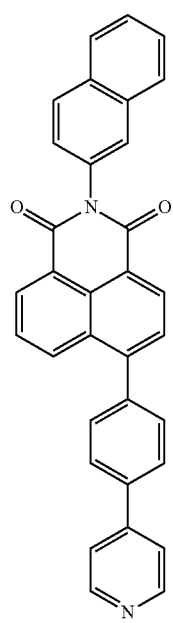
196
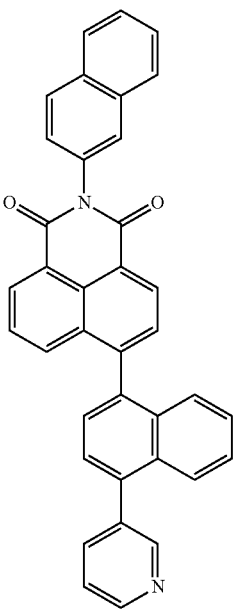

197
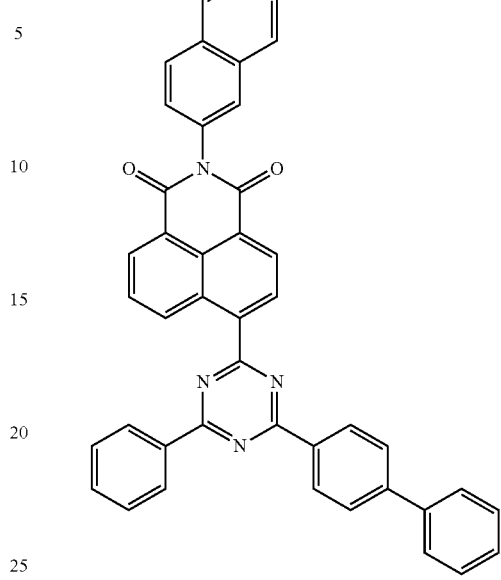
199
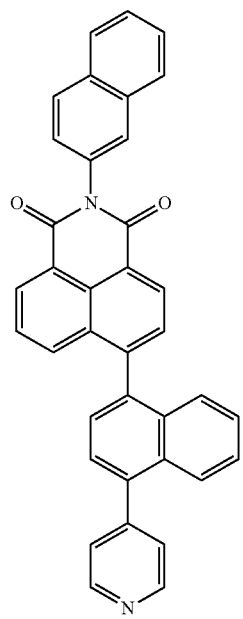
198
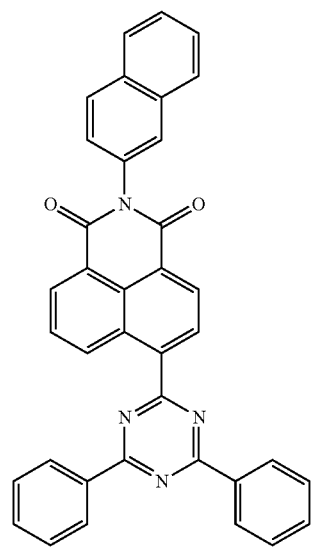
200
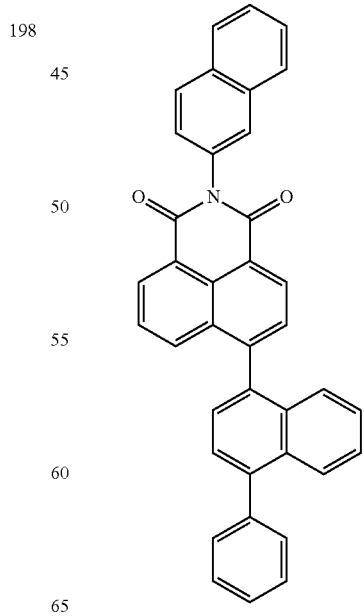

113
-continued
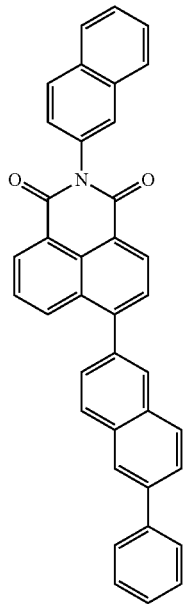
202
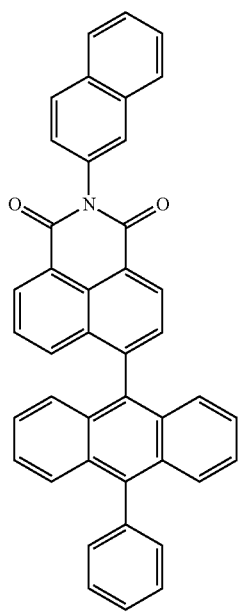
114
-continued
201
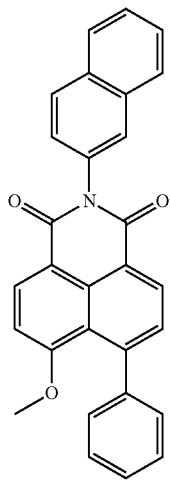
203
204
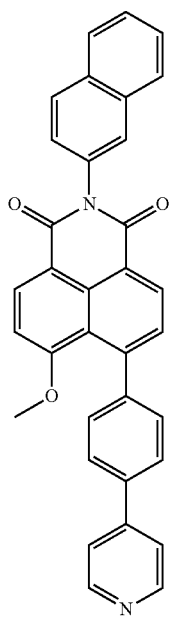

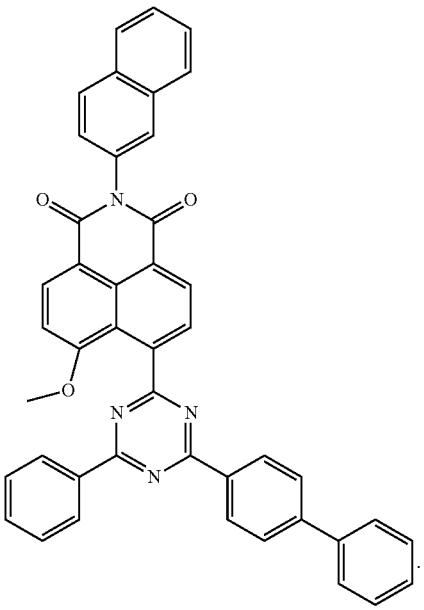

The first compound absorbs ultraviolet rays to prevent or substantially prevent the ultraviolet rays from transmitting through the organic light-emitting device 200. Therefore, the organic light-emitting display apparatus 10, in which the first compound is included in the encapsulation unit 300, may prevent or substantially prevent the emission layer, the insulating film, and/or the like (including the organic material) from being damaged by the ultraviolet rays. For example, the first compound may absorb light having a wavelength of about 400 nm to about 410 nm.

In one embodiment, a first compound solution in a solvent (e.g., the first compound dissolved in a solvent, for example, toluene) has a transmittance of about 10% or less (for example, about 8% or less) with respect to light having a wavelength of about 400 nm to about 410 nm (for example, about 405 nm).

In one or more embodiments, the first compound solution in the solvent (for example, toluene) has a transmittance of about 20% or more (for example, about 25% or more) with respect to light having a wavelength of about 425 nm to about 435 nm (for example, about 430 nm).

In one embodiment, the encapsulation unit 300 may further include a second compound that is different from the first compound, and a wavelength range of light absorbed by the first compound may be different from a wavelength range of light absorbed by the second compound.

For example, the second compound may include one selected from a benzophenone-based compound, a benzotriazole-based compound, a benzoate-based compound, a cyanoacrylate-based compound, a triazine-based compound, an oxanilide-based compound, and a salicylate-based compound.

The benzophenone-based compound may include, for example, 2,4-dihydroxybenzophenone, 2-hydroxy-4-methoxybenzophenone, 2-hydroxy-4-octylbenzophenone, 4-dodecyloxy-2-hydroxybenzophenone, 4-benzyloxy-2-hydroxybenzophenone, 2,2',4,4'-tetrahydroxybenzophenone, and 2,2'-dihydroxy-4,4'-dimethoxybenzophenone.

The benzotriazole-based compound may include, for example, 2-(5-methyl-2-hydroxyphenyl)benzotriazole, 2-[2-hydroxy-3,5-bis(α,α-dimethylbenzyl)phenyl]-2H-benzotriazole, 2-(3,5-di-t-butyl-2-hydroxyphenyl)benzotriazole, 2-(3-t-butyl-5-methyl-2-hydroxyphenyl)-5-chlorobenzotriazole, 2-(3,5-di-t-butyl-2-hydroxyphenyl)-5-chlorobenzotriazole, 2-(3,5-di-t-acyl-2-hydroxyphenyl)benzotriazole, and 2-(2'-hydroxy-5'-t-octylphenyl)benzotriazole.

The benzoate-based compound may include, for example, 2,4-di-t-butylphenyl-3',5'-di-t-butyl-4-hydroxybenzoate.

The triazine-based compound may include, for example, 2-[4-[(2-hydroxy-3-dodecyloxypropyl)oxy]-2-hydroxyphenyl]-4,6-bis(2,4-dimethylphenyl)-1,3,5-triazine, and the like.

The salicylate-based compound may include, for example, phenylsalicylate, 4-t-butylphenylsalicylate, and the like.

A mixing ratio of the first compound to the second compound may be appropriately selected by taking into account device characteristics, the degree of ultraviolet absorption, and/or the like.

In one embodiment, the encapsulation unit 300 may further include a third compound that is different from the first compound, and the first compound may be dispersed in the third compound. In one embodiment, the first compound may be simply dispersed in the third compound. In another embodiment, the first compound may be cross-linked to the third compound. For example, the first compound may include a group represented by Formula 2-3, and the first compound may be cross-linked to the third compound.

In one embodiment, the encapsulation unit 300 may further include a metal, a metal halide, a metal nitride, a metal oxide, a metal oxynitride, a silicon nitride, a silicon oxide, and/or a silicon oxynitride.

For example, the encapsulation unit 300 may include at least one selected from $MgF_2$, LiF, $AlF_3$, NaF, a silicon oxide, a silicon nitride, a silicon oxynitride, an aluminum oxide, an aluminum nitride, an aluminum oxynitride, a titanium oxide, a titanium nitride, a tantalum oxide, a tantalum nitride, a hafnium oxide, a hafnium nitride, a zirconium oxide, a zirconium nitride, a cerium oxide, a cerium nitride, a tin oxide, a tin nitride, and a magnesium oxide, but embodiments of the present disclosure are not limited thereto.

In one embodiment, the encapsulation unit 300 may include at least one organic film and at least one inorganic film, and the at least one organic film may include the first compound.

For example, the at least one organic film may consist of the first compound.

In one or more embodiments, the at least one organic film may further include, in addition to the first compound, the second compound. The second compound is the same as described above.

In one or more embodiments, the at least one organic film may further include, in addition to the first compound, the third compound, and the first compound may be dispersed in the third compound. Here, the first compound may be simply dispersed in the third compound, or the first compound may be cross-linked to the third compound.

For example, the third compound may be a polymer resin. The polymer resin may include, for example, an acryl-based resin, a methacryl-based resin, an isoprene-based resin, a vinyl-based resin, an epoxy-resin resin, a urethane-based resin, a cellulose-based resin, a perylene-based resin, and/or an imide-based resin, but embodiments of the present disclosure are not limited thereto.

A mixing ratio of the first compound to the third compound may be appropriately selected by taking into account device characteristics, the degree of ultraviolet absorption, and/or the like.

In one or more embodiments, the at least one organic film may further include the second compound and the third compound in addition to the first compound.

The at least one organic film may be formed in a certain region utilizing various suitable methods, such as vacuum deposition, spin coating, casting, Langmuir-Blodgett (MB) deposition, ink-jet printing, laser-printing, and laser-induced thermal imaging. The number and thickness of organic films may be appropriately selected by taking into account productivity, device characteristics, and/or the like.

In one embodiment, the at least one inorganic film may include a metal, a metal halide, a metal nitride, a metal oxide, a metal oxynitride, a silicon nitride, a silicon oxide, and/or a silicon oxynitride.

For example, the inorganic film may include at least one selected from $MgF_2$, LiF, $AlF_3$, NaF, a silicon oxide, a silicon nitride, a silicon oxynitride, an aluminum oxide, an aluminum nitride, an aluminum oxynitride, a titanium oxide, a titanium nitride, a tantalum oxide, a tantalum nitride, a hafnium oxide, a hafnium nitride, a zirconium oxide, a zirconium nitride, a cerium oxide, a cerium nitride, a tin oxide, a tin nitride, and a magnesium oxide, but embodiments of the present disclosure are not limited thereto.

The at least one inorganic film may be formed in a certain region utilizing various suitable methods, such as chemical vapor deposition (CVD), plasma-enhanced chemical vapor deposition (PECVD), sputtering, atomic layer deposition (ALD), and thermal evaporation. The number and thickness of inorganic films may be appropriately selected by taking into account productivity, device characteristics, and/or the like.

In one embodiment, the at least one organic film may include a first organic film, the at least one inorganic film may include a first inorganic film, and the first organic film may be disposed between the organic light-emitting device 200 and the first inorganic film. For example, the at least one organic film may include a first organic film, the at least one inorganic film may include a first inorganic film, and the first organic film and the second inorganic film may be sequentially stacked from the organic light-emitting device 200 in this stated order. It should be understood that the expression "sequentially stacked" does not exclude a case where another film is disposed between the organic light-emitting device 200 and the first organic film, and/or between the first organic film and the first inorganic film.

In one or more embodiments, the at least one organic film may include a first organic film, the at least one inorganic film may include a first inorganic film, and the first inorganic film may be disposed between the organic light-emitting device 200 and the first organic film. For example, the at least one organic film may include a first organic film, the at least one inorganic film may include a first inorganic film, and the first inorganic film and the first organic film may be sequentially stacked from the organic light-emitting device 200 in this stated order.

In one or more embodiments, the at least one organic film may include a first organic film, the at least one inorganic film may include a first inorganic film and a second inorganic film, and the first inorganic film, the first organic film, and the second inorganic film may be sequentially stacked from the organic light-emitting device 200 in this stated order.

In one or more embodiments, the at least one organic film may include a first organic film and a second organic film, the at least one inorganic film may include a first inorganic film, and the first organic film, the first inorganic film, and the second organic film may be sequentially stacked from the organic light-emitting device 200 in this stated order.

In one or more embodiments, the at least one organic film may include a first organic film and a second organic film, the at least one inorganic film may include a first inorganic film and a second inorganic film, and the first inorganic film, the first organic film, the second inorganic film, and the second organic film may be sequentially stacked from the organic light-emitting device 200 in this stated order.

In one or more embodiments, the at least one organic film may include a first organic film and a second organic film, the at least one inorganic film may include a first inorganic film and a second inorganic film, and the first organic film, the first inorganic film, the second organic film, and the second inorganic film may be sequentially stacked from the organic light-emitting device 200 in this stated order.

In one or more embodiments, the at least one organic film may include a first organic film and a second organic film, the at least one inorganic film may include a first inorganic film and a second inorganic film, and the first inorganic film, the second inorganic film, the first organic film, and the second organic film may be sequentially stacked from the organic light-emitting device 200 in this stated order.

In one or more embodiments, the at least one organic film may include a first organic film and a second organic film, the at least one inorganic film may include a first inorganic film and a second inorganic film, and the first organic film, the second organic film, the first inorganic film, and the second inorganic film may be sequentially stacked from the organic light-emitting device 200 in this stated order.

In one or more embodiments, the at least one organic film may include a first organic film and a second organic film, the at least one inorganic film may include a first inorganic film, a second inorganic film, and a third inorganic film, and the first inorganic film, the first organic film, the second inorganic film, the second organic film, and the third inorganic film may be sequentially stacked from the organic light-emitting device 200 in this stated order.

In one or more embodiments, the at least one organic film may include a first organic film, a second organic film, and a third organic film, the at least one inorganic film may include a first inorganic film and a second inorganic film, and the first organic film, the first inorganic film, the second organic film, the second inorganic film, and the third organic film, may be sequentially stacked from the organic light-emitting device 200 in this stated order, but embodiments of the present disclosure are not limited thereto. The number of organic films, the number of inorganic films, and the stacking order of the inorganic films and the organic films may be appropriately changed according to design.

The organic light-emitting display apparatus 10 may include a plurality of organic light-emitting devices 200. According to an embodiment, an organic light-emitting display apparatus 10 includes: a substrate; an organic emission unit disposed above the substrate and including a plurality of organic light-emitting devices 200; and an encapsulation unit 300 disposed above the organic emission unit and sealing the organic emission unit, wherein the encapsulation unit 300 includes the first compound represented by Formula 1. The first compound is the same as described above.

For example, the encapsulation unit 300 may further include the second compound and/or the third compound in addition to the first compound. The second compound and the third compound are the same as described above.

In one or more embodiments, the encapsulation unit 300 may further include, in addition to the first compound, a metal, a metal halide, a metal nitride, a metal oxide, a metal oxynitride, a silicon nitride, a silicon oxide, and/or a silicon oxynitride.

In one or more embodiments, the encapsulation unit 300 may include at least one organic film and at least one inorganic film, and the at least one organic film may include the first compound. The at least one organic film and the at least one inorganic film are the same as described above.

Figure 2:
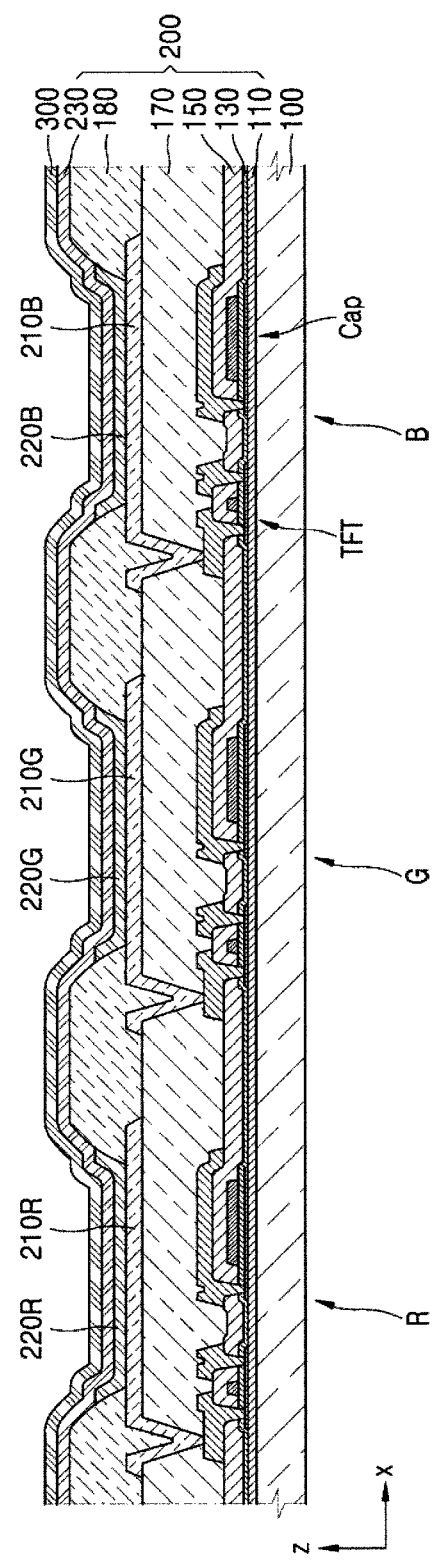
FIG. 2 is a schematic cross-sectional view of an organic light-emitting display apparatus according to another embodiment.

FIG. 2 is a schematic cross-sectional view of an organic light-emitting display apparatus according to an embodiment Referring to FIG. 2, a back plane is formed. The back plane may be understood as including a substrate 100, a plurality of first electrodes 210R, 210G, and 210G above the substrate 100, and a pixel defining film 180 exposing at least a part of a central portion of each of the plurality of first electrodes 210R, 210G, and 210B. The pixel defining film 180 may have a shape protruding more (e.g., higher) than the plurality of first electrodes 210R, 210G, and 210B (+z direction) with respect to the substrate 100.

The plurality of first electrodes 210R, 210G, and 210B may be understood as pixel electrodes. Among the pixel electrodes, the pixel electrode 210B, the pixel electrode 210R, and the pixel electrode 210G may be understood as a first pixel electrode, a second pixel electrode, and a third pixel electrode, respectively. This is because intermediate layers formed on the first to third pixel electrodes may be different from one another. Hereinafter, for convenience, the terms "pixel electrode 210R", "pixel electrode 210G", and "pixel electrode 210B" are utilized instead of the first pixel electrode, the second pixel electrode, and the third pixel electrode. The description of the pixel electrodes are substantially the same as the description of the first electrode.

The pixel defining film 180 has an opening corresponding to each sub-pixel, that is, an opening exposing the central portions of the pixel electrodes 210R, 210G, and 210B or the entire portions of the pixel electrodes 210R, 210G, and 210B, and thus may serve to define pixels. Also, the pixel defining film 180 increases a distance between ends of the pixel electrodes 210R, 210G, and 210B and a second electrode (not illustrated) above the pixel electrodes 210R, 210G, and 210B, thus preventing or reducing occurrence of arc at the ends of the pixel electrodes 210R, 210G, and 210B.

If necessary, the back plane may further include various elements. For example, as illustrated in FIG. 2, a thin film transistor TFT or a capacitor Cap may be formed on the substrate 100. The back plane may include other elements, such as a buffer layer 110 for preventing or substantially preventing impurities from penetrating into a semiconductor, layer of the thin film transistor TFT, a gate insulating film 130 for insulating the semiconductor layer of the thin film transistor TFT from a gate electrode thereof, an interlayer insulating layer 150 for insulating a source electrode and a drain electrode of the thin film transistor TFT from the gate electrode thereof, and a planarization film 170 covering the thin film transistor TFT and having a substantially flat upper surface.

After the back plane is formed, intermediate layers 220R, 220G, and 220B are formed. The intermediate layers 220R, 220G, and 220B may have a multi-layered structure including an emission layer. In this case, unlike that illustrated in FIG. 2, some of the intermediate layers 220R, 220G, and 220B may be a common layer substantially corresponding to the entire surface of the substrate 100, and others thereof may be pattern layers patterned corresponding to the pixel electrodes 210R, 210G, and 210B.

After the intermediate layers 220R, 220G, and 220B, a second electrode 230 is formed on the intermediate layers 220R, 220G, and 220B.

After the second electrode 230 is formed, an encapsulation unit 300 is formed so as to protect the organic light-emitting devices 200 including the pixel electrodes 210R, 210G, and 210B, the intermediate layers 220R, 220G, and 220B, and the second electrode 230 from impurities such as external oxygen and/or moisture.

The encapsulation unit 300 may extend to not only the upper surface but also the side surface of the organic light-emitting device 200 and contact a part of the substrate 100. Therefore, it is possible to effectively prevent or substantially prevent external oxygen and moisture from penetrating into the organic light-emitting device 200.

The encapsulation unit 300 may include the first compound represented by Formula 1.

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein refers to a divalent group having the same (e.g., substantially the same) structure as the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same (e.g., substantially the same) structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same (e.g., substantially the same) structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same (e.g., substantially the same) structure as the $C_3$-$C_{10}$ cycloalkyl group.

The term "$C_1$-$C_{10}$ heterocycloalkyl group" as used herein refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same (e.g., substantially the same) structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and examples thereof include a cyclopentenyl group, a cyclohexenyl group, and a cycloheptenyl group. The term "$C_3$-$C_{10}$ cycloalkenylene group" as used herein refers to a divalent group having the same (e.g., substantially the same) structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having the same (e.g., substantially the same) structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a carbocyclic aromatic system that has at least one heteroatom selected from N, O, Si, P, and S as a ring-forming atom, in addition to 1 to 1 carbon atoms. The term "$C_1$-$C_{60}$ heteroarylene group" as used herein refers to a divalent group having a carbocyclic aromatic system that has at least one heteroatom selected from N, O, Si, P, and S as a ring-forming atom, in addition to 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein refers to a group represented by —$OA_{102}$ (wherein $A_{102}$ is the $C_6$-$C_{60}$ aryl group), and the term "$C_6$-$C_{60}$ arylthio group" as used herein refers to a group represented by —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed with each other, only carbon atoms as ring-forming atoms, and no aromaticity in its entire molecular structure. An example of the monovalent non-aromatic condensed polycyclic group is a fluorenyl group. The term "divalent non-aromatic condensed polycyclic group" as used herein refers to a divalent group having the same (e.g., substantially the same) structure as the monovalent non-aromatic condensed polycyclic group.

The term "monovalent non-aromatic condensed heteropolycyclic group" as used herein refers to a monovalent group (for example, having 1 to 60 carbon atoms) having two or more rings condensed to each other, at least one heteroatom selected from N, O, Si, P, and S, other than carbon atoms, as a ring-forming atom, and no aromaticity in its entire molecular structure. An example of the monovalent non-aromatic condensed heteropolycyclic group is a carbazolyl group. The term "divalent non-aromatic condensed heteropolycyclic group" as used herein refers to a divalent group having the same (e.g., substantially the same) structure as the monovalent non-aromatic condensed heteropolycyclic group.

The term "$C_5$-$C_{60}$ carbocyclic group" as used herein refers to a monocyclic or polycyclic group having 5 to 60 carbon atoms in which the ring-forming atoms are carbon atoms only. The $C_5$-$C_{60}$ carbocyclic group may be an aromatic carbocyclic group or a non-aromatic carbocyclic group. The $C_5$-$C_{50}$ carbocyclic group may be a ring (such as benzene), a monovalent group (such as a phenyl group), or a divalent group (such as a phenylene group). In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same (e.g., substantially the same) structure as the $C_5$-$C_{60}$ carbocyclic group, except that as a ring-forming atom, at least one heteroatom selected from N, O, Si, P, and S is utilized in addition to carbon (the number of carbon atoms may be in a range of 1 to 60).

At least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cycloalkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cycloalkoxy group;

a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cycloalkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$ ($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" as used herein represents a phenyl group, the term "Me" as used herein represents a methyl group, the term "Et" as used herein represents an ethyl group, the term "ter-Bu" or "Bu$^t$" as used herein represents a tert-butyl group, and the term "OMe" as used herein represents a methoxy group.

The term "biphenyl group" as used herein refers to a "phenyl group substituted with a phenyl group. The "biphenyl group" is a "substituted phenyl group" having a "$C_6$-$C_{60}$ aryl group" as a substituent.

The term "terphenyl group" as used herein refers to a "phenyl group substituted with a biphenyl group. The "terphenyl group" is a "phenyl group" having, as a substituent, a "$C_6$-$C_{60}$ aryl group substituted with a $C_6$-$C_{60}$ aryl group."

* and *' as used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The expression "B was utilized instead of A" utilized in describing Synthesis Examples refers to that an identical number of molar equivalents of B was utilized in place of molar equivalents of A.

EXAMPLES

Synthesis Example 1: Synthesis of Compound 5

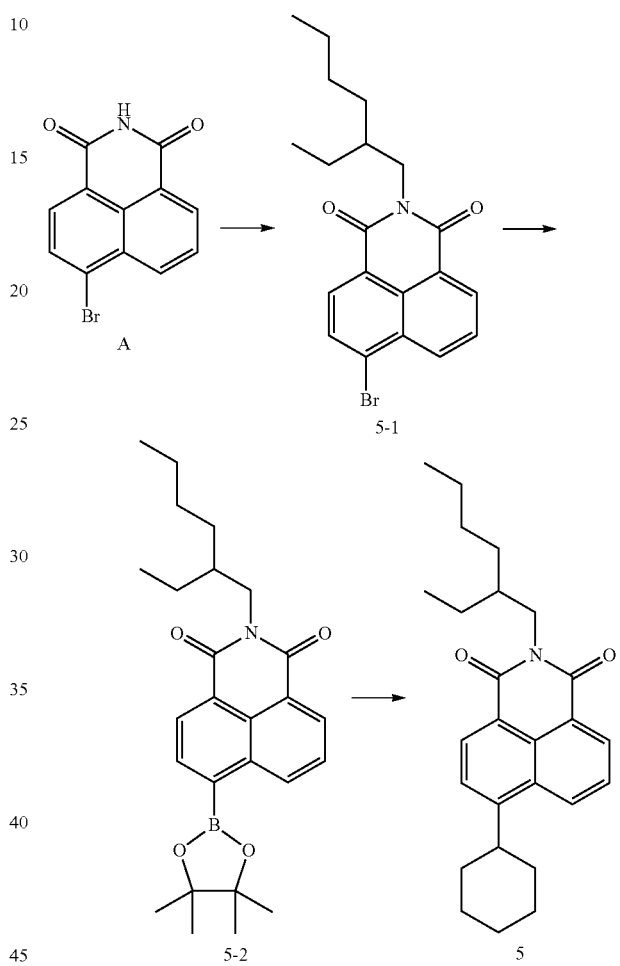

Synthesis of Intermediate 5-1

5 g of Intermediate A (6-bromo-1H-benzo[de]isoquinoline-1,3(2H)-dione) was dissolved in dimethylformamide (DMF), and 5 g of $K_2CO_3$ and 4 g of 3-(bromomethyl) hexane were added thereto. The mixture was stirred at a temperature of 50° C. for 24 hours, and the reaction was terminated by water. An extraction process was performed thereon three times utilizing ethyl acetate, a drying process was performed thereon utilizing anhydrous magnesium sulfate, and a filtering process was performed thereon under reduced pressure. Then, the residue obtained therefrom was separated and purified by column chromatography to obtain 5.6 g (80%) of Intermediate 5-1.

Synthesis of Intermediate 5-2

5.6 g of Intermediate 5-1 was diluted in toluene, and 5 g of KOAc, 4.6 g of bis(pinacolato)diboron, and 0.5 g of Pd(dppf)$_2$Cl$_2$ were added thereto and stirred under reflux. After 17 hours, the mixture was cooled to room temperature, and the reaction was terminated by water. An extraction process was performed thereon three times utilizing ethyl acetate, a drying process was performed thereon utilizing anhydrous magnesium sulfate, and a filtering process was performed thereon under reduced pressure. Then, the residue obtained therefrom was separated and purified by column chromatography to obtain 5.1 g (81%) of Intermediate 5-2.

Synthesis of Compound 5

5.1 g of Intermediate 5-2, 2.56 g of 1,4-dibromobenzene, 8 g of $Cs_2CO_3$, and 0.8 g of $Pd(PPh_3)_4$ were diluted in toluene and stirred under reflux. After 20 hours, the mixture was cooled to room temperature, and the reaction was terminated by water. An extraction process was performed thereon three times utilizing ethyl acetate, a drying process was performed thereon utilizing anhydrous magnesium sulfate, and a filtering process was performed thereon under reduced pressure. Then, the residue obtained therefrom was separated and purified by column chromatography to obtain 3.0 g (70%) of Compound 5.

Synthesis Example 2: Synthesis of Compound 7

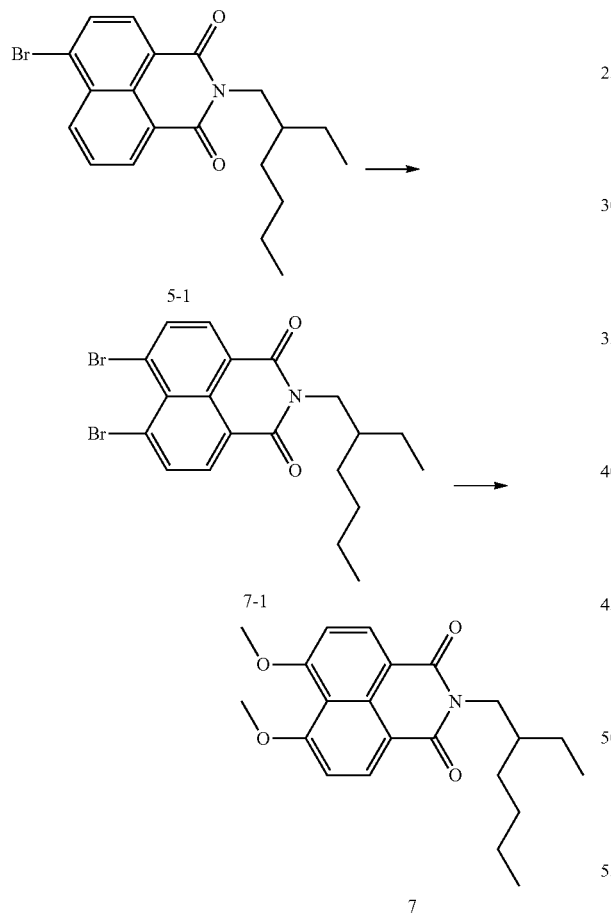

Synthesis of Intermediate 7-1

1.8 g of Intermediate 5-1 was diluted in methylene chloride (MC) and 900 mg of NBS was added dropwise thereto. The mixture was stirred for 15 hours, and the reaction was terminated by water. An extraction process was performed thereon three times, a drying process was performed thereon utilizing anhydrous magnesium sulfate, and a filtering process was performed thereon under reduced pressure. Then, the residue obtained therefrom was separated and purified by column chromatography to obtain 2 g (93%) of Intermediate 7-1. The obtained compound was confirmed by LC-MS. $C_{20}H_{21}Br_2NO_2$:M+ 465.2.

Synthesis of Compound 7

2 g of Compound 7-1 was diluted in DMSO and 2 g of NaOMe was added dropwise thereto. The reaction vessel was stirred at a temperature of 60° C. and slowly cooled to room temperature after 6 hours. The reaction was terminated by water, and the residue obtained therefrom was filtered under reduced pressure to obtain 1.4 g (88%) of Compound 7.

Synthesis Example 3: Synthesis of Compound 61

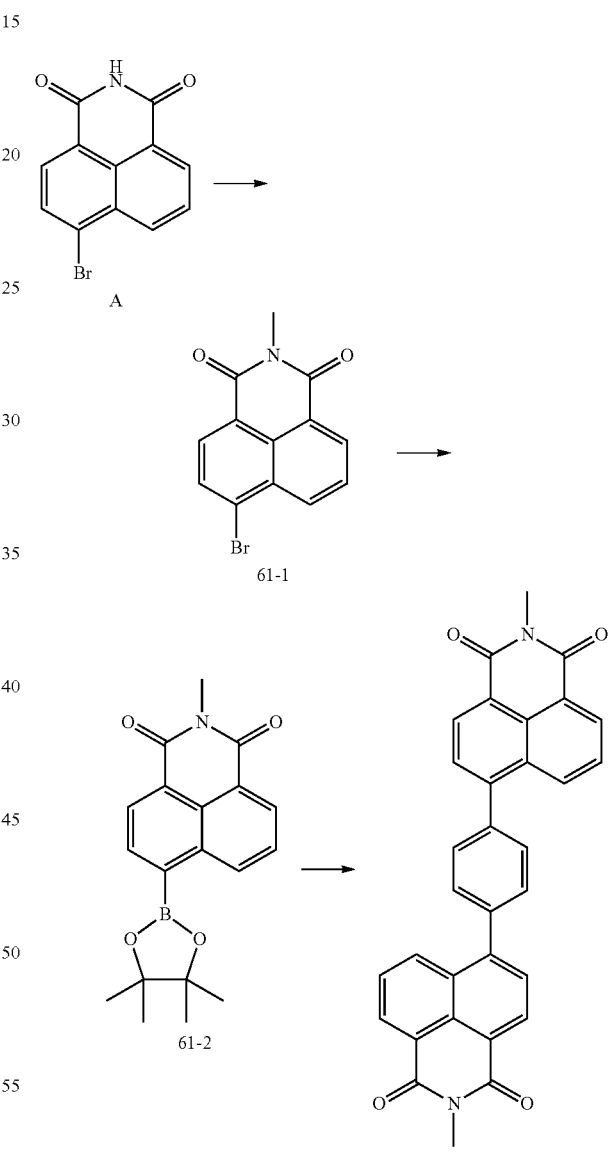

Synthesis of Intermediate 61-1

5 g of Intermediate A was dissolved in DMF, and 5 g of $K_2CO_3$ and 3 g of iodomethane were added thereto. The mixture was stirred at a temperature of 50° C. for 24 hours, and the reaction was terminated by water. An extraction process was performed thereon three times utilizing ethyl acetate, a drying process was performed thereon utilizing anhydrous magnesium sulfate, and a filtering process was performed thereon under reduced pressure. Then, the residue obtained therefrom was separated and purified by column chromatography to obtain 4.6 g (88%) of Intermediate 61-1. The obtained compound was confirmed by LC-MS. $C_{19}H_{15}Br$:M+ 324.2.

Synthesis of Intermediate 61-2

4.6 g of Intermediate 61-1 was diluted in toluene, and 5 g of KOAc, 4.6 g of bis(pinacolato)diboron, and 0.5 g of $Pd(dppf)_2Cl_2$ were added thereto and stirred under reflux. After 17 hours, the mixture was cooled to room temperature, and the reaction was terminated by water. An extraction process was performed thereon three times utilizing ethyl acetate, a drying process was performed thereon utilizing anhydrous magnesium sulfate, and a filtering process was performed thereon under reduced pressure. Then, the residue obtained therefrom was separated and purified by column chromatography to obtain 4.3 g (81%) of Intermediate 61-2. The obtained compound was confirmed by LC-MS. $C_{19}H_{15}Br$:M+ 324.2.

Synthesis of Compound 61

4.3 g of Intermediate 61-2, 2 g of 1,4-dibromobenzene, 8 g of $Cs_2CO_3$, and 0.8 g of $Pd(PPh_3)_4$ were diluted in toluene and stirred under reflux. After 20 hours, the mixture was cooled to room temperature, and the reaction was terminated by water. An extraction process was performed thereon three times utilizing ethyl acetate, a drying process was performed thereon utilizing anhydrous magnesium sulfate, and a filtering process was performed thereon under reduced pressure. Then, the residue obtained therefrom was separated and purified by column chromatography to obtain 2.8 g (76%) of Compound 61.

Synthesis Example 4: Synthesis of Compound 67

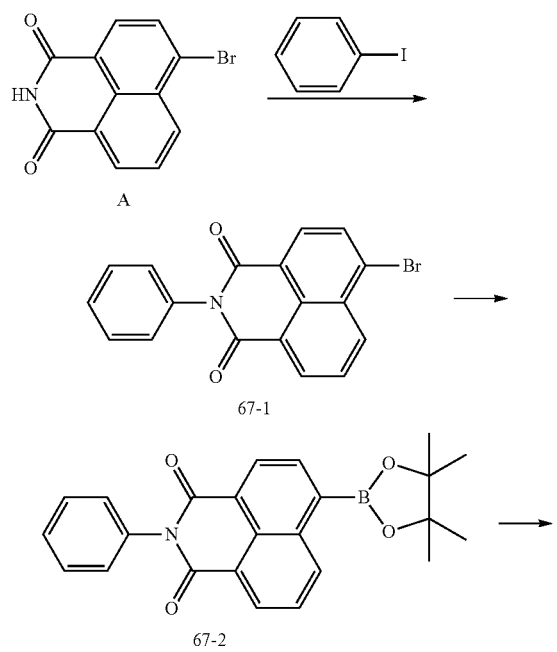

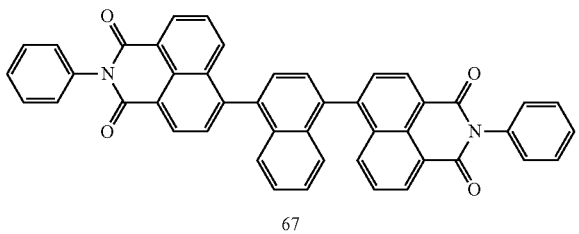

67

Synthesis of Intermediate 67-1

2.8 g of Intermediate A, 2.1 g of iodobenzene, 5.4 g of KOtBu, 0.2 g of $P(tBu)_3$, and 0.4 g of $Pd_2(dba)_3$ were diluted in toluene and stirred under reflux. After 20 hours, the mixture was cooled to room temperature, and the reaction was terminated by water. An extraction process was performed thereon three times utilizing ethyl acetate, a drying process was performed thereon utilizing anhydrous magnesium sulfate, and a filtering process was performed thereon under reduced pressure. Then, the residue obtained therefrom was separated and purified by column chromatography to obtain 2.9 g (80%) of Intermediate 67-1. The obtained compound was confirmed by LC-MS. $C_{18}H_{10}BrNO_2$:M+ 351.0.

Synthesis of Intermediate 67-2

2.8 g (84%) of Intermediate 67-2 was synthesized in the same (e.g., substantially the same) manner as in Synthesis of Intermediate 61-2, except that 2.9 g of Intermediate 67-1 was utilized. The obtained compound was confirmed by LC-MS. $C_{24}H_{22}BNO_4$:M+ 399.2.

Synthesis of Compound 67

2.1 g (45%) of Compound 67 was synthesized in the same (e.g., substantially the same) manner as in Synthesis of Compound 61, except that 2.8 g of Intermediate 67-2 and 1 g of 1,4-dibromonaphthalene were utilized.

Synthesis Example 5: Synthesis of Compound 76

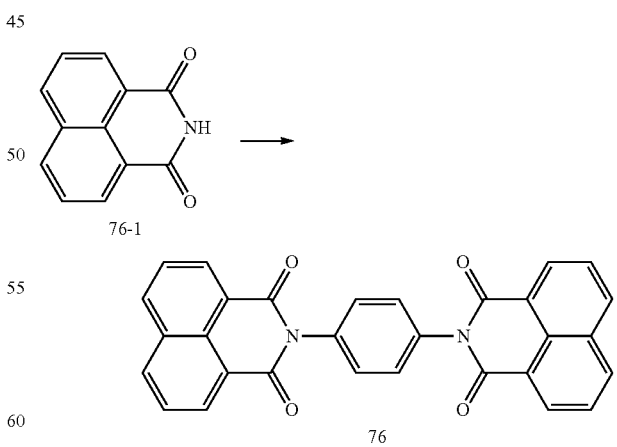

2.99 g (63%) of Compound 76 was synthesized in the same (e.g., substantially the same) manner as in Synthesis of Compound 67-1, except that Compound 76-1 and 1,4-dibromobenzene were utilized.

Synthesis Example 6: Synthesis of Compound 88

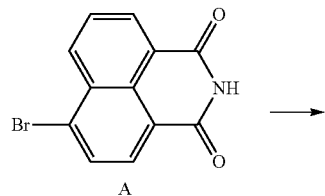

A

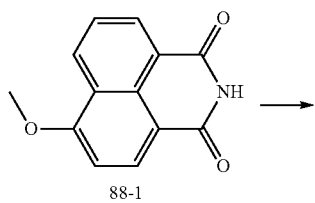

88-1

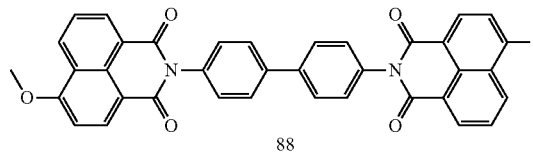

88

Synthesis of Intermediate 88-1

2 g of Compound A was diluted in DMSO and 2 g of NaOMe was added dropwise thereto. The reaction vessel was stirred at a temperature of 60° C. and slowly cooled to room temperature after 6 hours. The reaction was terminated by water, and the residue obtained therefrom was filtered under reduced pressure to obtain 1.3 g (79%) of Intermediate 88-1. The obtained compound was confirmed by LC-MS. $C_{13}H_9NO_3$:M+ 227.1.

Synthesis of Compound 88

2 g (58%) of Compound 88 was synthesized in the same (e.g., substantially the same) manner as in Synthesis of Compound 61, except that 1.3 g of Intermediate 88-1 and 0.89 g of 4,4'-dibromo-1,1'-biphenyl were utilized.

Synthesis Example 7: Synthesis of Compound 111

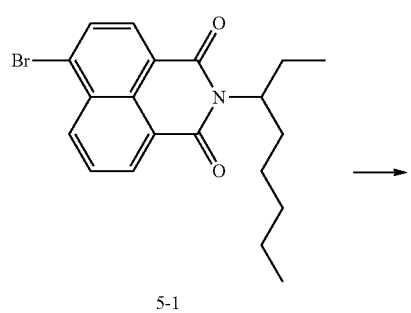

5-1

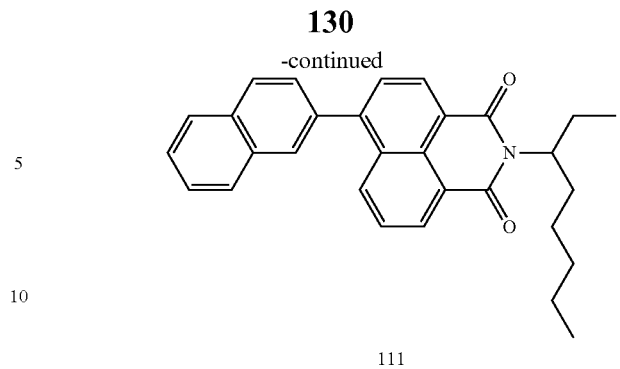

111

1.6 g (80%) of Compound 111 was synthesized in the same (e.g., substantially the same) manner as in Synthesis of Compound 61, except that 1.8 g of Intermediate 5-1 and 1 g of naphthalen-2-yl boronic acid were utilized.

Synthesis Example 8: Synthesis of Compound 120

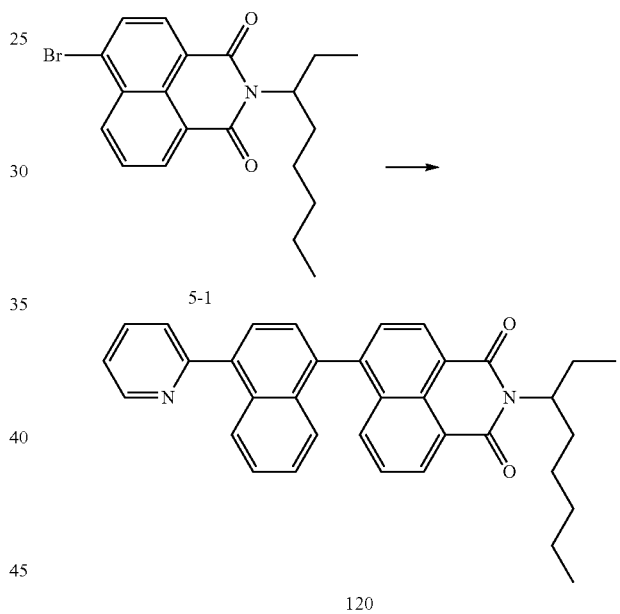

5-1

120

1.1 g (42%) of Compound 120 was synthesized in the same (e.g., substantially the same) manner as in Synthesis of Compound 61, except that 2 g of Intermediate 5-1 and 1.7 g of (4-(pyridin-2-yl)naphthalen-1-yl)boronic acid were utilized.

Synthesis Example 9: Synthesis of Compound 169

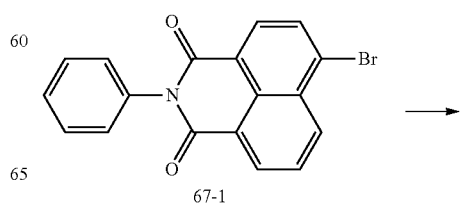

67-1

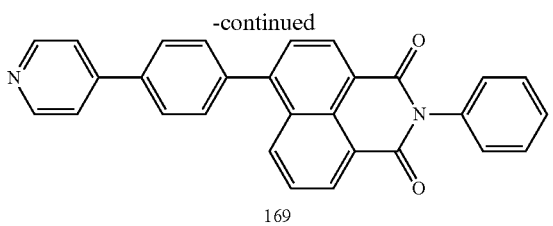

169

1.4 g (49%) of Compound 169 was synthesized in the same (e.g., substantially the same) manner as in Synthesis of Compound 61, except that 2.3 g of Intermediate 67-1 and 1.7 g of (4-(pyridin-4-yl)phenyl)boronic acid were utilized.

Synthesis Example 10: Synthesis of Compound 181

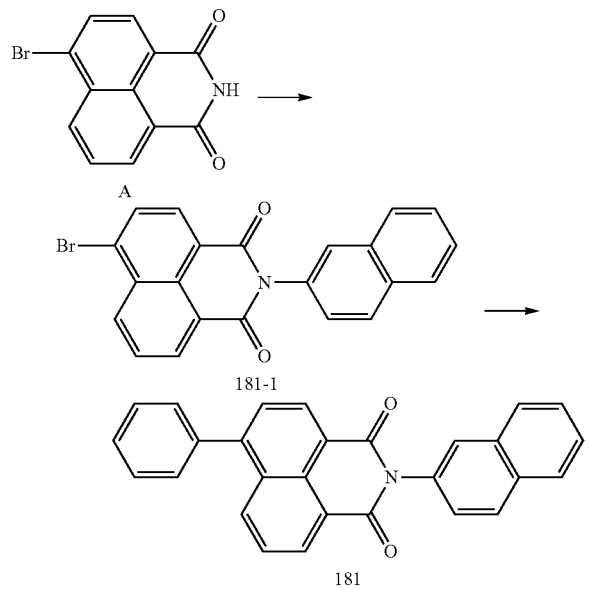

181

Synthesis of Intermediate 181-1

1.6 g (73%) of Intermediate 181-1 was synthesized in the same (e.g., substantially the same) manner as in Synthesis of Intermediate 67-1, except that 1.5 g of Intermediate A and 1.5 g of 2-iodonaphthalene were utilized. The obtained compound was confirmed by LC-MS. $C_{22}H_{12}BrNO_2$:M+ 401.0

Synthesis of Compound 181

1.2 g (78%) of Compound 181 was synthesized in the same (e.g., substantially the same) manner as in Synthesis of Compound 61, except that 1.6 g of Intermediate 181-1 and 1.3 g of phenylboronic acid were utilized.

Synthesis Example 11: Synthesis of Compound 198

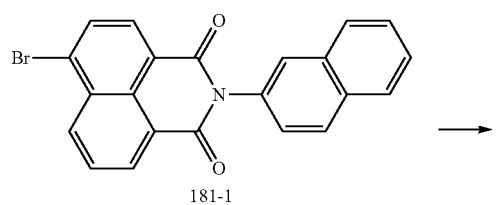

181-1

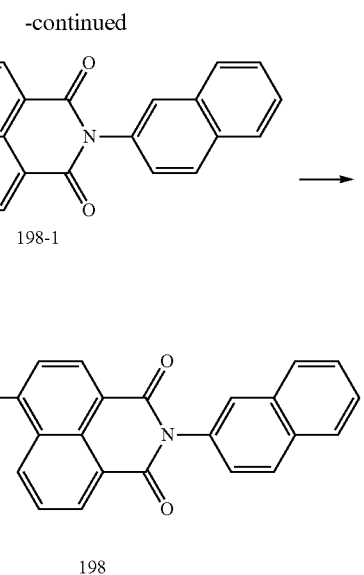

198-1

198

Synthesis of Intermediate 198-1

1.9 g (87%) of Intermediate 198-1 was synthesized in the same (e.g., substantially the same) manner as in Synthesis of Intermediate 67-2, except that 2 g of Intermediate 181-1 was utilized. The obtained compound was confirmed by LC-MS. $C_{28}H_{24}BNO_4$:M+ 449.2.

Synthesis of Compound 198

1.5 g (62%) of Compound 198 was synthesized in the same (e.g., substantially the same) manner as in Synthesis of Compound 61, except that 1.9 g of Intermediate 198-1 and 1.3 g of 2-chloro-4,6-diphenyl-1,3,5-triazine were utilized.

TABLE 1

| Com- | | LC-MS | |
| pound | $^1$H NMR(CDCl$_3$, 400 MHz) | found | Calc |
| --- | --- | --- | --- |
| 5 | 8.48-8.33(m, 3H), 7.88(m, 1H), 7.11(m, 1H) 3.12(d, 2H), 2.72(m, 1H), 1.92-0.88(m, 25H) | 391.2 | 391.2 |
| 7 | 8.69(d, 2H), 6.95(d, 2H), 4.03(s, 6H), 3.68(m, 2H), 2.11(m, 1H), 1.45-1.20(m, 8H), 0.87(t, 6H) | 465.0 | 465.0 |
| 61 | 8.59(d, 2H), 8.22(d, 2H), 8.12(d, 2H), 7.85(m, 2H), 7.75(m, 4H), 7.70(m, 2H), 3.48(s, 6H) | 469.2 | 496.1 |
| 67 | 8.43-8.40(m, 2H), 8.22(m, 2H), 8.11(dd, 2H), 8.05(br, 2H), 7.71-7.40(m, 16H), 7.00 (m, 2H) | 670.7 | 670.7 |
| 76 | 8.41 (dd, 4H) 8.24 (dd, 4H), 8.74-7.69(m, 8H) | 468.6 | 468.5 |
| 88 | 8.55-8.42(m, 6H) 7.63-7.55(m, 6H), 7.23-7.18(m, 4H), 6.83(d, 2H), 4.02(s, 6H) | 604.6 | 604.6 |
| 111 | 8.51(d, 1H), 8.18-8.08(m, 2H), 7.99-7.88(m, 3H), 7.69-7.52(m, 4H), 7.32(d, 1H), 5.01 (m, 1H), 2.20(2H), 1.97-1.89(m, 2H), 1.71-1.52(m, 2H), 1.36-1.24(m, 2H), 1.04(m, 2H), 0.93-0.83(m, 6H) | 435.2 | 435.2 |
| 120 | 8.72(d, 1H), 8.47(d, 1H), 8.18-8.08(m, 2H), 7.82-7.67(m, 5H), 7.46-7.44(m, 1H), 7.38(m, 1H), 7.25-7.23(m, 2H), 7.06-7.02(d, 1H), 5.01 (m, 1H), 2.20(2H), 1.97-1.89(m, 2H), 1.71-1.52(m, 2H), 1.36-1.24(m, 2H), 1.04(m, 2H), 0.93-0.83(m, 6H) | 512.7 | 512.7 |
| 169 | 8.73-8.70(m, 2H), 8.48(dd, 1H), 8.16 (td, 2H), 7.81-7.63(m, 6H), 7.52-7.40(m, 7H) | 426.5 | 426.5 |
| 181 | 8.53(d, 1H), 8.33(m, 1H), 8.24(d, 1H), 8.22-8.12(m, 4H), 7.88-7.65(m, 5H), 7.53-7.28(m, 6H) | 399.4 | 399.4 |
| 198 | 8.86-8.80(m, 4H), 8.72(d, 1H), 8.52(d, 1H), 8.46(dd, 1H), 8.45-8.40(m, 1H), 8.33(m, 1H), 7.92(m, 1H), 7.86(m, 1H), 7.80(m, 1H), 7.63-7.58(m, 5H), 7.51-7.46(m, 2H), 7.42-7.36(m, 4H), 7.33-7.30(m, 1H) | 554.2 | 554.2 |

Evaluation Example 1

UV transmittance of Compounds prepared according to Synthesis Examples 1 to 11 was measured at a concentration of $10^{-5}$ M in a toluene solvent (i.e., in toluene) utilizing Shimazu UV-1800, and results thereof are shown in Table 2.

TABLE 2

| | UV absorber | Solubility (in toluene) | Transmittance (@ 405 nm) | Transmittance (@ 430 nm) |
|---|---|---|---|---|
| Comparative Example 1 | UV POL | — | 1.8 | 30.00 |
| Example 1 | 5 | 10 wt % | 3.38 | 40.18 |
| Example 2 | 7 | 11 wt % | 7.54 | 75.15 |
| Example 3 | 61 | 5 wt % | 1.68 | 29.47 |
| Example 4 | 67 | 6 wt % | 4.12 | 48.21 |
| Example 5 | 76 | 8 wt % | 4.54 | 50.52 |
| Example 6 | 88 | 6 wt % | 2.54 | 33.56 |
| Example 7 | 111 | 9 wt % | 3.98 | 52.52 |
| Example 8 | 120 | 7 wt % | 1.55 | 32.56 |
| Example 9 | 169 | 5 wt % | 2.99 | 42.52 |
| Example 10 | 181 | 4 wt % | 4.02 | 52.11 |
| Example 11 | 198 | 3 wt % | 3.32 | 45.11 |

As can be confirmed from Table 2, the first compound represented by Formula 1 has a low transmittance in an optical wavelength of about 405 nm. Therefore, an organic light-emitting display apparatus, in which the first compound represented by Formula 1 is included in an encapsulation unit, may prevent or substantially prevent an emission layer, an insulating film, and/or the like including an organic material from being damaged by ultraviolet rays.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims, and equivalents thereof.

What is claimed is:

1. An organic light-emitting display apparatus comprising:
   a substrate;
   an organic light-emitting device on the substrate; and
   an encapsulation unit on the organic light-emitting device and configured to seal the organic light-emitting device,
   wherein the encapsulation unit comprises a first compound represented by Formula 1:

Formula 1

$[R_1\text{---}(L_1)_{a1}]_{b1}\text{---}(Ar_1)_{c1}\text{---}[(L_2)_{a2}\text{---}R_2]_{b2}$

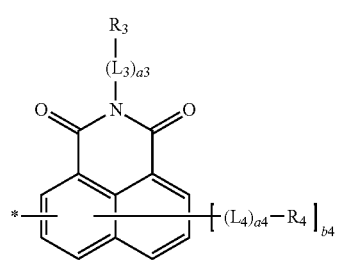

Formula 2-1

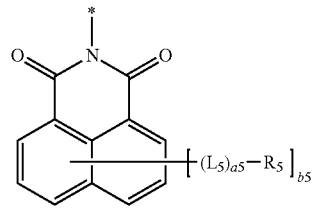

Formula 2-2

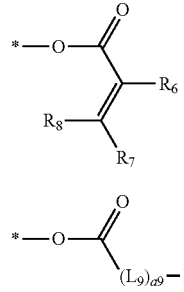

Formula 2-3

Formula 2-4 wherein, in Formulae 1 and 2-1 to 2-4, $Ar_1$ is a $C_5$-$C_{60}$ carbocyclic group or a $C_2$-$C_{30}$ heterocyclic group, c1 is 0 or 1, $L_1$ to $L_5$ and $L_9$ are each independently selected from *—N($R_{11}$)—*', *—B($R_{11}$)—*', *—P($R_{11}$)—*', *—Si($R_{11}$)($R_{12}$)—*', *—S—*', *—Se—*', *—O—*', *—C(=O)—*', *—S(=O)—*', *—S(=O)$_2$—*', *—C($R_{11}$)—*', *—C(=S)—*', a substituted or unsubstituted $C_1$-$C_{60}$ alkylene group, a substituted or unsubstituted $C_2$-$C_{60}$ alkenylene group, a substituted or unsubstituted $C_2$-$C_{60}$ alkynylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a5 and a9 are each independently an integer from 0 to 10, $R_1$ is a group represented by Formula 2-1 or a group represented by Formula 2-2, $R_2$ to $R_5$ are each independently selected from a group represented by Formula 2-3, a group represented by Formula 2-4, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_6$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, Si($Q_1$)($Q_2$)($Q_3$), —N($Q_1$)($Q_2$), —B($Q_1$)($Q_2$), —C(=O)($Q_1$), —S(=O)$_2$ ($Q_1$), and —P(=O)($Q_1$)($Q_2$), $R_6$ to $R_9$, $R_{11}$, and $R_{12}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, Si($Q_4$)($Q_5$)($Q_6$), —N($Q_4$)($Q_5$), —B($Q_4$)($Q_5$), —C(=O)($Q_4$), —S(=O)$_2$($Q_4$), and —P(=O)($Q_4$)($Q_5$), b1 is an integer from 1 to 10, wherein, when b1 is two or more, two or more *-($L_1$)$_{a1}$-$R_1$(s) are identical to or different from each other, b2 is an integer from 1 to 10, wherein, when b2 is two or more, two or more *-($L_2$)$_{a2}$-$R_2$(s) are identical to or different from each other, b4 is an integer from 0 to 5, wherein, when b4 is two or more, two or more *-($L_4$)$_{a4}$-$R_4$(s) are identical to or different from each other, b5 is an integer from 0 to 6, wherein, when b5 is two or more, two or more *-($L_5$)$_{a5}$-$R_5$(s) are identical to or different from each other, at least one substituent of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cycloalkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cycloalkoxy group;

a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cycloalkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_6$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group, and

* and *' each indicate a binding site to a neighboring atom.

2. The organic light-emitting display apparatus of claim 1, wherein $Ar_1$ is selected from a benzene group, a naphthalene group, an anthracene group, a phenanthrene group, a pyrene group, a chrysene group, a triphenylene group, an indene group, a fluorene group, a benzofluorene group, a spiro-bifluorene group, a carbazole group, a dibenzofuran group, a dibenzothiophene group, a pyridine group, a pyrazine group, a pyrimidine group, a pyridazine group, a pyrrole group, an imidazole group, a quinoline group, an isoquinoline group, a quinoxaline group, a quinazoline group, a triazine group, an indeno pyrazine group, an indeno pyridine group, a phenanthroline group, and a phenanthridine group.

3. The organic light-emitting display apparatus of claim 1, wherein $L_1$ to $L_5$ and $L_9$ are each independently selected from:
*—S—*', *—O—*', *—C(=O)—*', *—S(=O)—*', *—S(=O)$_2$—*', a $C_1$-$C_{20}$ alkylene group, a $C_2$-$C_{20}$ alkenylene group, a $C_2$-$C_{20}$ alkynylene group, a phenylene group, a pentalenylene group, an indenylene group, a naphthylene group, an azulenylene group, an indacenylene group, an acenaphthylene group, a fluorenylene group, a spiro-bifluorenylene group, a spiro-benzofluorene-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a carbazolylene group, a benzocarbazolylene group, a dibenzocarbazolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azaspiro-bifluorenylene group, an azacarbazolylene group, an azadibenzofuranylene group, an azadibenzothiophenylene group, and an azadibenzosilolylene group; and a $C_1$-$C_{20}$ alkylene group, a $C_2$-$C_{20}$ alkenylene group, a $C_2$-$C_{20}$ alkynylene group, a phenylene group, a pentalenylene group, an indenylene group, a naphthylene group, an azulenylene group, an indacenylene group, an acenaphthylene group, a fluorenylene group, a spiro-bifluorenylene group, a spiro-benzofluorene-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a perylenylene group, a pentaphenylene group, a pyrrolylene group, a thiophenylene group, a furanylene group, a silolylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an indolylene group, an isoindolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, a benzofuranylene group, a benzothiophenylene group, a benzosilolylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a carbazolylene group, a benzocarbazolylene group, a dibenzocarbazolylene group, a thiadiazolylene group, an imidazopyridinylene group, an imidazopyrimidinylene group, an oxazolopyridinylene group, a thiazolopyridinylene group, a benzonaphthyridinylene group, an azafluorenylene group, an azaspiro-bifluorenylene group, an azacarbazolylene group, an azadibenzofuranylene group, an azadibenzothiophenylene group, and an azadibenzosilolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{20}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, and —Si($Q_{31}$)($Q_{32}$)($Q_{33}$), $Q_{31}$ to $Q_{33}$ are each independently selected from:

a $C_1$-$C_{10}$ alkyl group, a $C_1$-$C_{10}$ alkoxy group, a $C_3$-$C_{10}$ cycloalkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a $C_1$-$C_{10}$ alkyl group, a $C_1$-$C_{10}$ alkoxy group, a $C_3$-$C_{10}$ cycloalkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, a $C_3$-$C_{10}$ cycloalkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, and

* and *' each indicate a binding site to a neighboring atom.

4. The organic light-emitting display apparatus of claim 1, wherein $L_1$ to $L_5$ and $L_9$ are each independently selected from *—S—*', *—O—*', *—C(=O)—*', *—S(=O)—*', *—S(=O)$_2$—*', *—[C($Z_1$)($Z_2$)]$_{n1}$—*', and groups represented by Formulae 3-1 to 3-75:

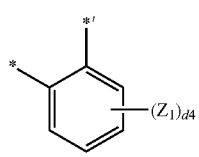

Formula 3-1

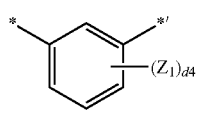

Formula 3-2

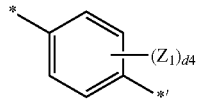

Formula 3-3

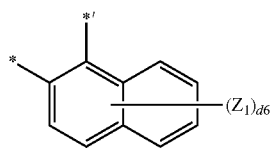

Formula 3-4

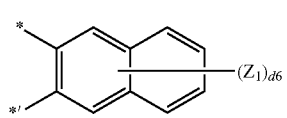

Formula 3-5

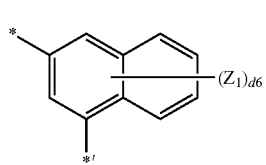

Formula 3-6

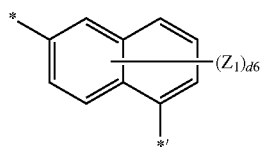

Formula 3-7

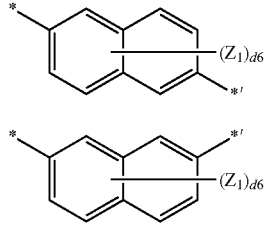

Formula 3-8

Formula 3-9

-continued

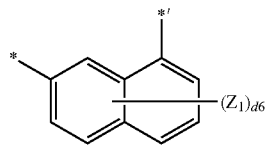

Formula 3-10

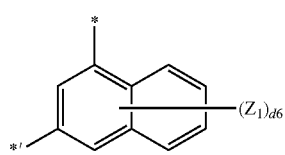

Formula 3-11

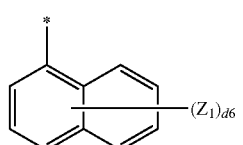

Formula 3-12

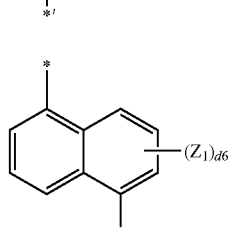

Formula 3-13

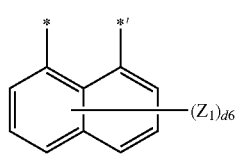

Formula 3-14

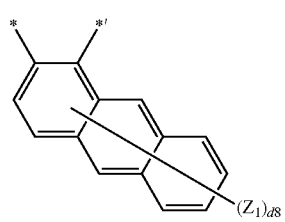

Formula 3-15

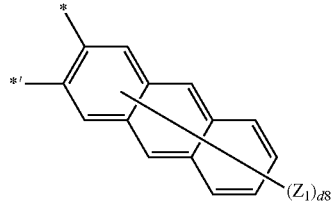

Formula 3-16

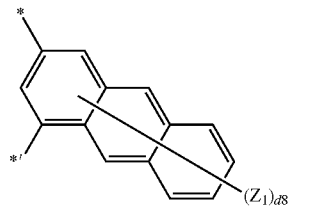

Formula 3-17

-continued
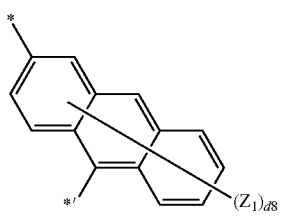
Formula 3-18
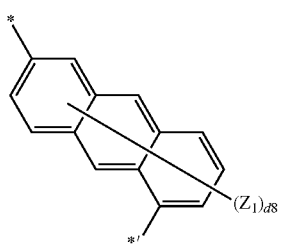
Formula 3-19
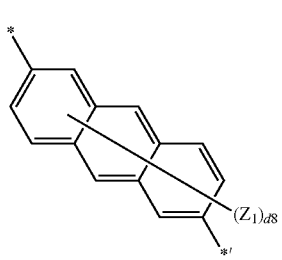
Formula 3-20
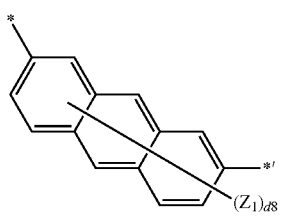
Formula 3-21
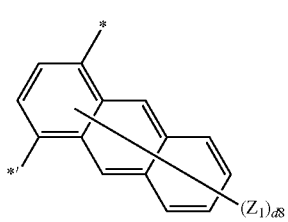
Formula 3-22
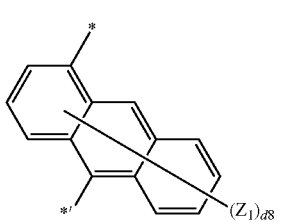
Formula 3-23
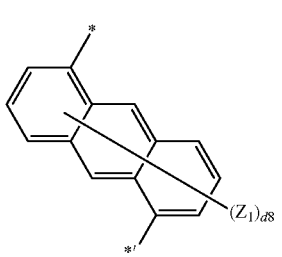
Formula 3-24
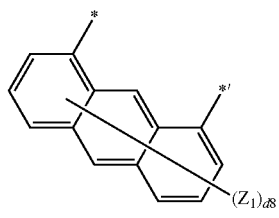
Formula 3-25
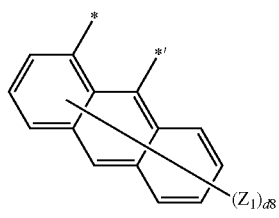
Formula 3-26
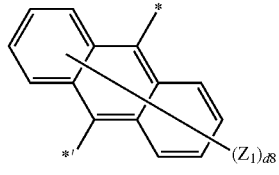
Formula 3-27
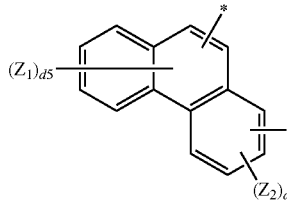
Formula 3-28
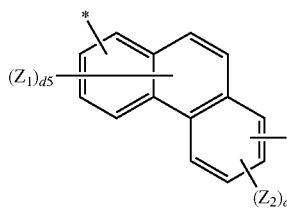
Formiula 3-29
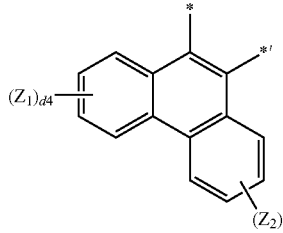
Formula 3-30
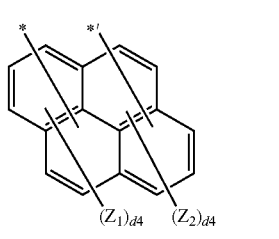
Formula 3-31

-continued
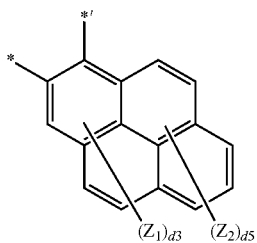
Formula 3-32
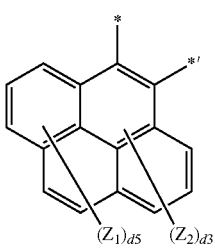
Formula 3-33
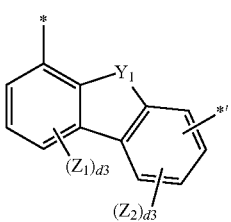
Formula 3-34
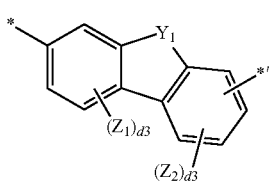
Formula 3-35
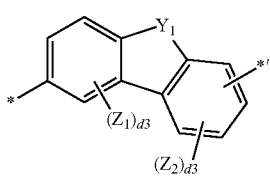
Formula 3-36
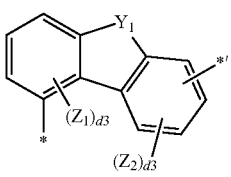
Formula 3-37
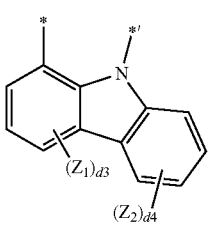
Formula 3-38
-continued
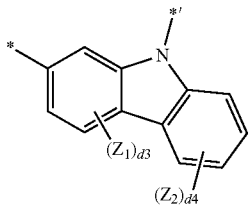
Formula 3-39
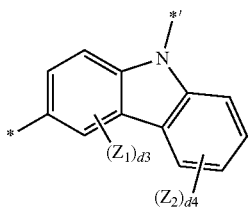
Formula 3-40
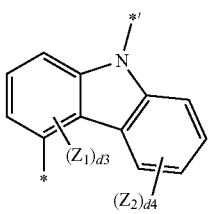
Formula 3-41
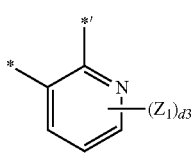
Formula 3-42
Formula 3-43
Formula 3-44
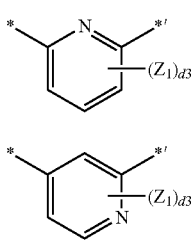
Formula 3-45
Formula 3-46
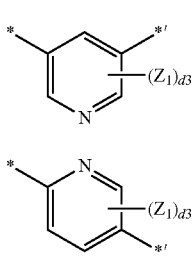
Formula 3-47
Formula 3-48
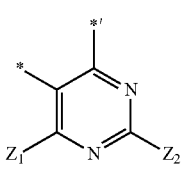

-continued
Formula 3-49
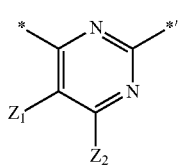
Formula 3-50
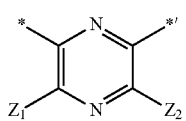
Formula 3-51
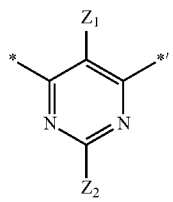
Formula 3-52
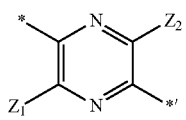
Formula 3-53
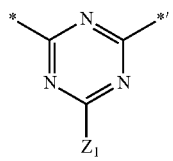
Formula 3-54
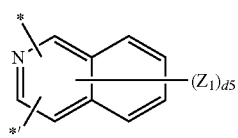
Formula 3-55
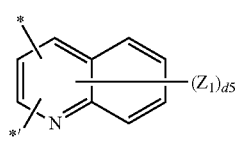
Formula 3-56
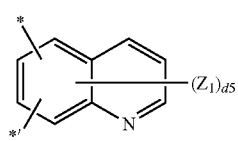
Formula 3-57
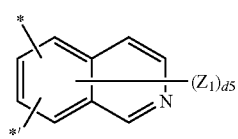
Formula 3-58
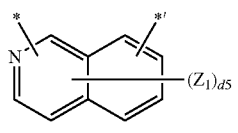
Formula 3-59
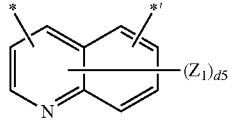
-continued
Formula 3-60
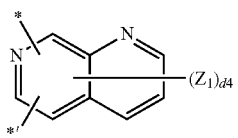
Formula 3-61
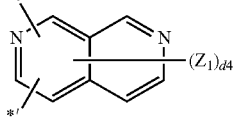
Formula 3-62
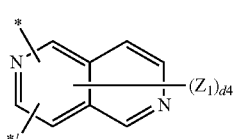
Formula 3-63
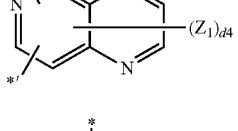
Formula 3-64
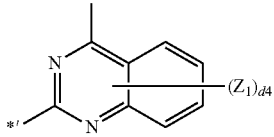
Formula 3-65
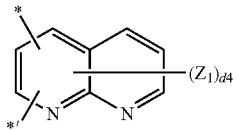
Formula 3-66
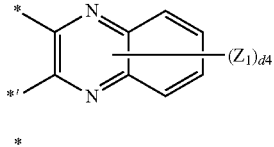
Formula 3-67
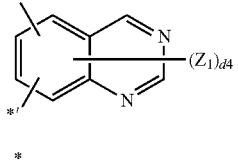
Formula 3-68
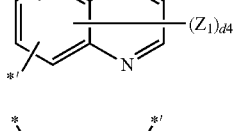
Formula 3-69
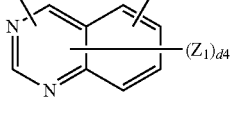
Formula 3-70
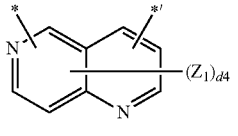

-continued

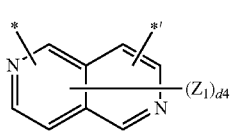
Formula 3-71

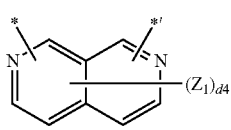
Formula 3-72

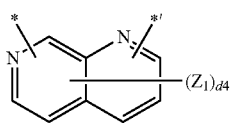
Formula 3-73

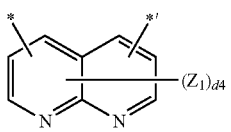
Formula 3-74

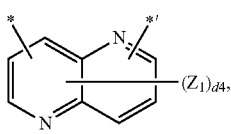
Formula 3-75 wherein, in Formulae 3-1 to 3-75, $Y_1$ is O, S, C($Z_3$)($Z_4$), N($Z_3$), or Si($Z_3$)($Z_4$), $Z_1$ to $Z_4$ are each independently selected from hydrogen, deuterium, —F, —CF$_3$, —Cl, —Br, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a triazinyl group, and —Si($Q_{31}$)($Q_{32}$)($Q_{33}$), $Q_{31}$ to $Q_{33}$ are each independently selected from a $C_1$-$C_{10}$ alkyl group, a $C_1$-$C_{10}$ alkoxy group, a $C_3$-$C_{20}$ cycloalkoxy group, a phenyl group, a biphenyl group, a terphenyl group, and a naphthyl group, d3 is an integer from 1 to 3,
d4 is an integer from 1 to 4,
d5 is an integer from 1 to 5,
d6 is an integer from 1 to 6,
d8 is an integer from 1 to 8,
n1 is an integer from 1 to 20, and
* and *' each indicate a binding site to a neighboring atom.

5. The organic light-emitting display apparatus of claim 1, wherein

Ar$_1$ is selected from groups represented by Formulae 4-1 to 4-59, and

L$_1$ to L$_5$ and L$_9$ are each independently selected from *—O—*', *—C(=O)—*', *—CH$_2$—*', *—(CH$_2$)$_2$—*', *—(CH$_2$)$_3$—*', *—(CH$_2$)$_4$—*', *—(CH$_2$)$_5$—*', and groups represented by Formulae 4-1 to 4-58 and 4-60:

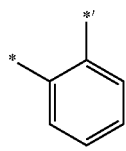
Formula 4-1

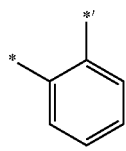
Formula 4-2

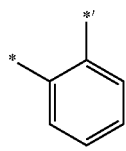
Formula 4-3

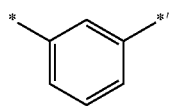
Formula 4-4

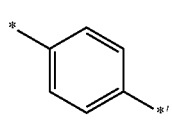
Formula 4-5

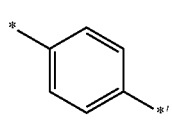
Formula 4-6

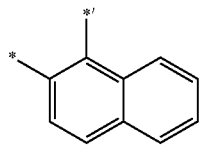
Formula 4-7

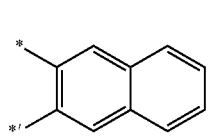
Formula 4-8

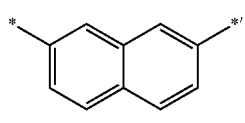
Formula 4-9

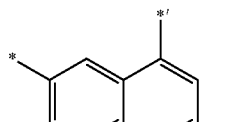
Formula 4-10

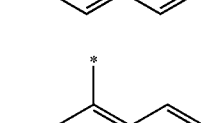
Formula 4-11

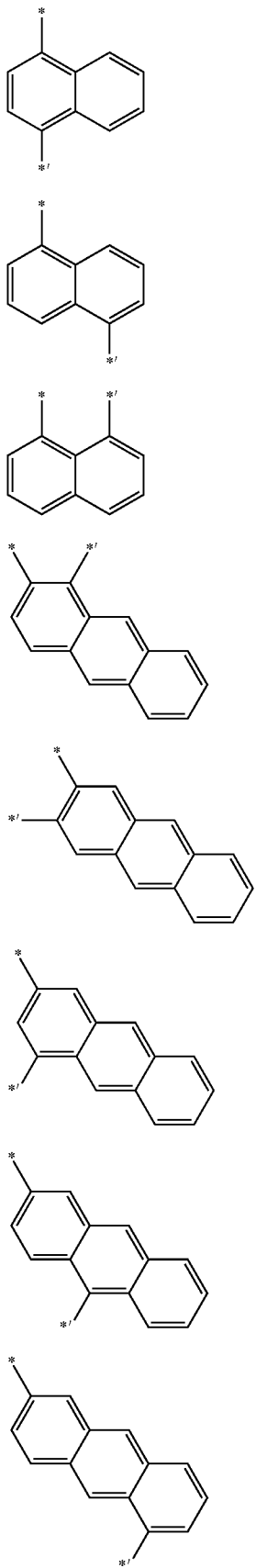
Formula 4-12
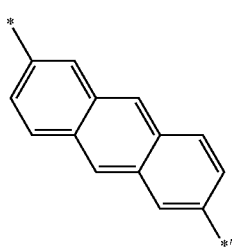
Formula 4-20
Formula 4-13
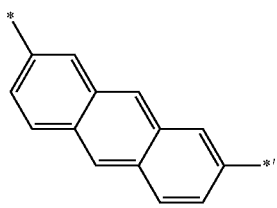
Formula 4-21
Formula 4-14
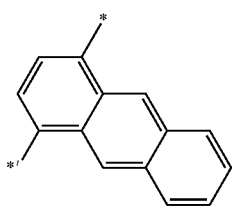
Formula 4-22
Formula 4-15
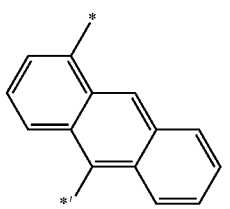
Formula 4-23
Formula 4-16
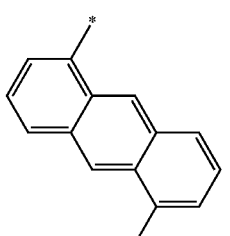
Formula 4-24
Formula 4-17
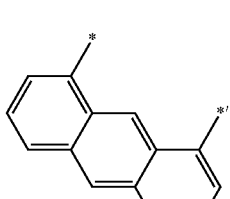
Formula 4-25
Formula 4-18
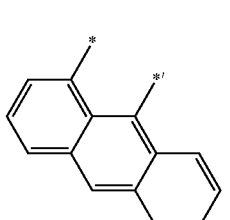
Formula 4-26
Formula 4-19
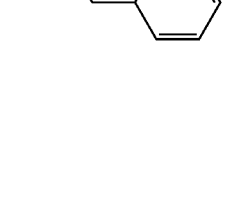

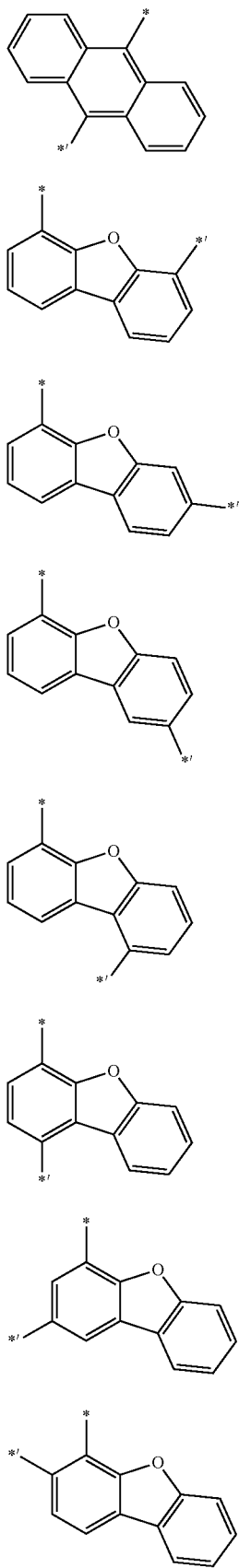
Formula 4-27
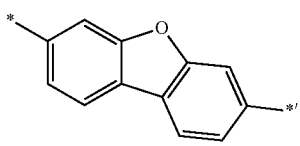
Formula 4-28
Formula 4-29
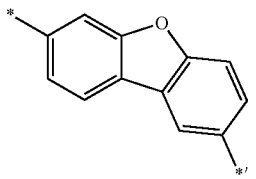
Formula 4-30
Formula 4-31
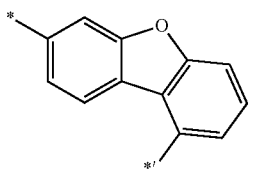
Formula 4-32
Formula 4-33
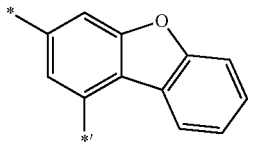
Formula 4-34
Formula 4-35
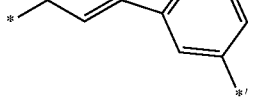
Formula 4-36
Formula 4-37
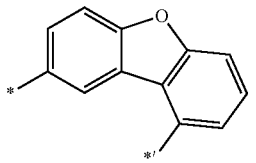
Formula 4-38
Formula 4-39
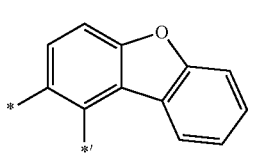
Formula 4-40
Formula 4-41
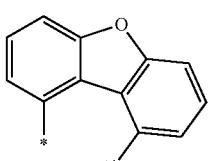
Formula 4-42
Formula 4-43
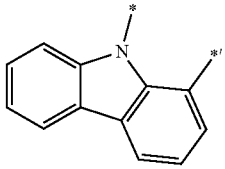

-continued

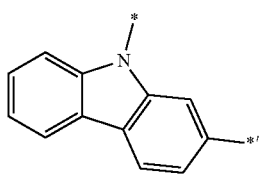
Formula 4-44

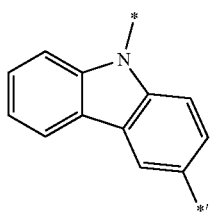
Formula 4-45

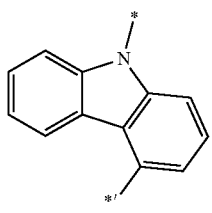
Formula 4-46

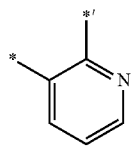
Formula 4-47

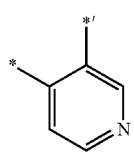
Formula 4-48

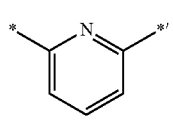
Formula 4-49

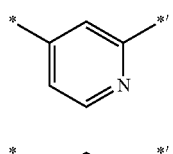
Formula 4-50

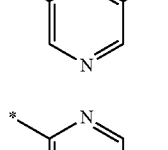
Formula 4-51

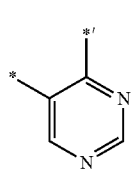
Formula 4-52

Formula 4-53

-continued

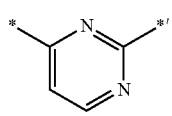
Formula 4-54

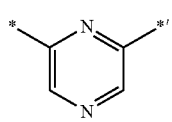
Formula 4-55

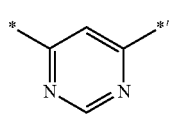
Formula 4-56

Formula 4-57

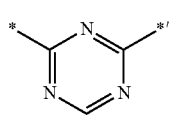
Formula 4-58

Formula 4-59

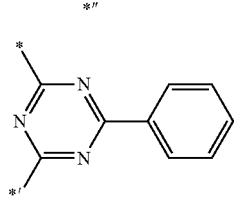

Formula 4-60

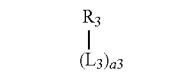

wherein *, *', and *'' in Formulae 4-1 to 4-60 each indicate a binding site to a neighboring atom.

6. The organic light-emitting display apparatus of claim 1, wherein
the group represented by Formula 2-1 is represented by Formula 2-1A:

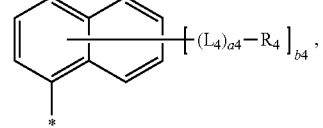

Formula 2-1A wherein, in Formula 2-1A, $L_3$, $L_4$, a3, a4, $R_3$, $R_4$, and b4 are the same as described in claim 1, and * indicates a binding site to a neighboring atom.

7. The organic light-emitting display apparatus of claim 1, wherein $R_2$ to $R_5$ are each independently selected from:

a group represented by Formula 2-3, a group represented by Formula 2-4, hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, a triazinyl group, and —Si($Q_1$)($Q_2$)($Q_3$); and a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, a triazinyl group, and —Si($Q_{31}$)($Q_{32}$)($Q_{33}$), and $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

8. The organic light-emitting display apparatus of claim 1, wherein $R_6$ to $R_9$, $R_{11}$, and $R_{12}$ are each independently selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, a triazinyl group, and —Si($Q_4$)($Q_5$)($Q_6$); and a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, and a triazinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_3$-$C_{10}$ cycloalkyl group, a $C_1$-$C_{20}$ alkoxy group, a $C_3$-$C_{20}$ cycloalkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a carbazolyl group, a benzocarbazolyl group, a dibenzocarbazolyl group, a furanyl group, a benzofuranyl group, a dibenzofuranyl group, a thiophenyl group, a benzothiophenyl group, a dibenzothiophenyl group, a pyridinyl group, a pyrazinyl group, a pyrimidinyl group, a pyridazinyl group, a triazinyl group, and —Si($Q_{31}$)($Q_{32}$)($Q_{33}$), and $Q_4$ to $Q_6$ and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

9. The organic light-emitting display apparatus of claim 1, wherein the first compound is represented by one of Formulae 1A to 1P:

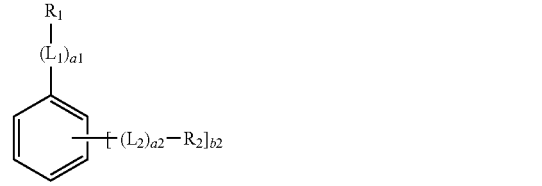

Formula 1A

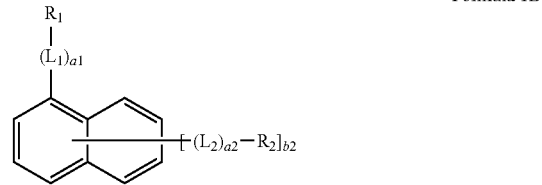

Formula 1B

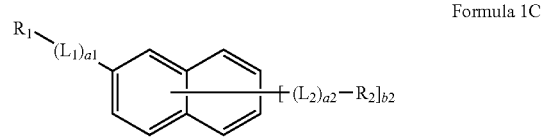

Formula 1C

Formula 1D
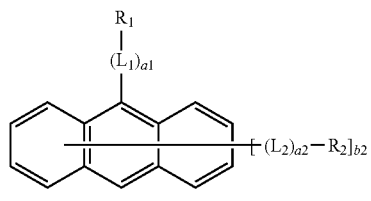
Formula 1E
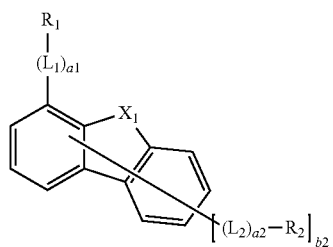
Formula 1F
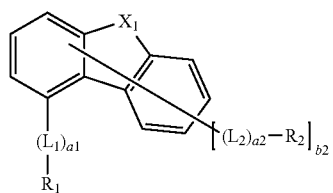
Formula 1G
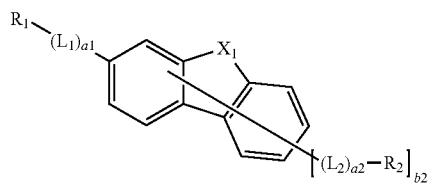
Formula 1H
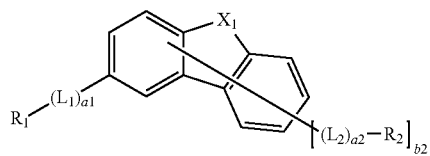
Formula 1I
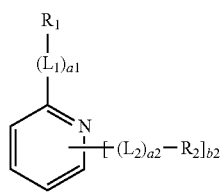
Formula 1J
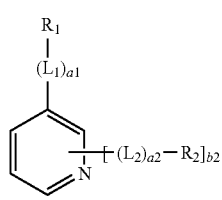
Formula 1K
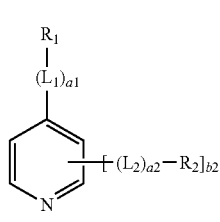
Formula 1L
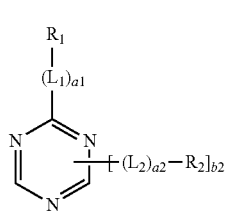
Formula 1M
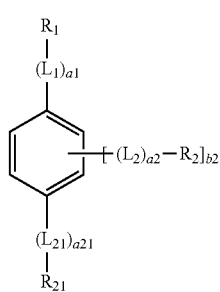
Formula 1N
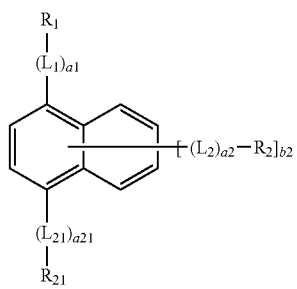
Formula 1O
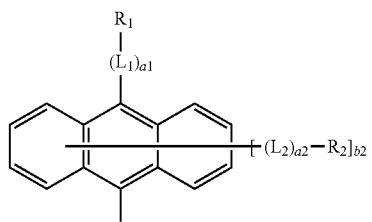
Formula 1P
$R_1—(L_1)_{a1}—(L_2)_{a2}—R_2,$
wherein, in Formulae 1A to 1P,
$L_1$, $L_2$, a1, a2, $R_1$, $R_2$, and b2 are the same as described in claim 1, and
$L_{21}$, a21, and $R_{21}$ are the same as described in connection with $L_1$, a1, and $R_1$.
10. The organic light-emitting display apparatus of claim 1, wherein the first compound is one of Compounds 1 to 205:
1
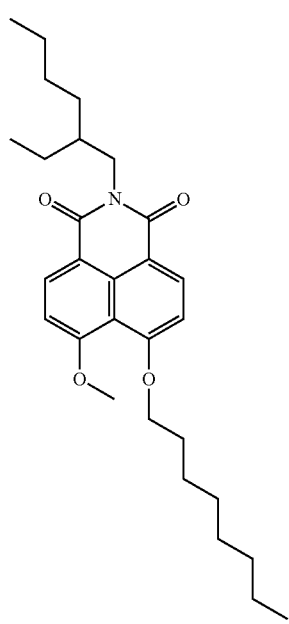
2
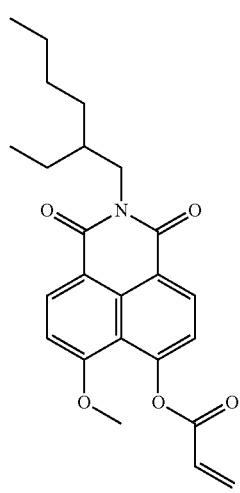
3
4
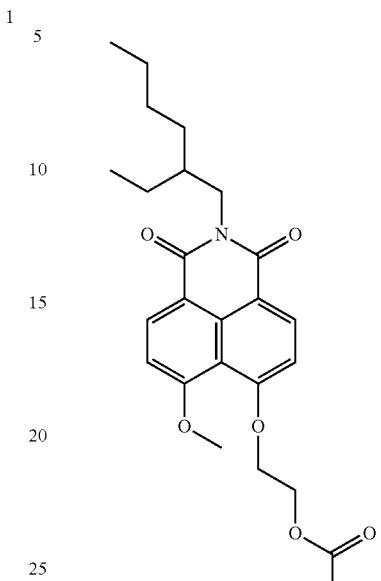
5
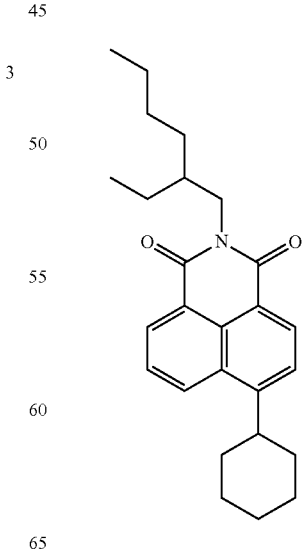

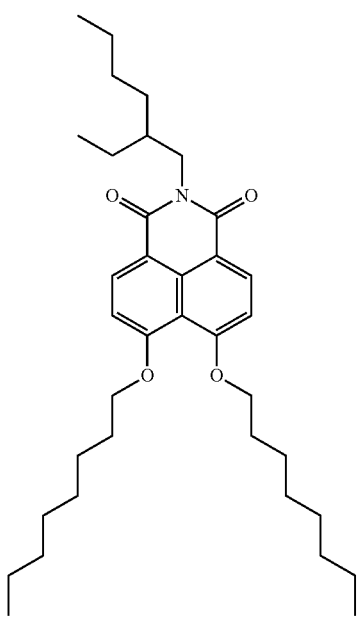
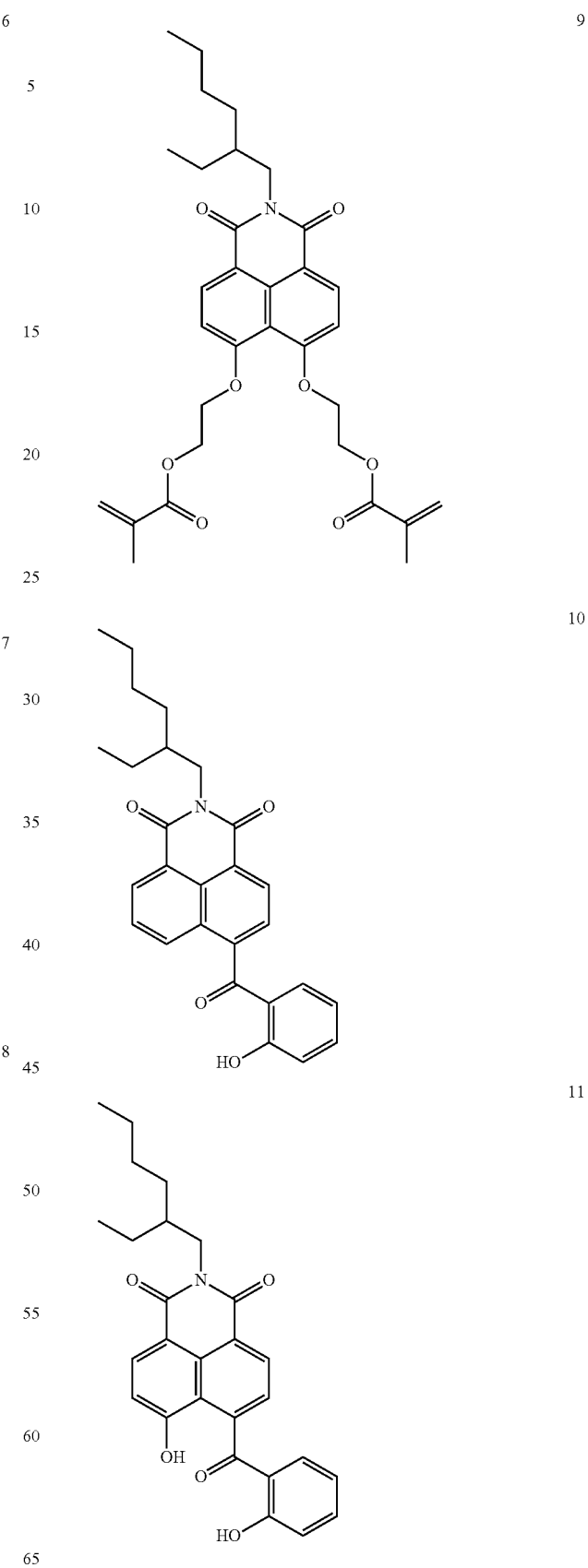

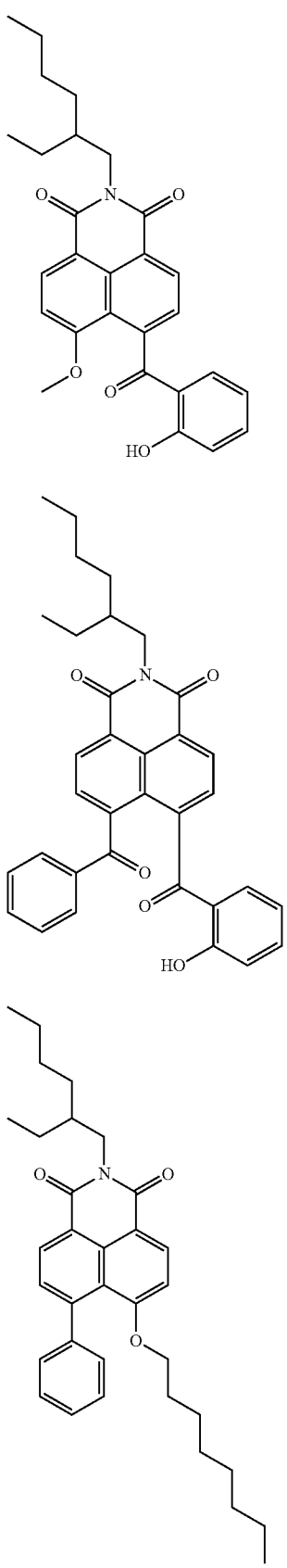
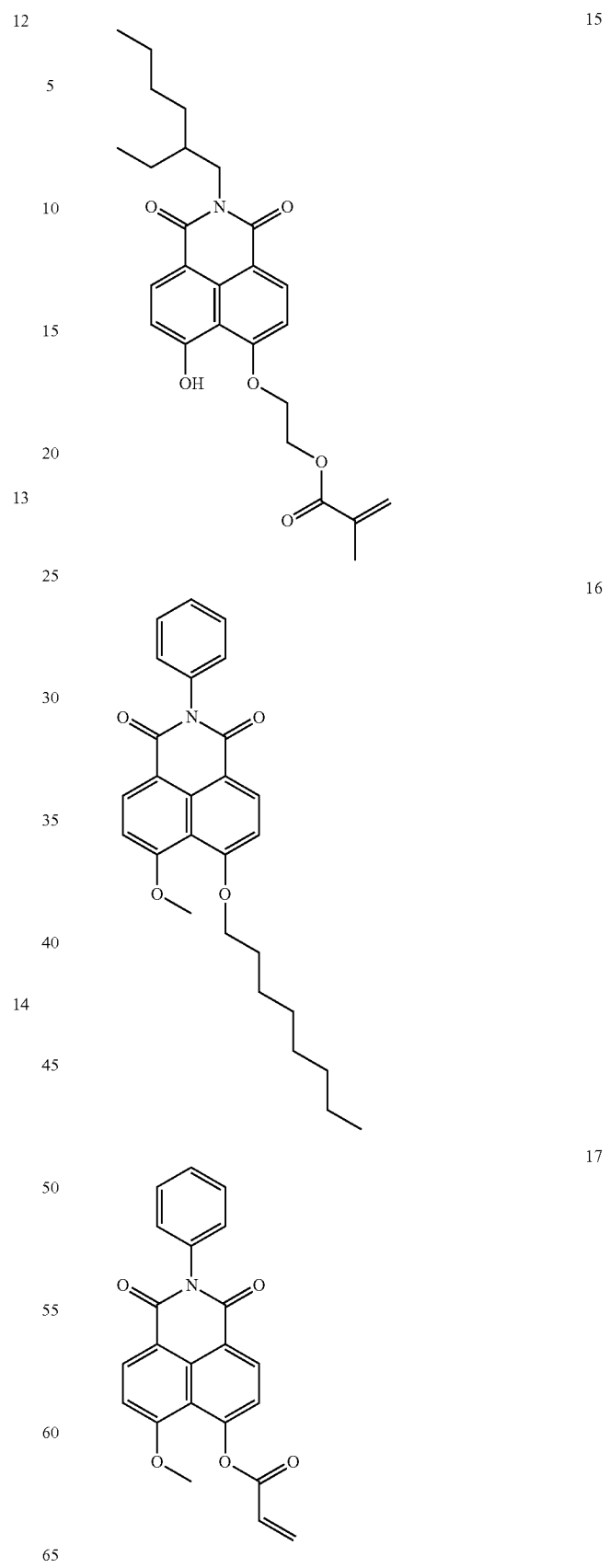

18
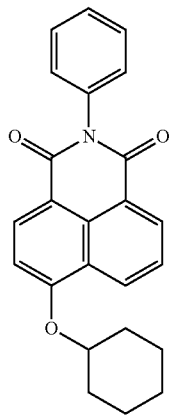
19
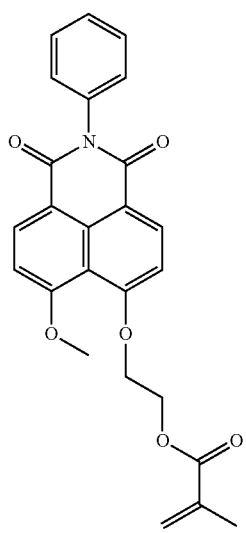
20
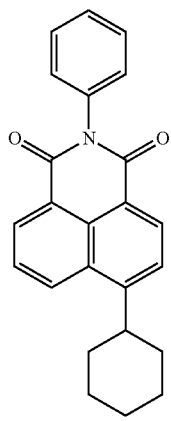
21
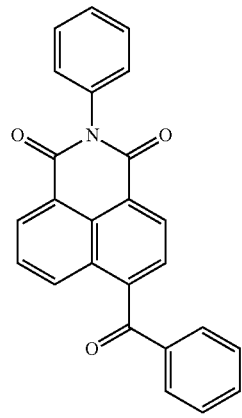
22
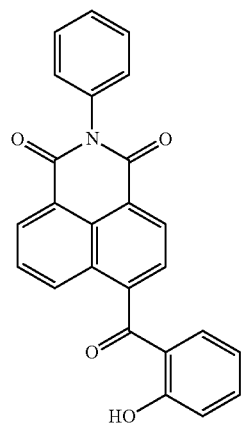
23
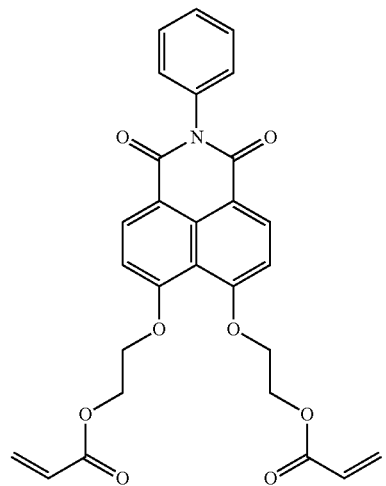

24
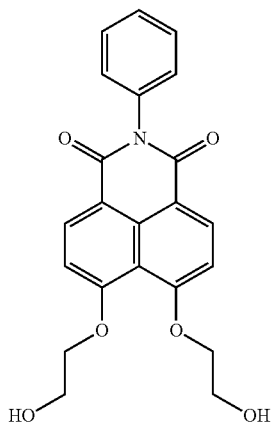
25
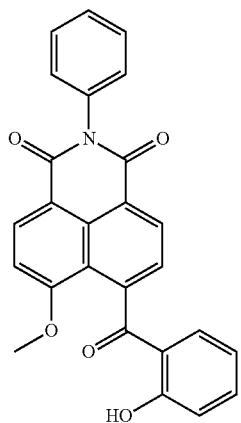
26
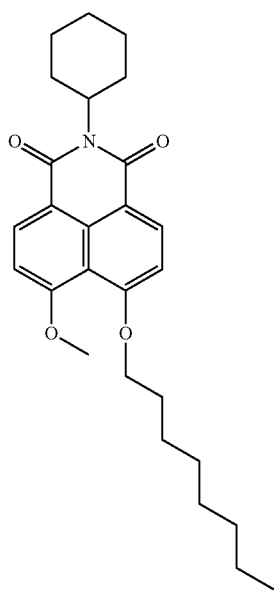
27
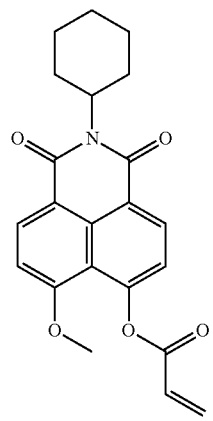
28
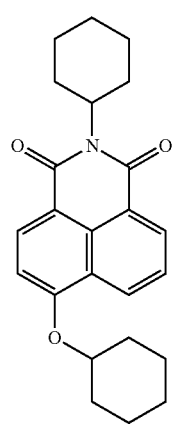
28
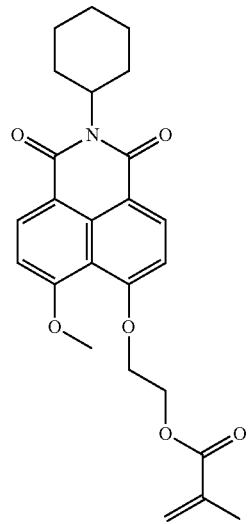

29
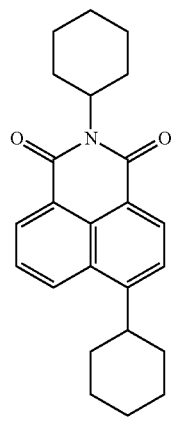
30
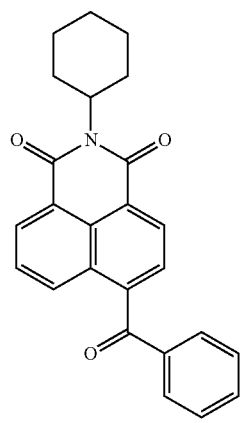
31
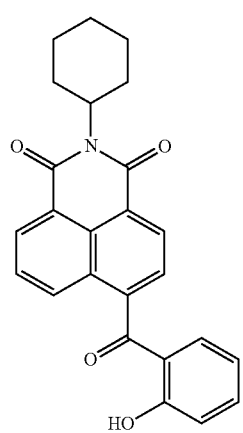
33
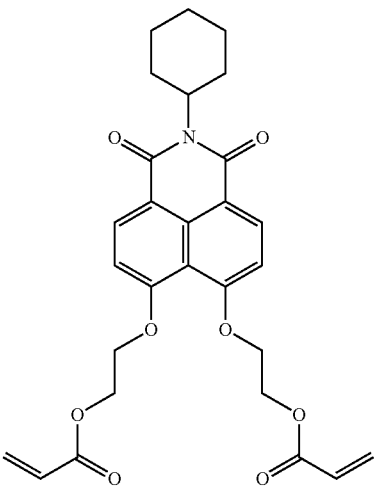
34
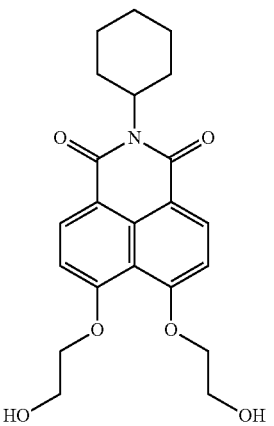
35
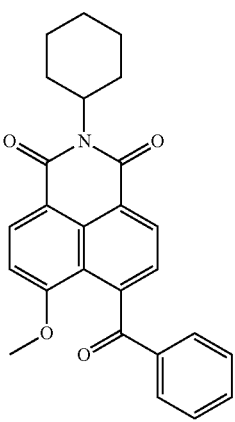

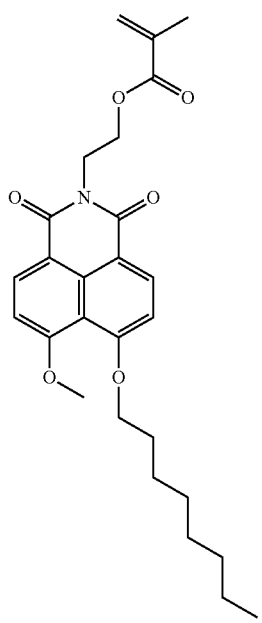
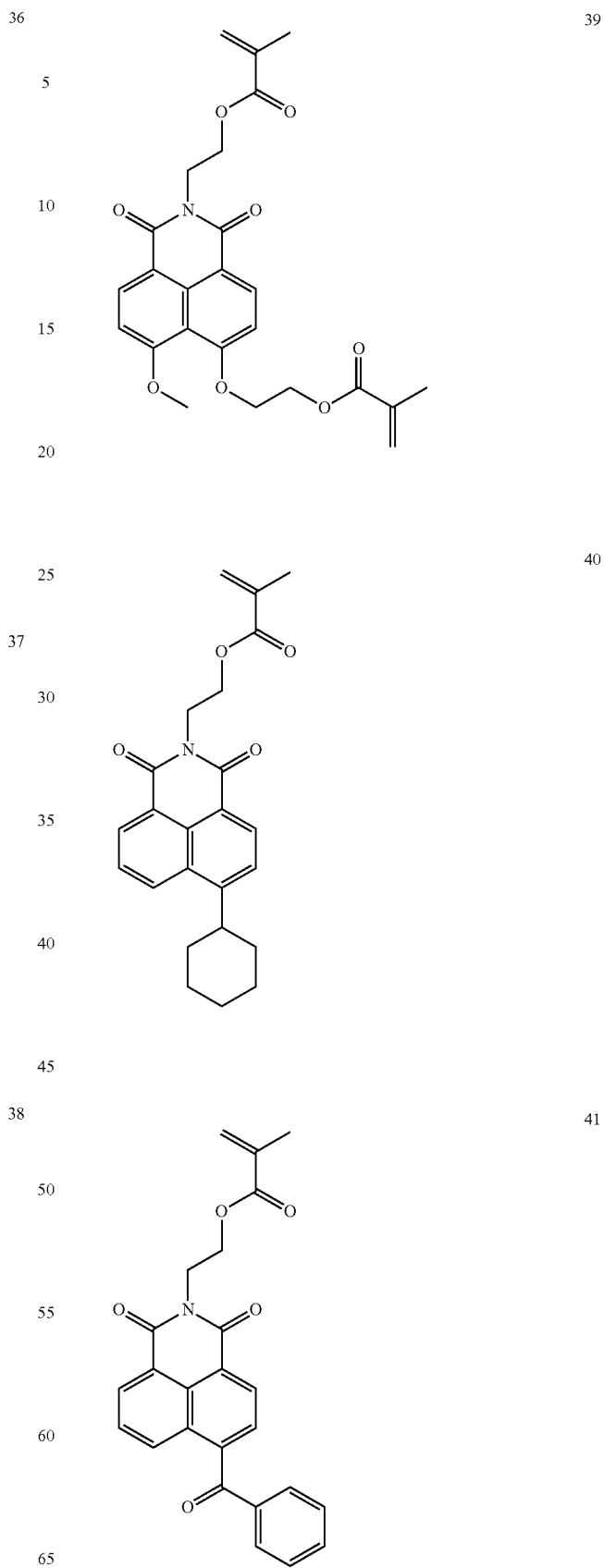

42
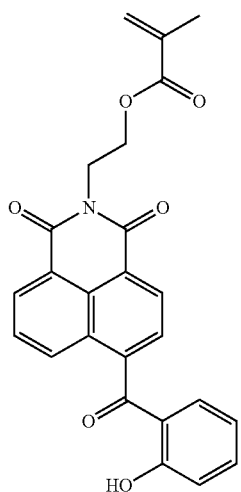
43
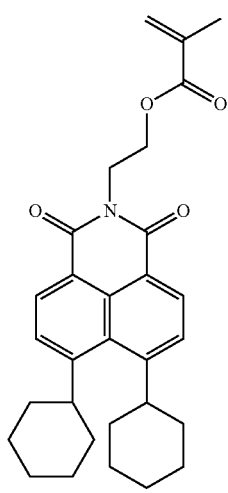
44
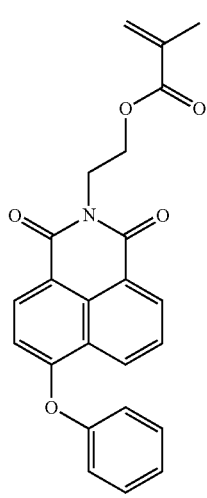
45
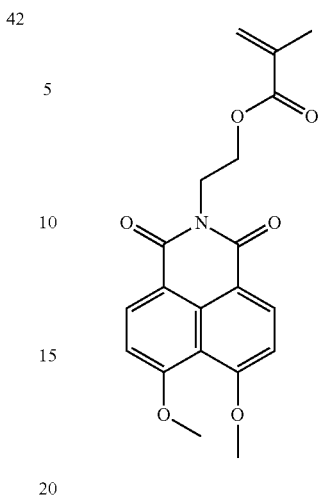
46
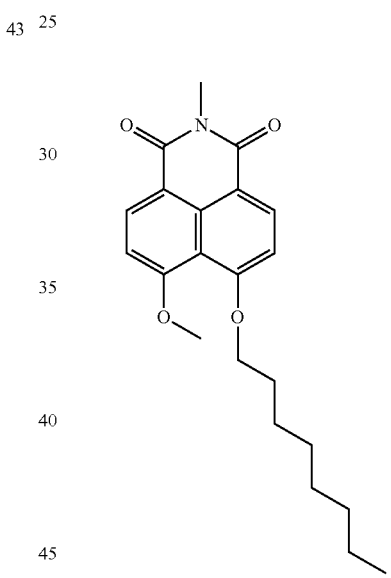
47
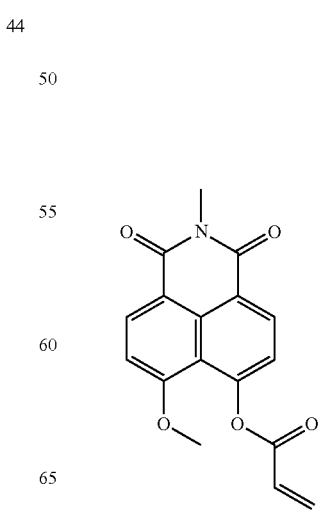

48
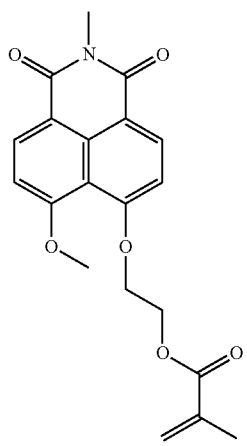
49
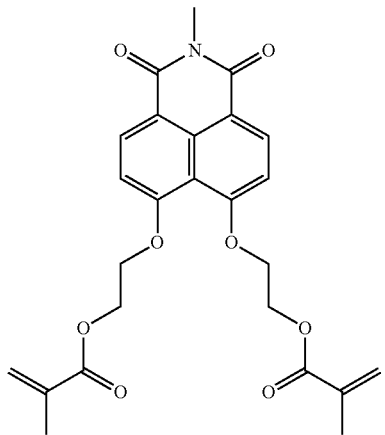
50
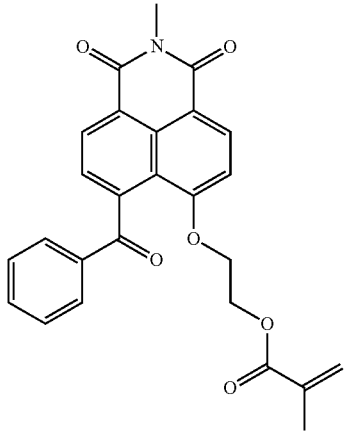
51
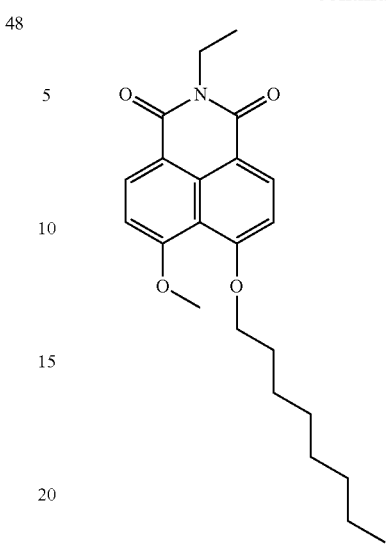
52
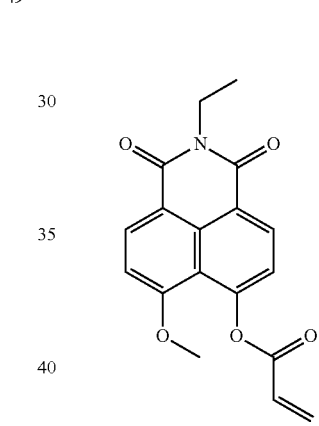
53
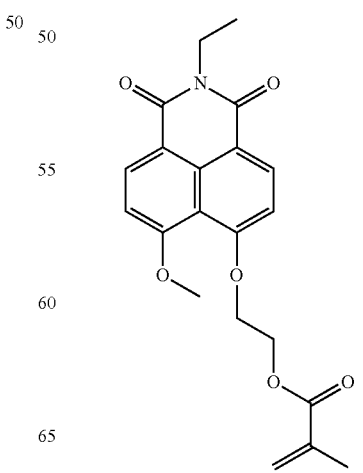

54
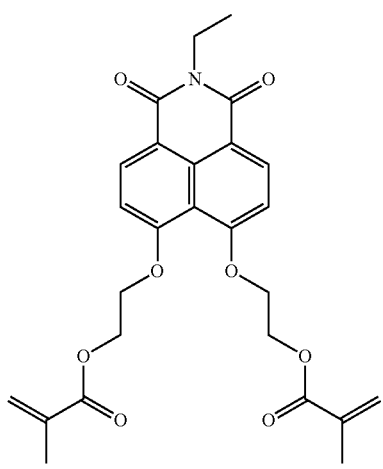
55
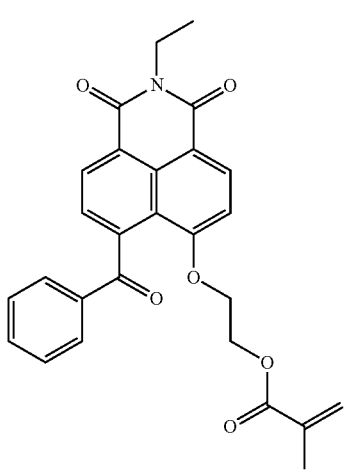
56
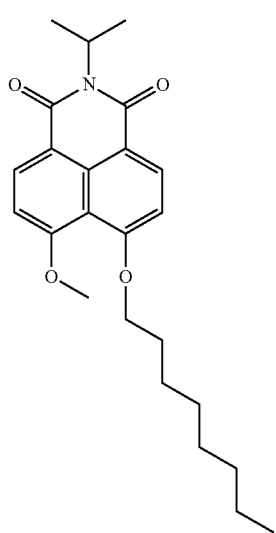
57
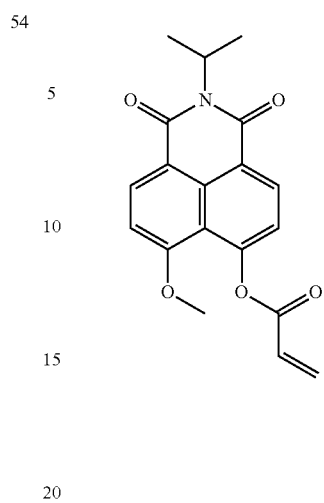
58
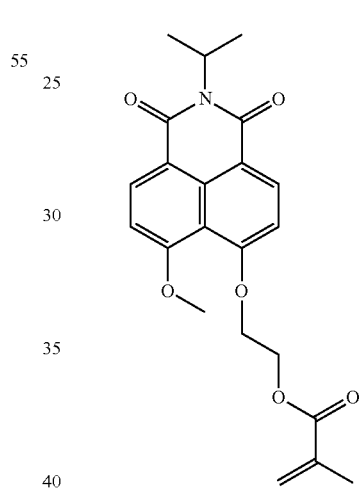
59
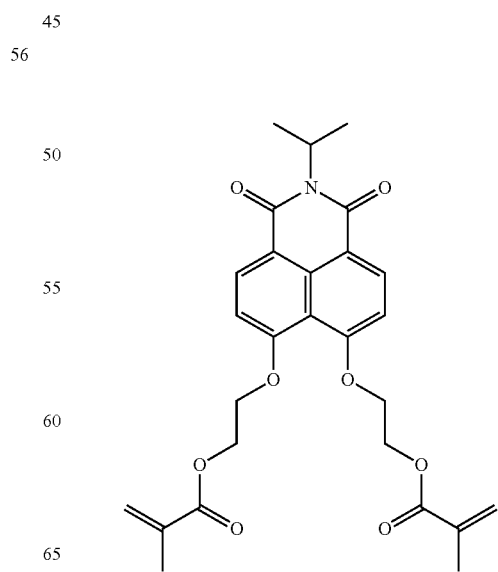

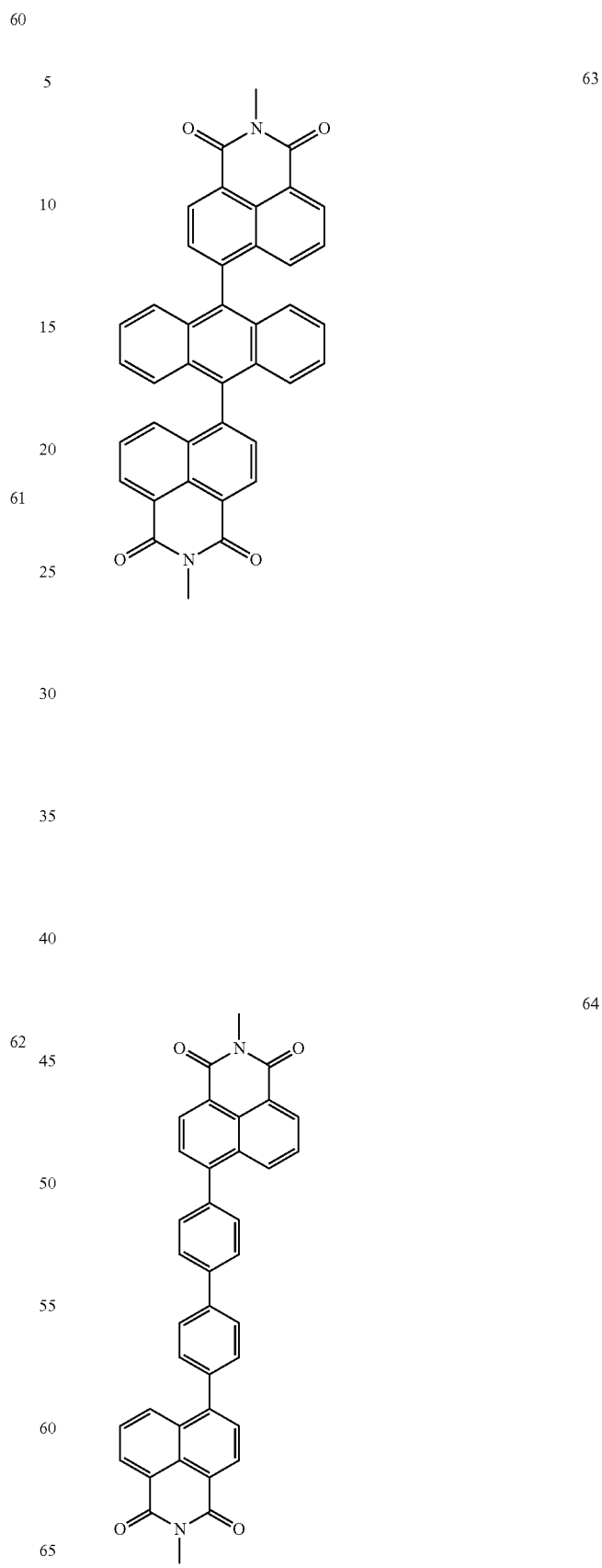
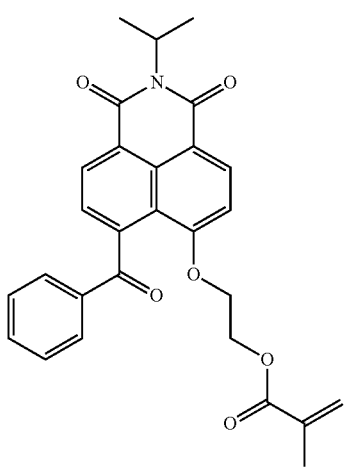

181
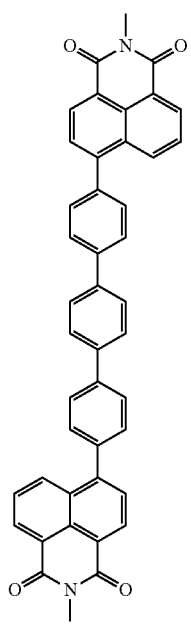
182
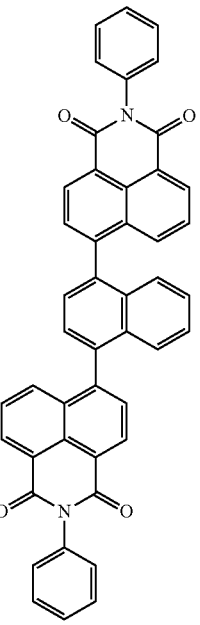
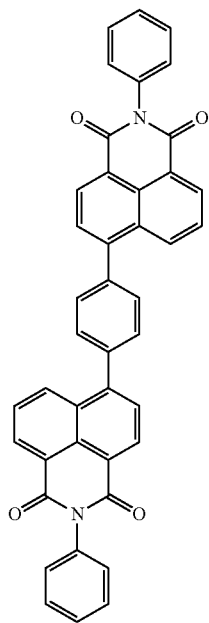
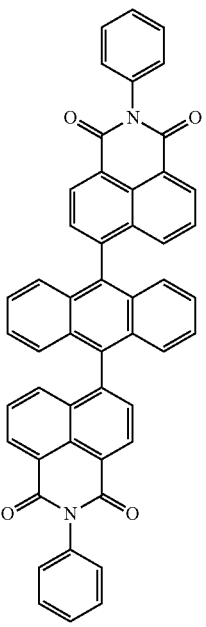

183
-continued
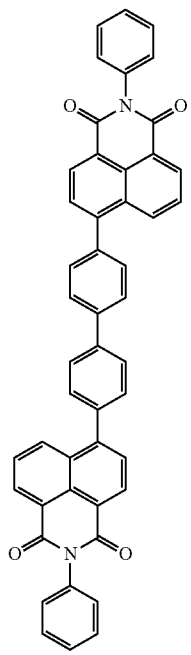
184
-continued
69
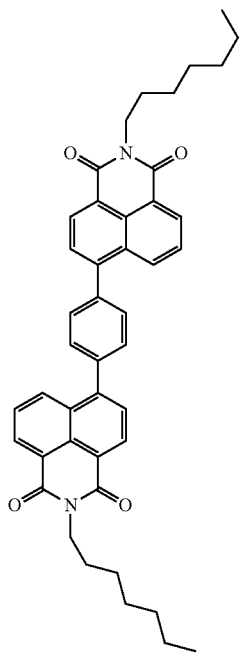
70
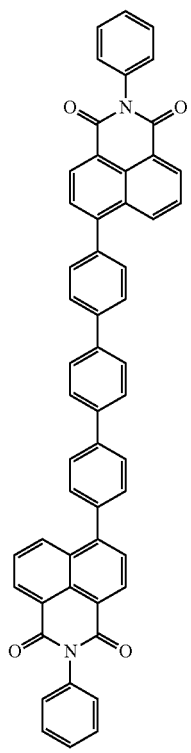
71
72
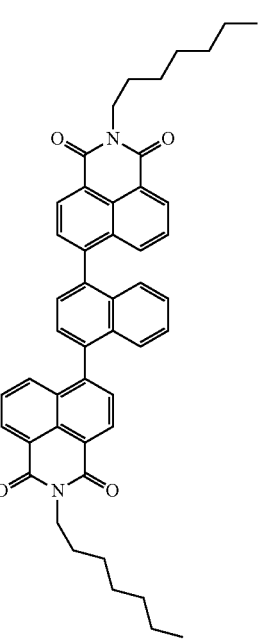

185
-continued
73
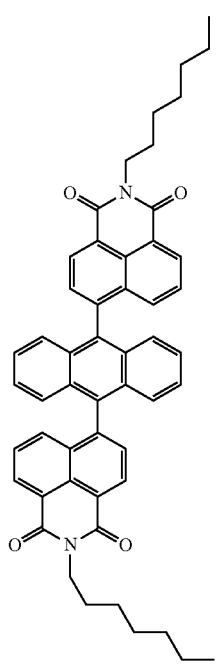
74
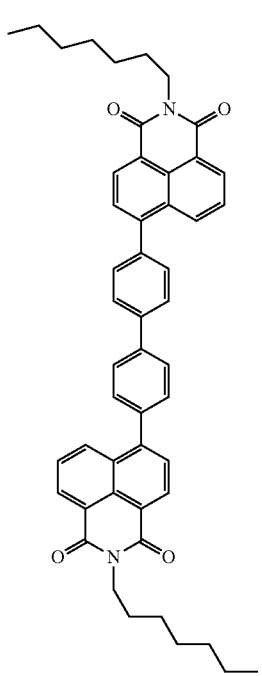
186
-continued
75
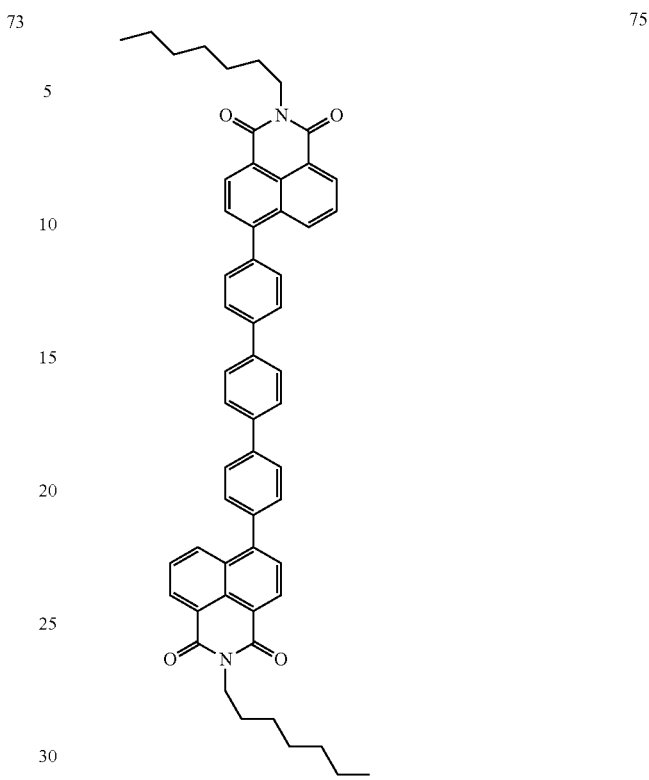
76
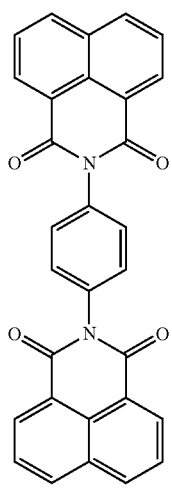

187
-continued
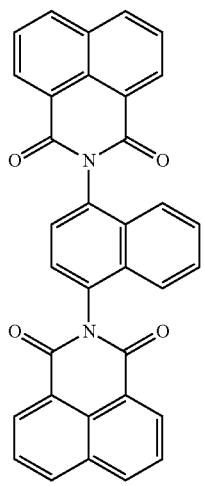
77
188
-continued
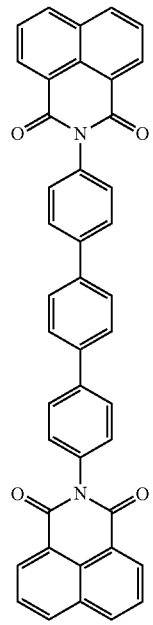
79
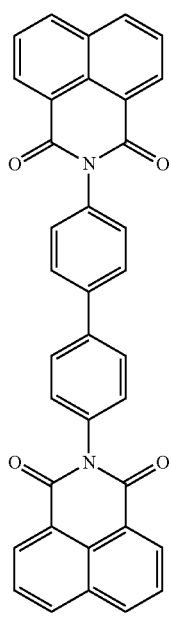
78
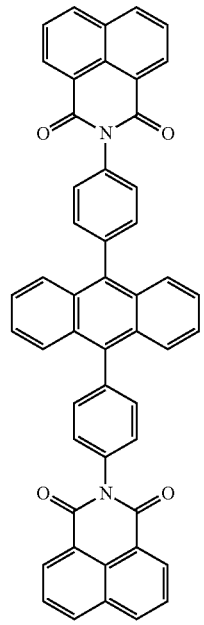
80

189
-continued
81
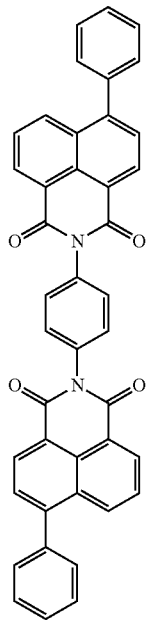
82
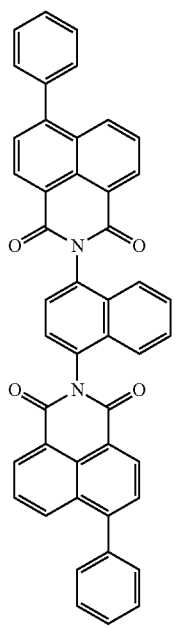
190
-continued
83
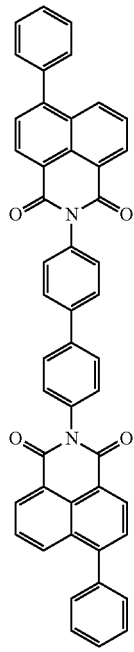
84
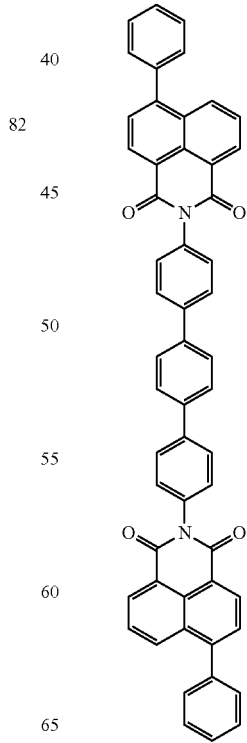

191
-continued
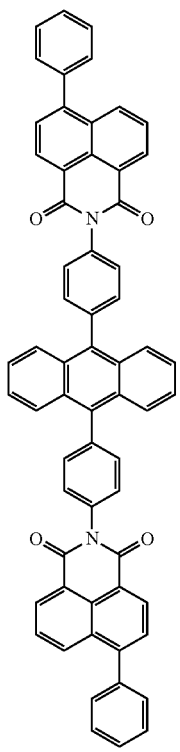
192
-continued
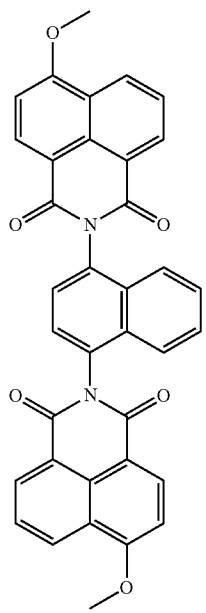
86
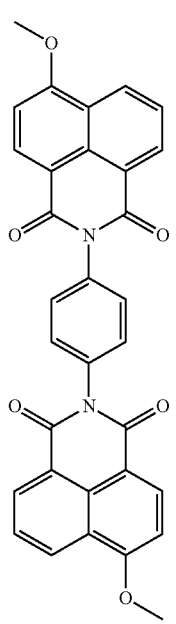
85
87
88
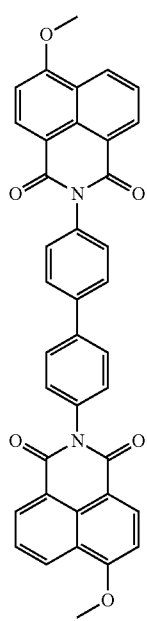

89
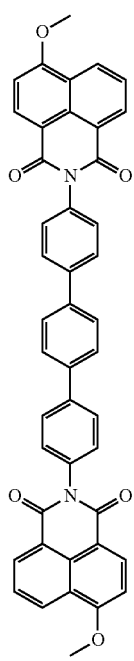
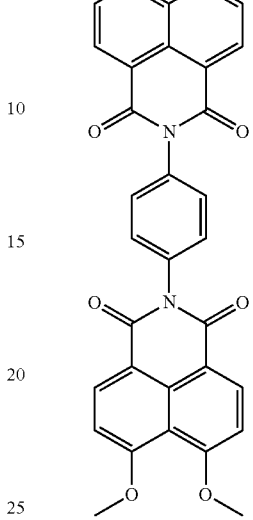
90
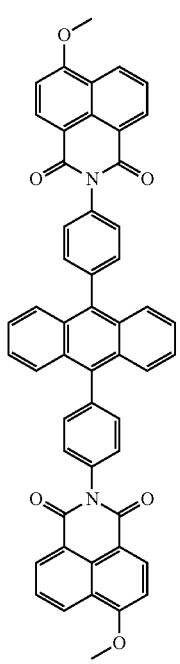
91
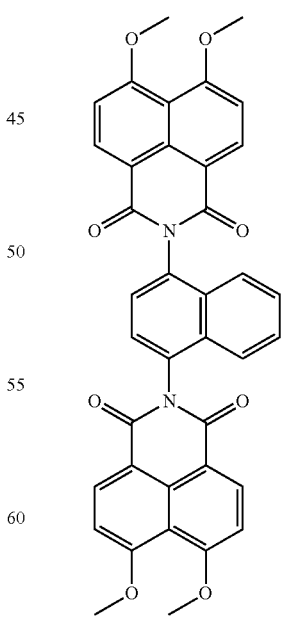
92

195
-continued
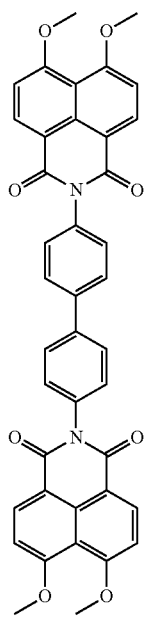
93
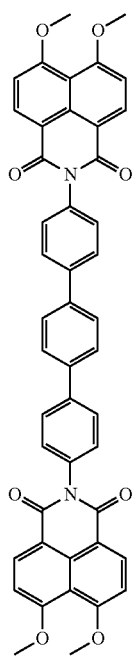
94
196
-continued
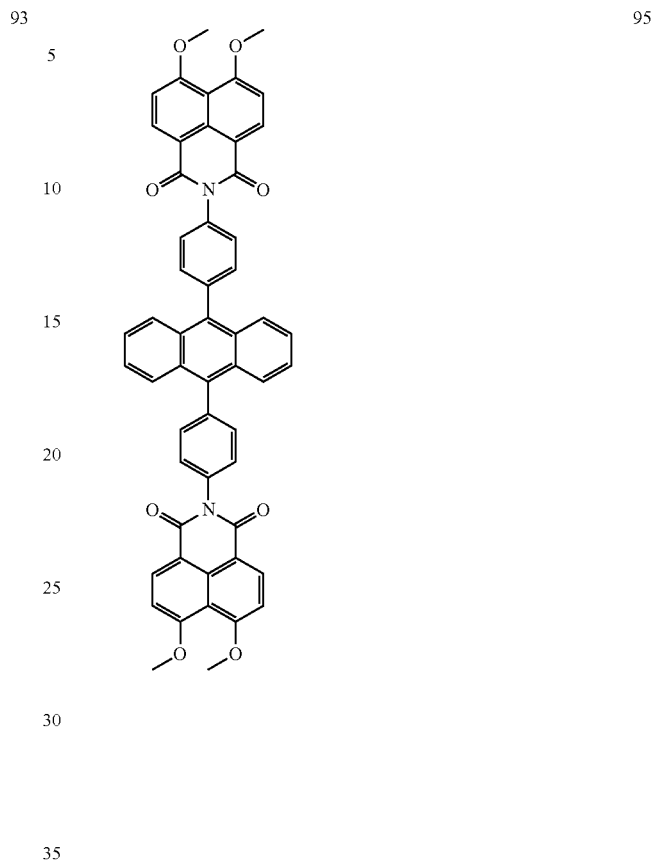
95
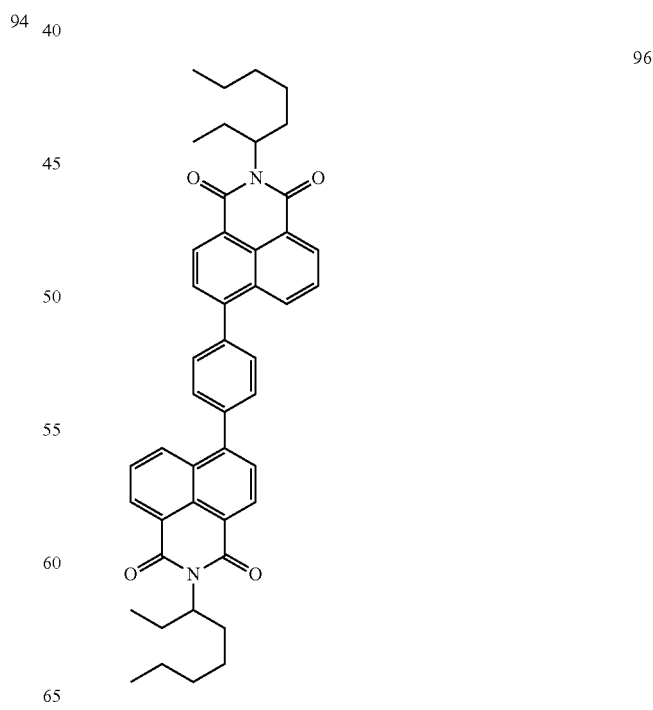
96

197
-continued
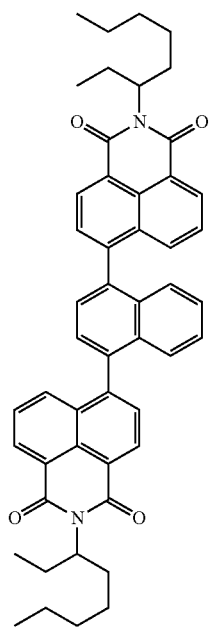
98
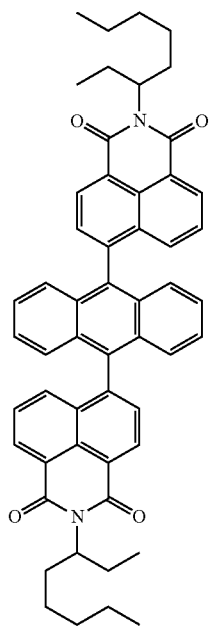
198
-continued
97
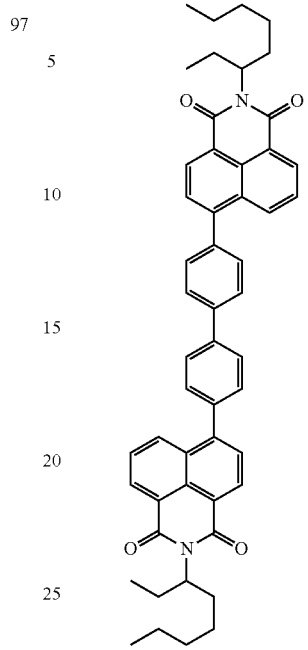
99
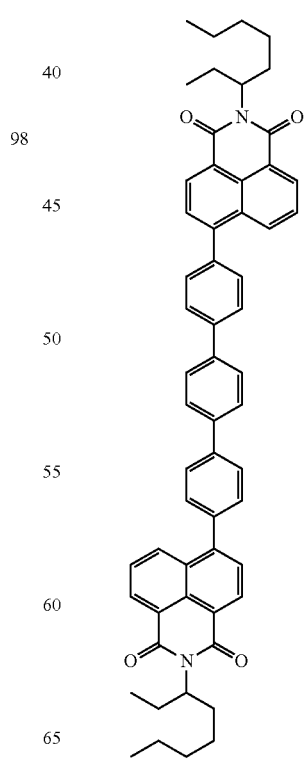
100

199
-continued
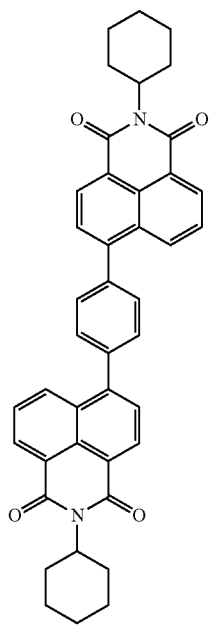
200
-continued
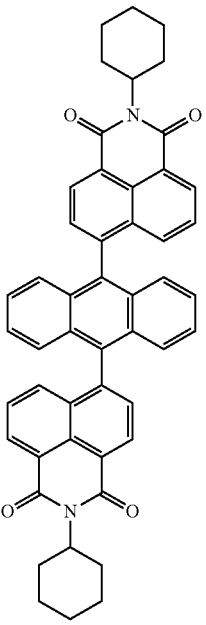
101
102
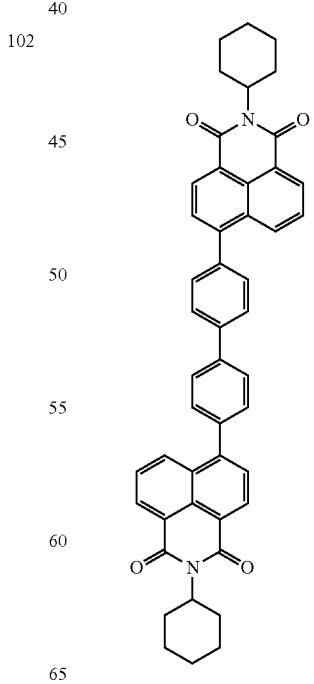
103
104

201
-continued
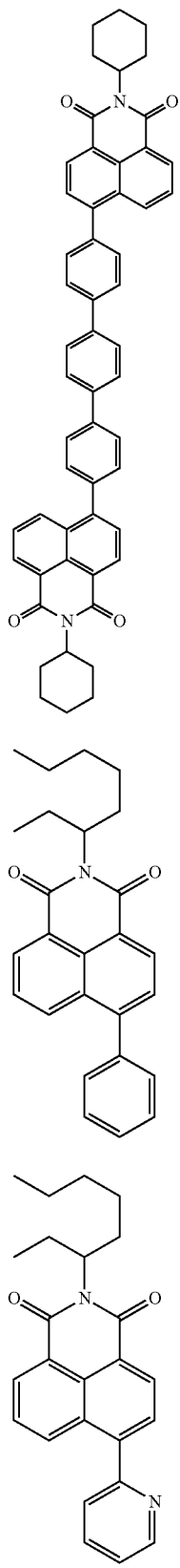
202
-continued
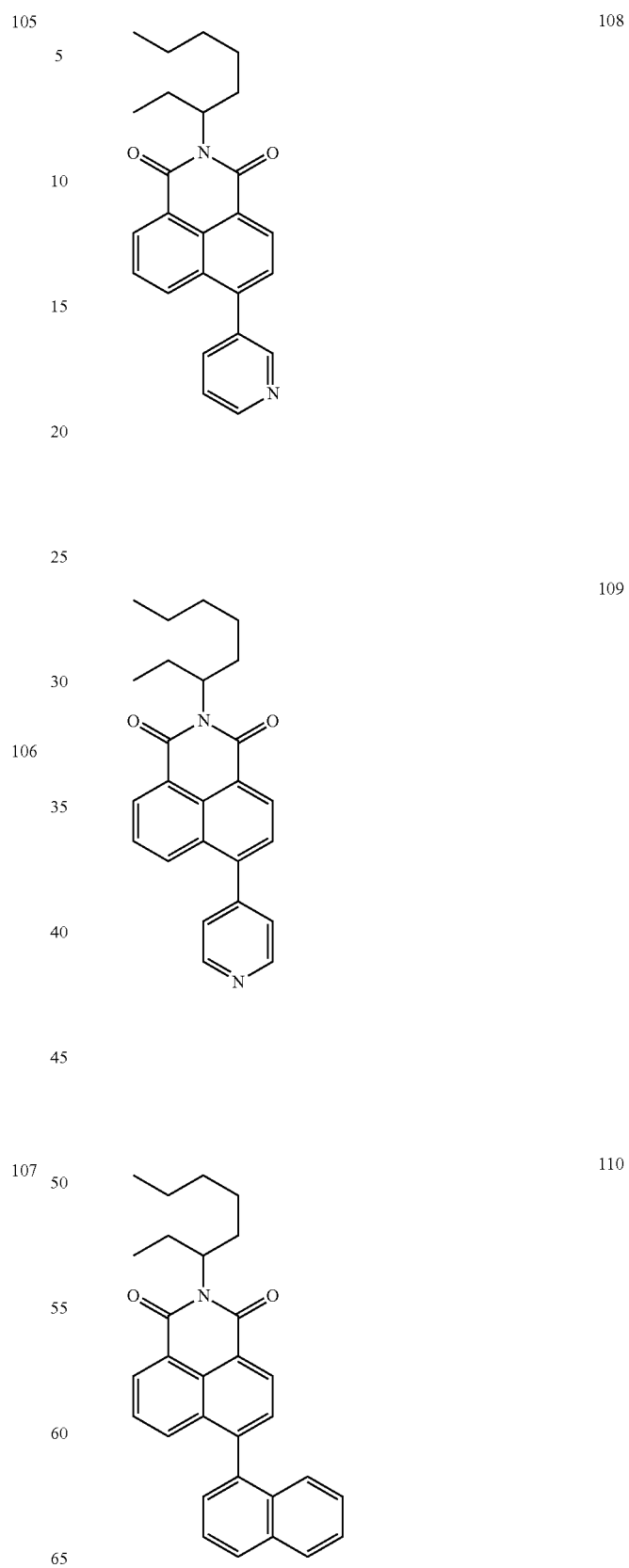

203
-continued
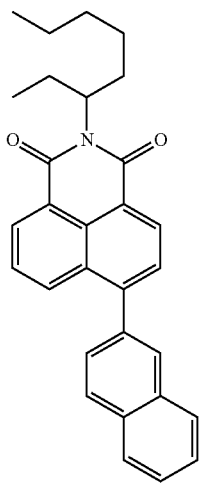
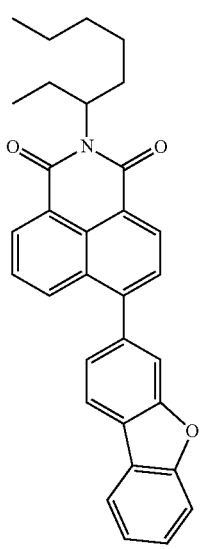
204
-continued
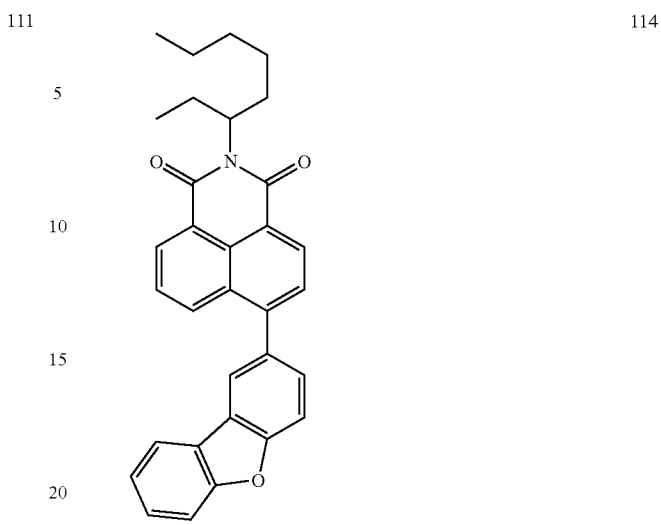
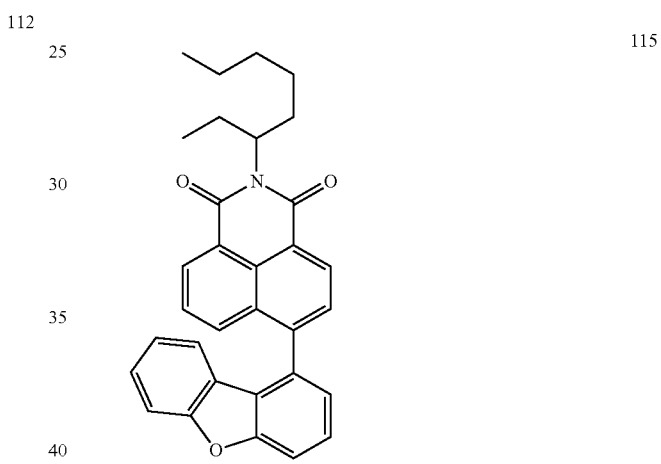
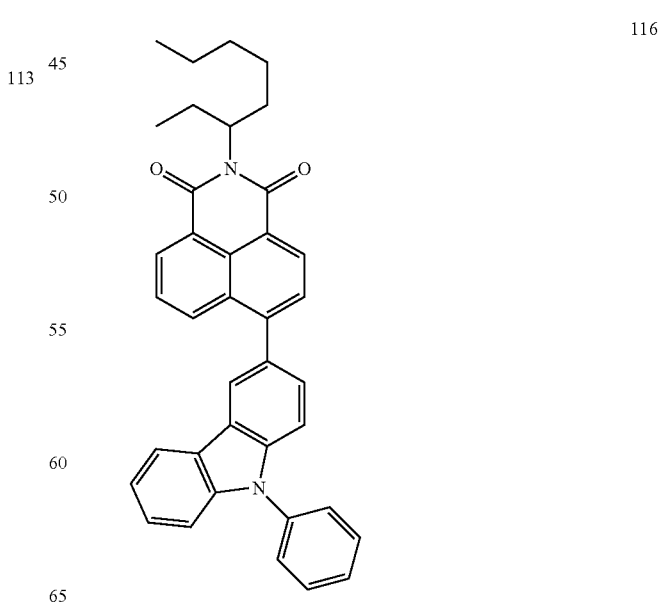

117
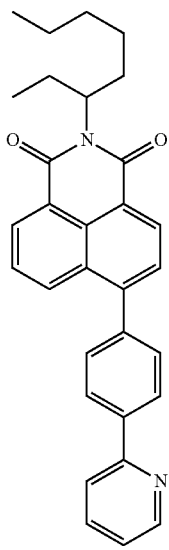
118
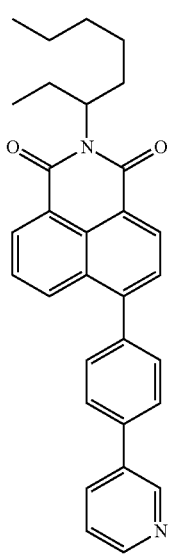
119
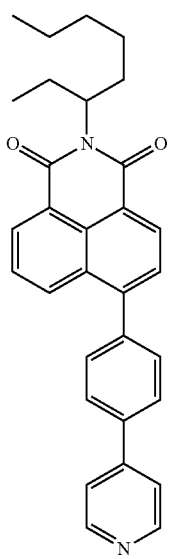
120
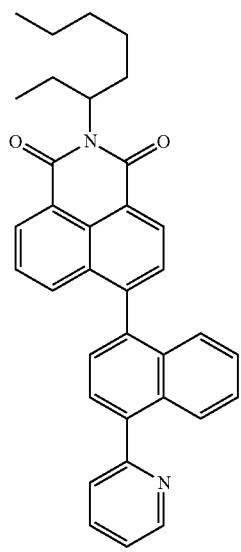
121
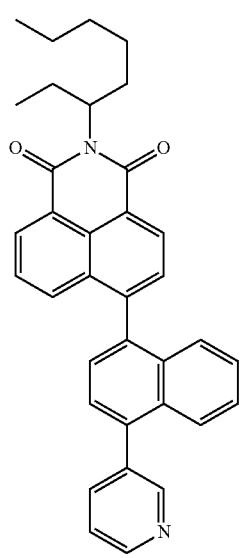
122
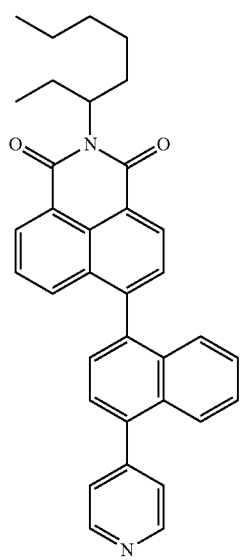

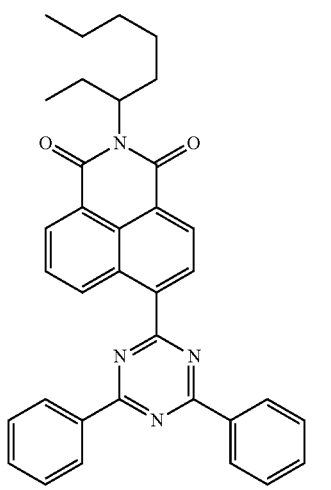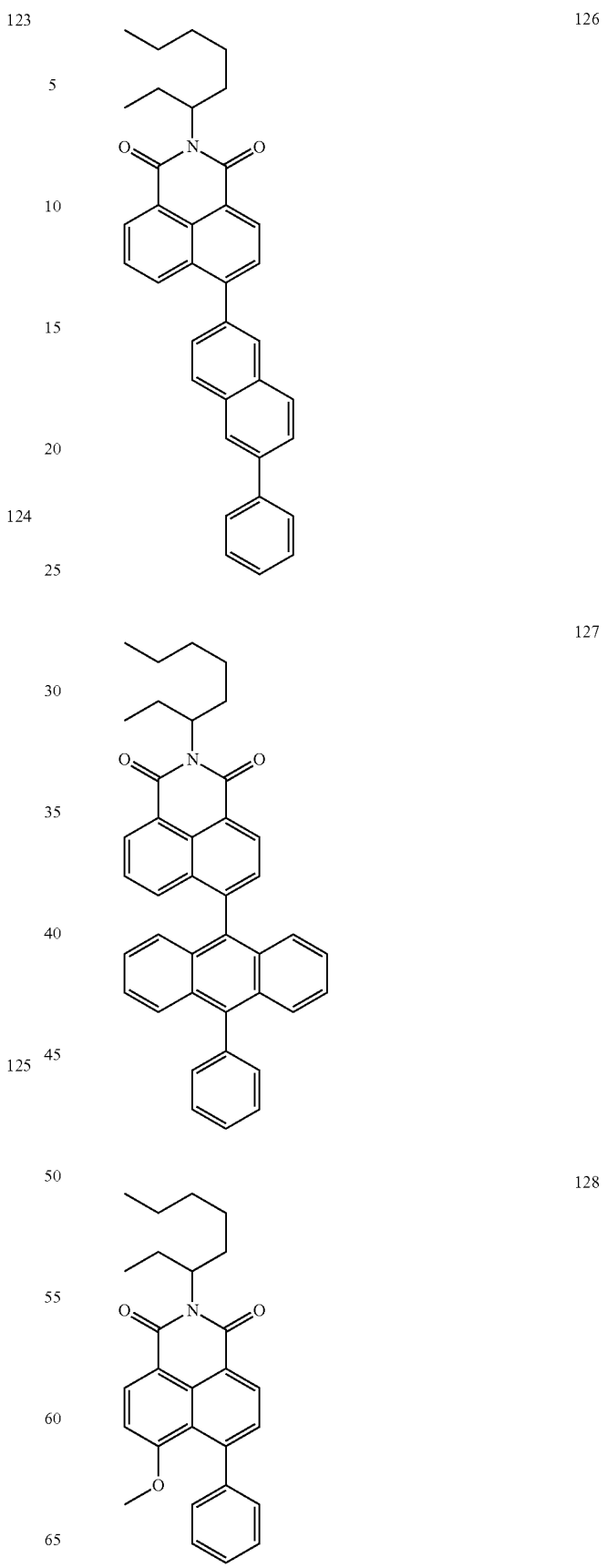

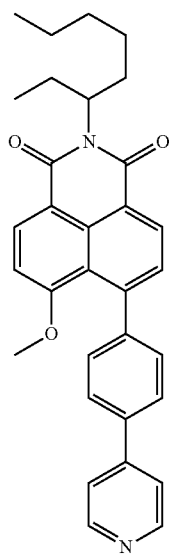
129
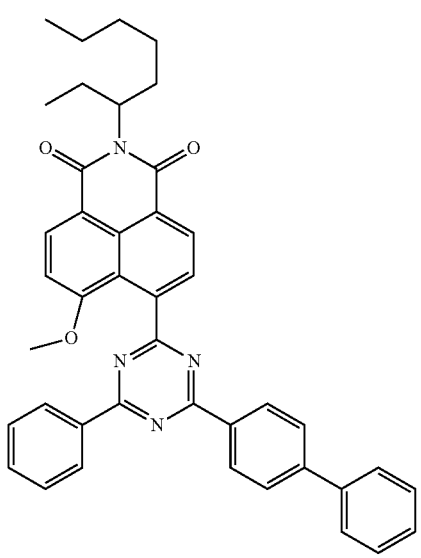
130
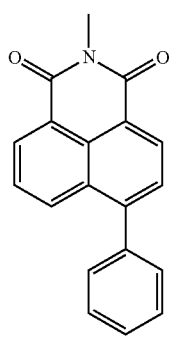
131
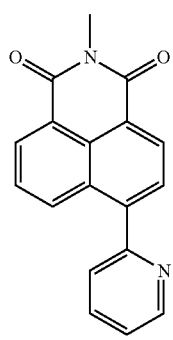
132
133
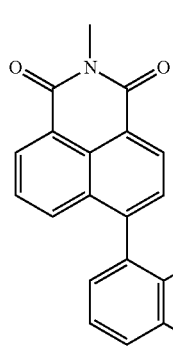
135

211
-continued
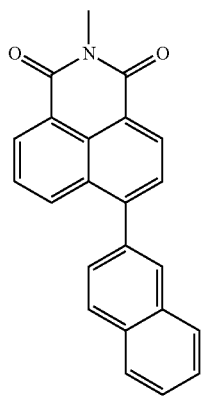
136
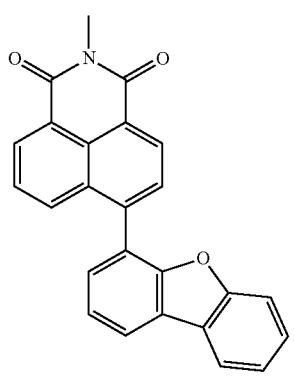
137
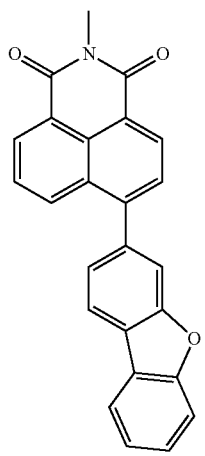
138
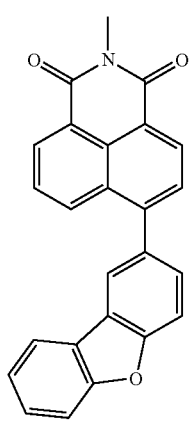
139
212
-continued
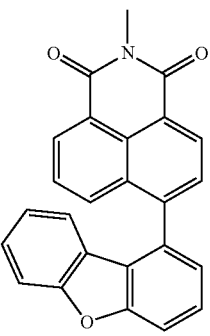
140
141
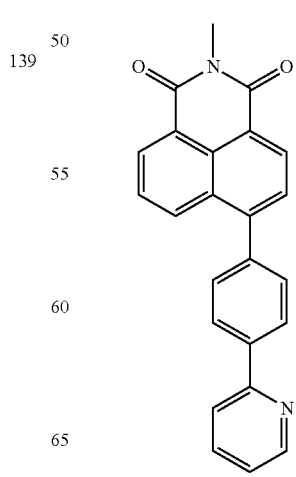
142

213
-continued
143
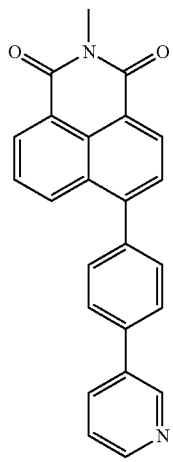
144
145
214
-continued
146
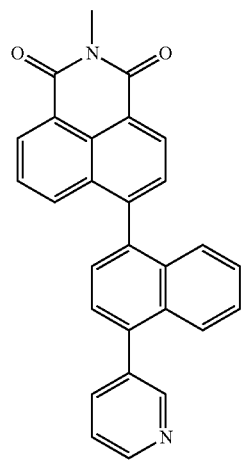
147
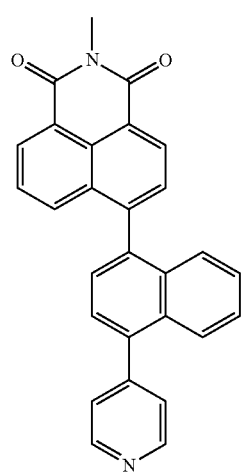
148
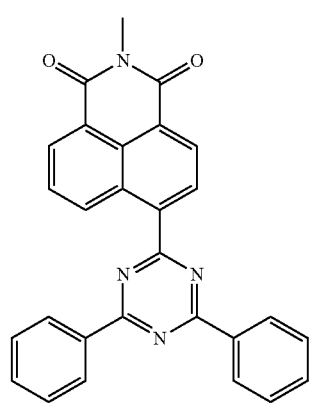
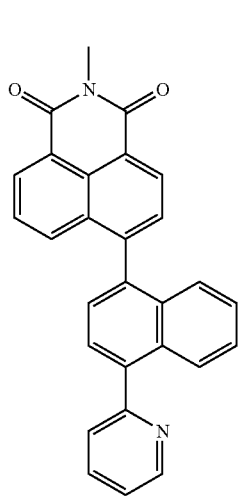

149
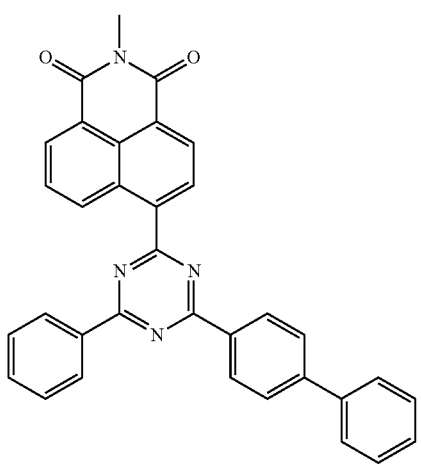
150
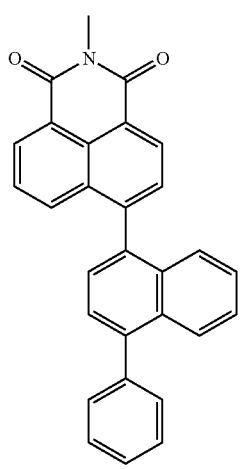
151
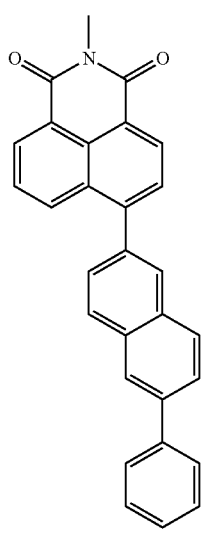
152
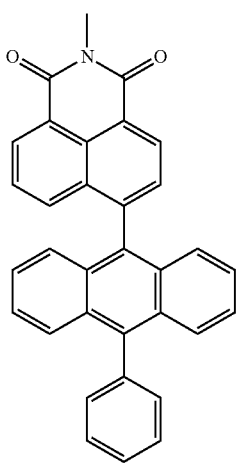
153
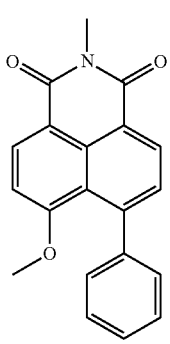
154
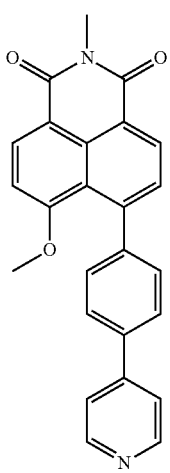

155
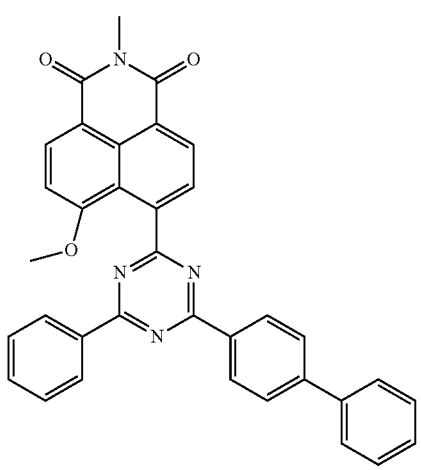
158
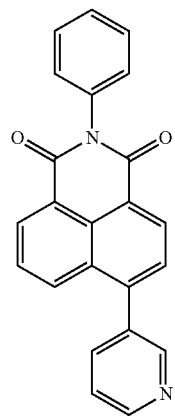
156
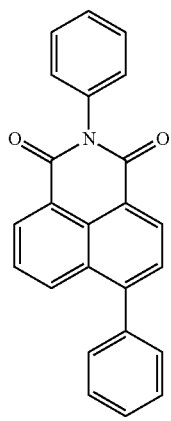
159
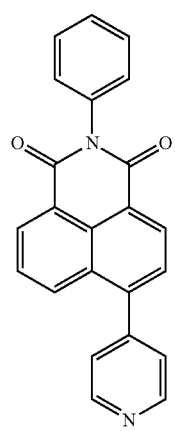
157
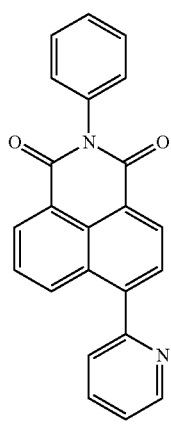
160
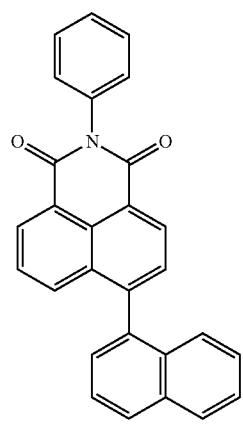

219
-continued
161
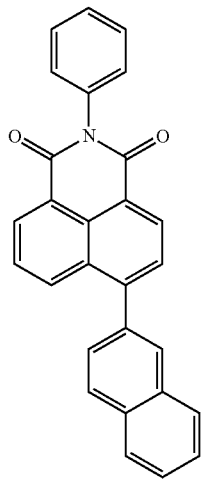
162
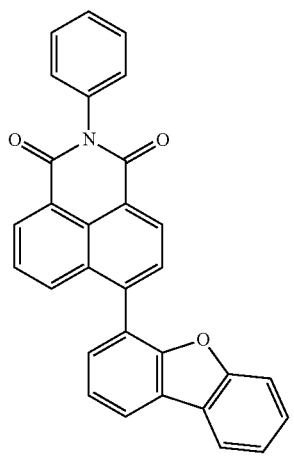
163
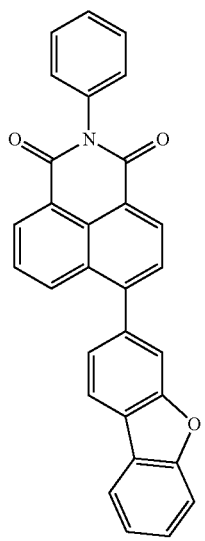
220
-continued
164
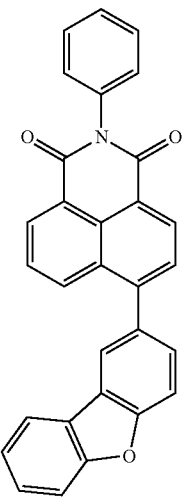
165
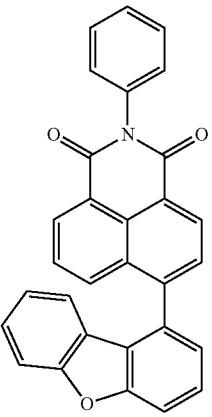
166
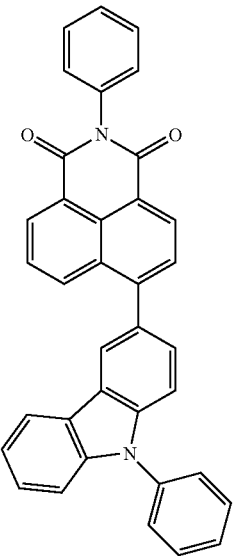

221
-continued
222
-continued
167
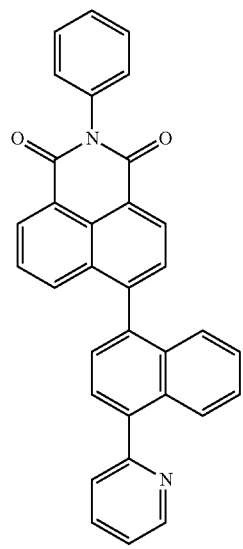
168
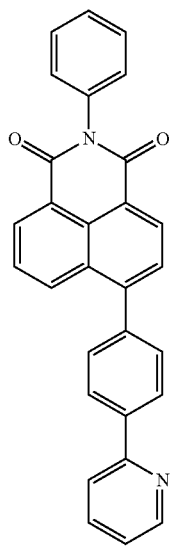
169
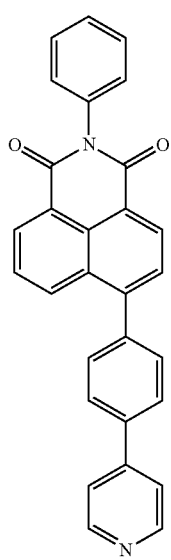
170
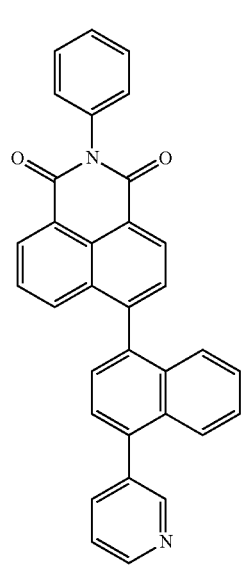
171
172
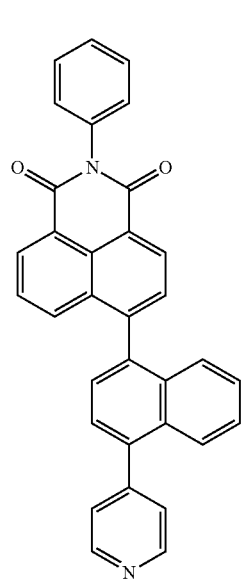

173
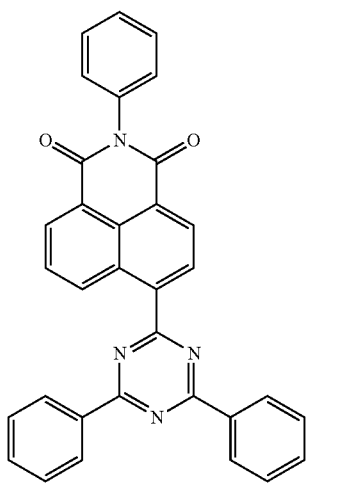
174
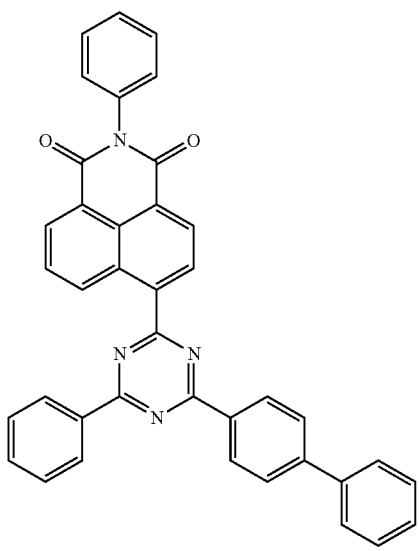
175
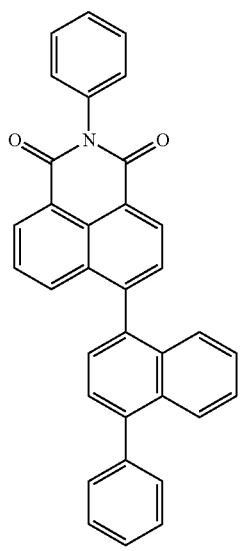
176
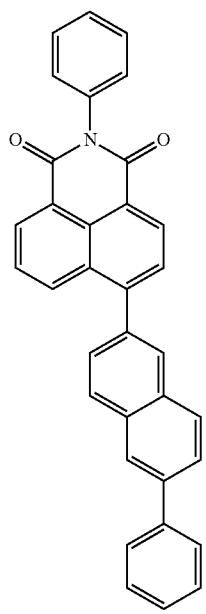
177
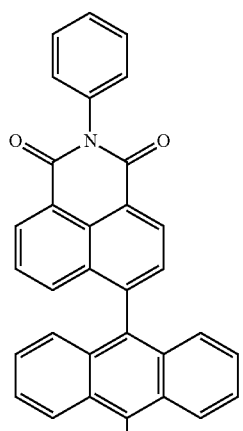
178
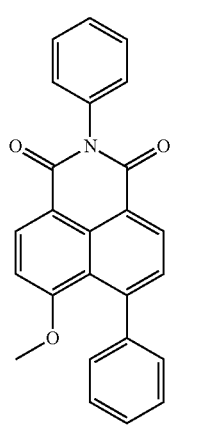

225 226
-continued -continued
179
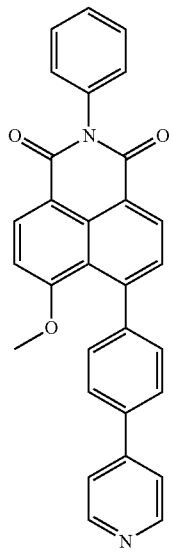
182
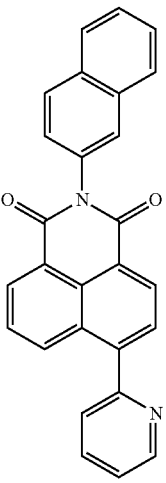
180
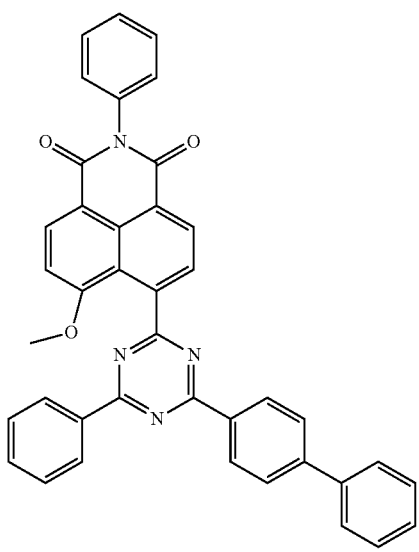
183
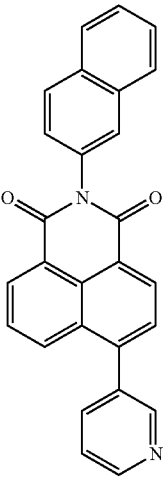
181
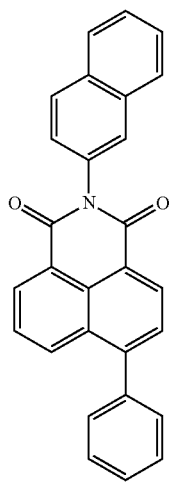
184
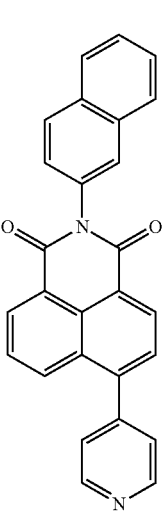

227
-continued
185
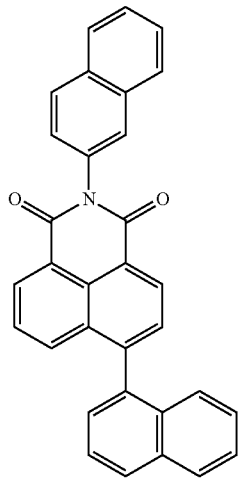
186
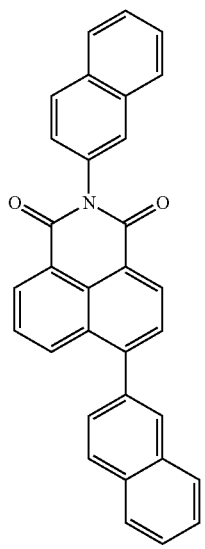
187
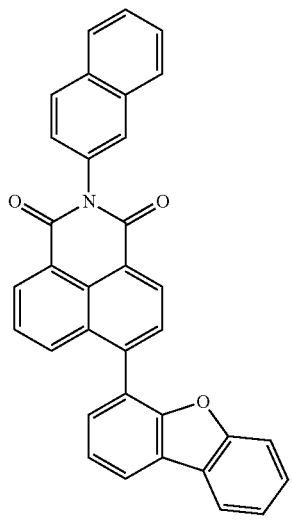
228
-continued
188
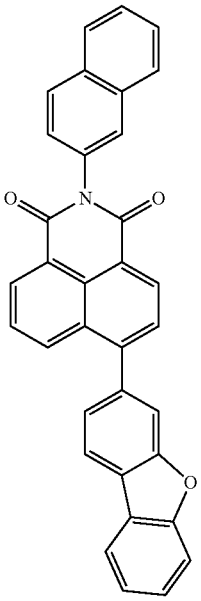
189
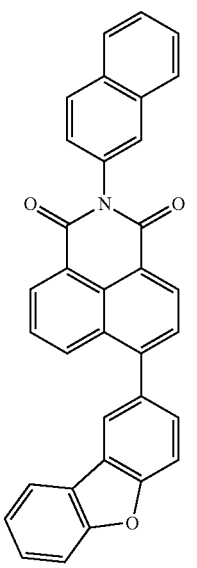
190
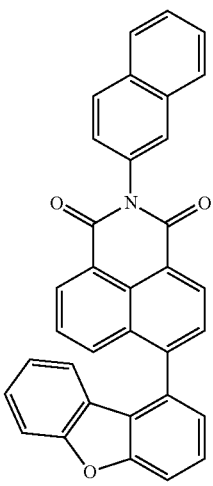

229
-continued
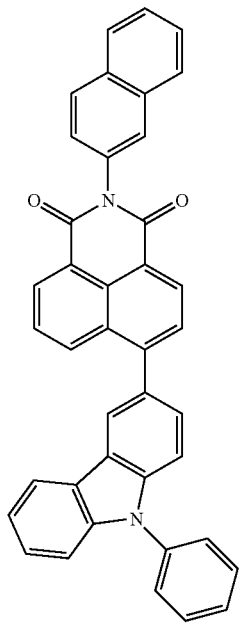
191
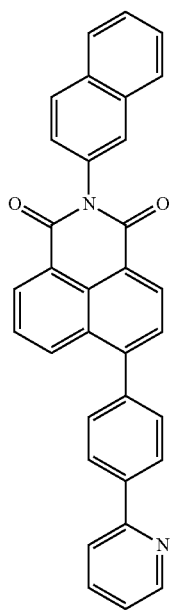
192
230
-continued
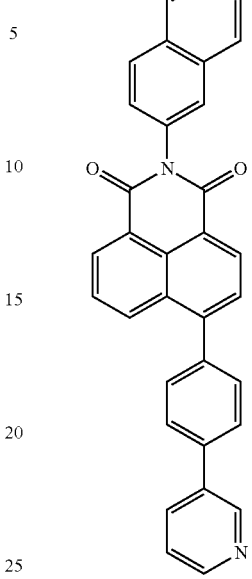
193
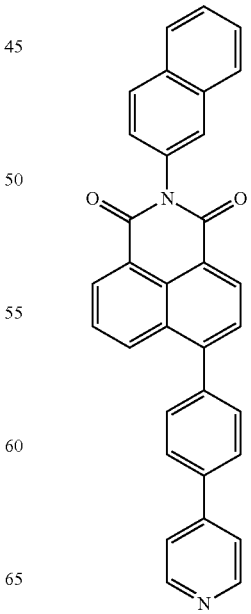
194

231
-continued
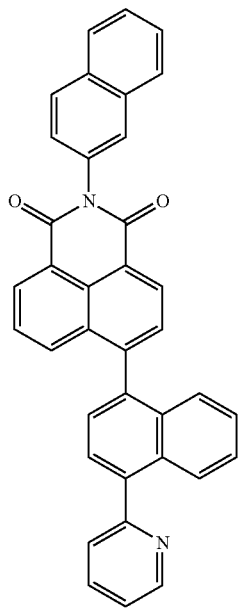
195
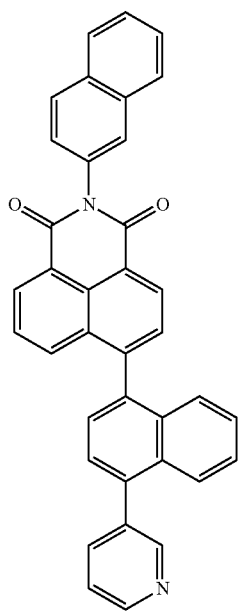
196
232
-continued
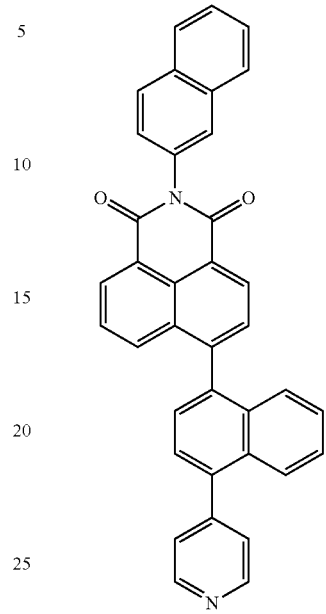
197
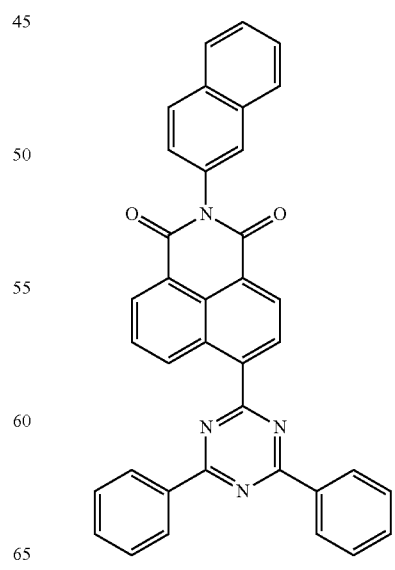
198

199
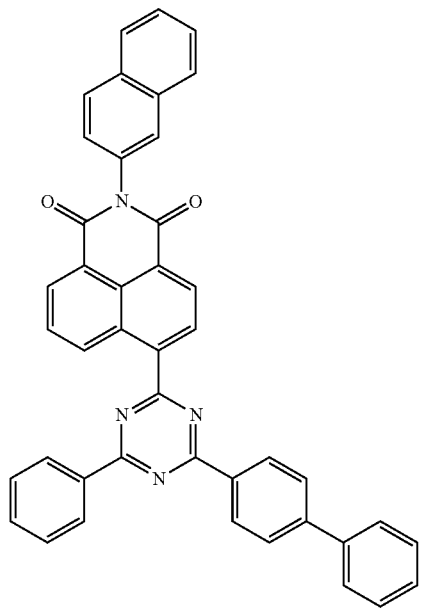
201
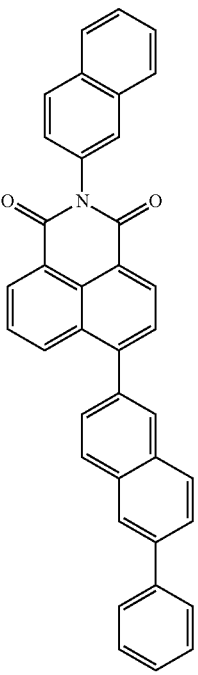
200
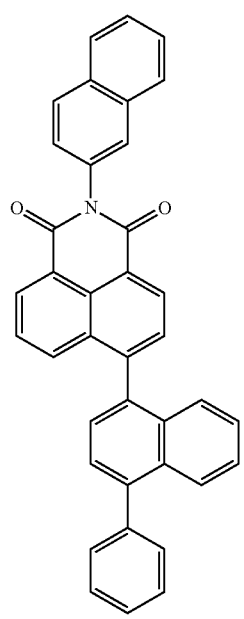
202
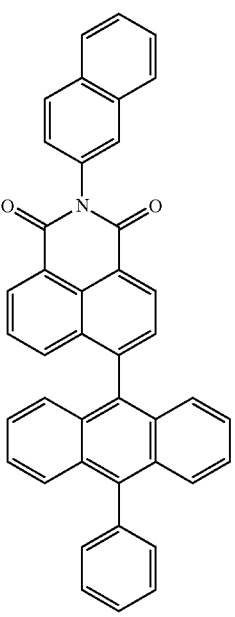

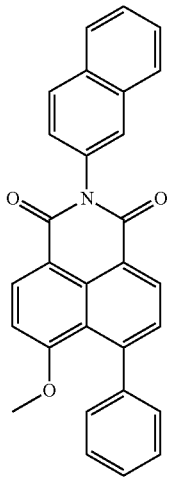

203

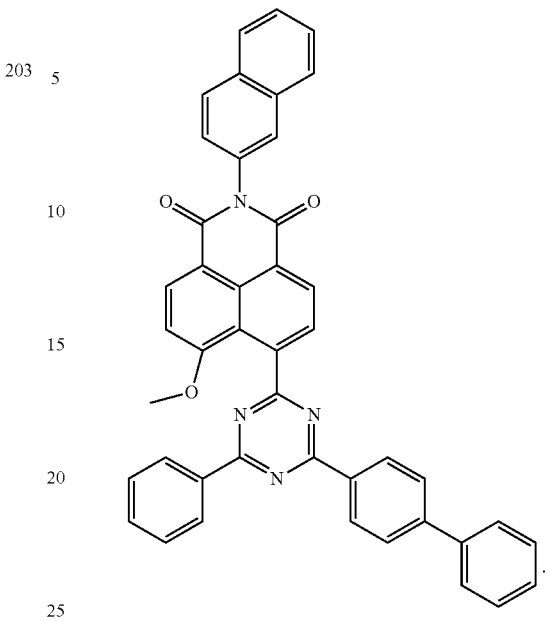

205

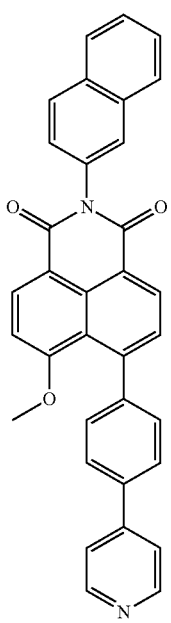

204

11. The organic light-emitting display apparatus of claim 1, wherein
the first compound is configured to absorb light having a wavelength of about 400 nm to about 410 nm.

12. The organic light-emitting display apparatus of claim 1, wherein
the encapsulation unit further comprises a second compound different from the first compound, and
a wavelength range of light absorbed by the first compound is different from a wavelength range of light absorbed by the second compound.

13. The organic light-emitting display apparatus of claim 1, wherein
the encapsulation unit further comprises a third compound different from the first compound, and
the first compound is dispersed in the third compound.

14. The organic light-emitting display apparatus of claim 13, wherein
the first compound is cross-linked to the third compound.

15. The organic light-emitting display apparatus of claim 1, wherein
the encapsulation unit further comprises a metal, a metal halide, a metal nitride, a metal oxide, a metal oxynitride, a silicon nitride, a silicon oxide, and/or a silicon oxynitride.

16. The organic light-emitting display apparatus of claim 1, wherein
the encapsulation unit comprises at least one organic film and at least one inorganic film, and
the at least one organic film consists of the first compound.

17. The organic light-emitting display apparatus of claim 16, wherein
the at least one inorganic film comprises at least one selected from the group consisting of a metal, a metal halide, a metal nitride, a metal oxide, a metal oxynitride, a silicon nitride, a silicon oxide, and a silicon oxynitride.

18. The organic light-emitting display apparatus of claim 16, wherein the at least one organic film comprises a first organic film,
the at least one inorganic film comprises a first inorganic film, and
the first organic film is between the organic light-emitting device and the first inorganic film.

19. The organic light-emitting display apparatus of claim 16, wherein
the at least one organic film comprises a first organic film,
the at least one inorganic film comprises a first inorganic film, and
the first inorganic film is between the organic light-emitting device and the first organic film.

20. An organic light-emitting display apparatus comprising:
a substrate;
an organic emission unit on the substrate and comprising a plurality of organic light-emitting devices; and
an encapsulation unit on the organic emission unit and configured to seal the organic emission unit,
wherein the encapsulation unit comprises a first compound represented by Formula 1:

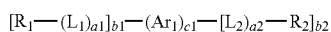

Formula 1

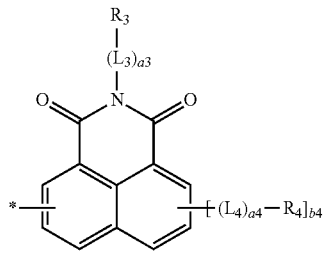

Formula 201

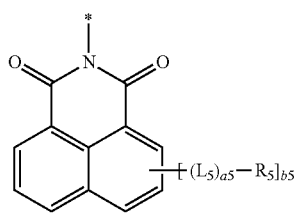

Formula 202

Formula 2-3

Formula 2-4 wherein, in Formulae 1 and 2-1 to 2-4,
$Ar_1$ is a $C_5$-$C_{60}$ carbocyclic group or a $C_2$-$C_{30}$ heterocyclic group,
c1 is 0 or 1,
$L_1$ to $L_5$ and $L_9$ are each independently selected from *—N($R_{11}$)—*', *—B($R_{11}$)—*', *—P($R_{11}$)—*', *—Si($R_{11}$)($R_{12}$)—*', *—S—*', *—Se—*', *—O—*', *—C(=O)—*', *—S(=O)—*', *—S(=O)$_2$—*', *—C($R_{11}$)=*', *—C(=S)—*', a substituted or unsubstituted $C_1$-$C_{60}$ alkylene group, a substituted or unsubstituted $C_2$-$C_{60}$ alkenylene group, a substituted or unsubstituted $C_2$-$C_{60}$ alkynylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
a1 to a5 and a9 are each independently an integer from 0 to 10,
$R_1$ is a group represented by Formula 2-1 or a group represented by Formula 2-2,
$R_2$ to $R_5$ are each independently selected from a group represented by Formula 2-3, a group represented by Formula 2-4, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$,
$R_6$ to $R_9$, $R_{11}$, and $R_{12}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_4)(Q_5)(Q_6)$, —$N(Q_4)(Q_5)$, —$B(Q_4)(Q_5)$, —$C(=O)(Q_4)$, —$S(=O)_2(Q_4)$, and —$P(=O)(Q_4)(Q_5)$,
b1 is an integer from 1 to 10, wherein, when b1 is two or more, two or more *-$(L_1)_{a1}$-$R_1$(s) are identical to or different from each other, b2 is an integer from 1 to 10, wherein, when b2 is two or more, two or more *-$(L_2)_{a2}$-$R_2$(s) are identical to or different from each other, b4 is an integer from 0 to 5, wherein, when b4 is two or more, two or more *-$(L_4)_{a4}$-$R_4$(s) are identical to or different from each other, b5 is an integer from 0 to 6, wherein, when b5 is two or more, two or more *-$(L_5)_{a5}$-$R_5$(s) are identical to or different from each other, at least one substituent of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cycloalkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cycloalkoxy group;

a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cycloalkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$), and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), $Q_1$ to $Q_6$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, a monovalent non-aromatic condensed heteropolycyclic group, a biphenyl group, and a terphenyl group, and

* and *' each indicate a binding site to a neighboring atom.

* * * * *